(12) United States Patent
Schmid et al.

(10) Patent No.: US 7,763,065 B2
(45) Date of Patent: Jul. 27, 2010

(54) BALLOON EXPANDABLE CRUSH-RECOVERABLE STENT DEVICE

(75) Inventors: Eric V. Schmid, San Diego, CA (US); Andrew Morris, San Diego, CA (US); John Nguyen, San Diego, CA (US); Robert F Eisele, Carlsbad, CA (US); Steven C Howard, San Diego, CA (US); Orlando M Padilla, Laguna Niguel, CA (US); Philip J Simpson, Escondido, CA (US)

(73) Assignee: REVA Medical, Inc., San Diego, CA (US)

( * ) Notice: Subject to any disclaimer, the term of this patent is extended or adjusted under 35 U.S.C. 154(b) by 1257 days.

(21) Appl. No.: 10/897,235

(22) Filed: Jul. 21, 2004

(65) Prior Publication Data
US 2006/0020324 A1   Jan. 26, 2006

(51) Int. Cl.
    *A61F 2/92* (2006.01)
(52) U.S. Cl. ..................................... 623/1.15
(58) Field of Classification Search .................. 623/1.15
    See application file for complete search history.

(56) References Cited

U.S. PATENT DOCUMENTS

| | | |
|---|---|---|
| 3,620,218 A | 11/1971 | Schmitt |
| 4,261,390 A | 4/1981 | Belofsky |
| 4,383,555 A | 5/1983 | Finley |
| 4,553,545 A | 11/1985 | Maass et al. |
| 4,576,532 A | 3/1986 | Hanson et al. |
| 4,714,508 A | 12/1987 | Chivens et al. |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,762,129 A | 8/1988 | Bonzel |
| 4,776,337 A | 10/1988 | Palmaz |

(Continued)

FOREIGN PATENT DOCUMENTS

EP     0756853    2/1997

(Continued)

OTHER PUBLICATIONS

Asahara, T. "Local delivery of vascular endothelial growth factor accelerates reendothelialization and attenuates intimal hyperplasia in balloon-insured rate carotid artery," Circulation 91: 2793-2801, 1995.

(Continued)

*Primary Examiner*—Anhtuan T Nguyen
*Assistant Examiner*—Ryan J Severson
(74) *Attorney, Agent, or Firm*—Knobbe Martens Olson & Bear, LLP

(57) ABSTRACT

An intraluminal, balloon expandable stent for implantation in a body lumen is disclosed. The present invention provides a lumen support stent with an unobstructed through-lumen for use in a blood vessel. A constraining mechanism is provided for securely maintaining the stent in the collapsed condition during delivery. The stent is preferably formed with a series of interconnected slide and lock mechanisms for permitting movement from a collapsed condition to an expanded condition and inhibiting radial recoil from the expanded condition. The stent may be formed from a shape memory alloy for providing crush-recovery after deployment.

67 Claims, 30 Drawing Sheets

U.S. PATENT DOCUMENTS

| | | |
|---|---|---|
| 4,817,600 A | 4/1989 | Herms et al. |
| 4,877,030 A | 10/1989 | Beck et al. |
| 4,922,905 A | 5/1990 | Strecker |
| 4,954,126 A | 9/1990 | Wallsten |
| 4,980,449 A | 12/1990 | Kohn et al. |
| 5,007,926 A | 4/1991 | Devbyshire |
| 5,040,548 A | 8/1991 | Yock |
| 5,059,211 A | 10/1991 | Stack et al. |
| 5,061,273 A | 10/1991 | Yock |
| 5,092,877 A | 3/1992 | Pinchuk |
| 5,099,060 A | 3/1992 | Kohn et al. |
| 5,108,416 A | 4/1992 | Ryan et al. |
| 5,140,094 A | 8/1992 | Kohn et al. |
| 5,151,100 A | 9/1992 | Abele et al. |
| 5,158,548 A | 10/1992 | Lau et al. |
| 5,192,307 A | 3/1993 | Wall |
| 5,194,570 A | 3/1993 | Kohn et al. |
| 5,195,984 A | 3/1993 | Schatz |
| 5,197,978 A | 3/1993 | Hess |
| 5,198,507 A | 3/1993 | Kohn et al. |
| 5,216,115 A | 6/1993 | Kohn et al. |
| 5,230,349 A | 7/1993 | Langberg |
| 5,232,445 A | 8/1993 | Bonzel |
| 5,242,399 A | 9/1993 | Lau et al. |
| 5,242,997 A | 9/1993 | Kohn et al. |
| 5,264,537 A | 11/1993 | Kohn et al. |
| 5,266,073 A | 11/1993 | Wall |
| 5,282,823 A | 2/1994 | Schwartz et al. |
| 5,300,085 A | 4/1994 | Yock |
| 5,306,286 A | 4/1994 | Stack et al. |
| 5,306,294 A | 4/1994 | Winston et al. |
| 5,317,077 A | 5/1994 | Kohn et al. |
| 5,344,426 A | 9/1994 | Lau et al. |
| 5,350,395 A | 9/1994 | Yock |
| 5,397,355 A | 3/1995 | Marin et al. |
| 5,402,554 A | 4/1995 | Oetiker |
| 5,421,955 A | 6/1995 | Lau et al. |
| 5,423,321 A | 6/1995 | Fontenot |
| 5,423,885 A | 6/1995 | Williams |
| 5,441,515 A | 8/1995 | Khosravi et al. |
| 5,443,496 A | 8/1995 | Schwartz et al. |
| 5,443,500 A | 8/1995 | Sigwart |
| 5,445,646 A | 8/1995 | Euteneur et al. |
| 5,449,382 A | 9/1995 | Dayton |
| 5,451,233 A | 9/1995 | Yock |
| 5,464,450 A | 11/1995 | Buscemi et al. |
| 5,476,508 A | 12/1995 | Amstrup |
| 5,484,449 A | 1/1996 | Amundson et al. |
| 5,490,962 A | 2/1996 | Cima et al. |
| 5,496,275 A | 3/1996 | Sirhan et al. |
| 5,496,346 A | 3/1996 | Horzewski et al. |
| 5,514,154 A | 5/1996 | Lau et al. |
| 5,527,337 A | 6/1996 | Stack et al. |
| 5,545,135 A | 8/1996 | Iacob et al. |
| 5,545,138 A | 8/1996 | Fugoso et al. |
| 5,549,556 A | 8/1996 | Ndondo-Lay et al. |
| 5,549,662 A | 8/1996 | Fordenbacher |
| 5,551,954 A | 9/1996 | Buscemi et al. |
| 5,554,182 A | 9/1996 | Dinh et al. |
| 5,556,413 A | 9/1996 | Lam |
| 5,571,166 A | 11/1996 | Dinh et al. |
| 5,575,816 A | 11/1996 | Rudnick et al. |
| 5,578,075 A | 11/1996 | Dayton |
| 5,587,507 A | 12/1996 | Kohn et al. |
| 5,591,172 A | 1/1997 | Bachmann et al. |
| 5,591,223 A | 1/1997 | Lock et al. |
| 5,591,224 A | 1/1997 | Schwartz et al. |
| 5,591,227 A | 1/1997 | Dinh et al. |
| 5,599,352 A | 2/1997 | Dinh et al. |
| 5,603,722 A | 2/1997 | Phan et al. |
| 5,607,463 A | 3/1997 | Schwartz et al. |
| 5,618,299 A | 4/1997 | Khosravi et al. |
| 5,626,600 A | 5/1997 | Horzewski et al. |
| 5,628,785 A | 5/1997 | Schwartz et al. |
| 5,629,077 A | 5/1997 | Turnlund et al. |
| 5,632,771 A | 5/1997 | Boatman et al. |
| 5,643,312 A | 7/1997 | Fischell et al. |
| 5,643,314 A | 7/1997 | Carpenter et al. |
| 5,643,339 A | 7/1997 | Kavteladze et al. |
| 5,649,977 A | 7/1997 | Campbell |
| 5,651,174 A | 7/1997 | Schwartz et al. |
| 5,658,995 A | 8/1997 | Kohn et al. |
| 5,670,602 A | 9/1997 | Kohn et al. |
| 5,681,345 A | 10/1997 | Euteneuer |
| 5,697,967 A | 12/1997 | Dinh et al. |
| 5,707,387 A | 1/1998 | Wijay |
| 5,725,549 A | 3/1998 | Lam |
| 5,733,328 A | 3/1998 | Fordenbacher |
| 5,735,872 A | 4/1998 | Carpenter et al. |
| 5,741,293 A | 4/1998 | Wijay |
| 5,749,888 A | 5/1998 | Yock |
| 5,755,708 A | 5/1998 | Segal |
| 5,759,186 A | 6/1998 | Bachmann et al. |
| 5,766,710 A | 6/1998 | Turnlund et al. |
| 5,769,868 A | 6/1998 | Yock |
| 5,797,951 A | 8/1998 | Mueller |
| 5,799,384 A | 9/1998 | Schwartz et al. |
| 5,800,393 A | 9/1998 | Sahota |
| 5,800,507 A | 9/1998 | Schwartz |
| 5,836,965 A | 11/1998 | Jendersee et al. |
| 5,849,034 A | 12/1998 | Schwartz |
| 5,851,217 A | 12/1998 | Wolff et al. |
| 5,851,231 A | 12/1998 | Wolff et al. |
| 5,855,600 A | 1/1999 | Alt |
| 5,855,802 A | 1/1999 | Acciai et al. |
| 5,868,747 A | 2/1999 | Ochoa et al. |
| 5,876,419 A | 3/1999 | Carpenter et al. |
| 5,893,840 A | 4/1999 | Hull et al. |
| 5,906,639 A | 5/1999 | Rudnick et al. |
| 5,910,816 A | 6/1999 | Fontenot et al. |
| 5,921,952 A | 7/1999 | Desmond, III et al. |
| 5,944,726 A | 8/1999 | Blaeser et al. |
| 5,951,586 A | 9/1999 | Berg et al. |
| 5,954,729 A | 9/1999 | Bachmann et al. |
| 5,957,971 A | 9/1999 | Schwartz |
| 5,976,181 A | 11/1999 | Whelan et al. |
| 5,984,963 A | 11/1999 | Ryan et al. |
| 5,989,280 A | 11/1999 | Euteneur et al. |
| 6,007,545 A | 12/1999 | Venturelli |
| 6,015,387 A | 1/2000 | Schwartz et al. |
| 6,019,785 A | 2/2000 | Strecker |
| 6,033,436 A * | 3/2000 | Steinke et al. ............... 623/1.15 |
| 6,036,715 A | 3/2000 | Yock |
| 6,048,521 A | 4/2000 | Kohn et al. |
| 6,080,190 A | 6/2000 | Schwartz |
| 6,093,157 A | 7/2000 | Chandrasekaran |
| 6,120,491 A | 9/2000 | Kohn et al. |
| 6,125,523 A | 10/2000 | Brown et al. |
| 6,132,457 A | 10/2000 | Chobotov |
| 6,160,084 A | 12/2000 | Langer et al. |
| 6,171,334 B1 | 1/2001 | Cox |
| 6,179,878 B1 | 1/2001 | Duerig et al. |
| 6,183,503 B1 | 2/2001 | Hart et al. |
| 6,190,403 B1 | 2/2001 | Fishchell et al. |
| 6,197,789 B1 | 3/2001 | Grainger |
| 6,214,037 B1 | 4/2001 | Mitchell et al. |
| 6,224,626 B1 | 5/2001 | Steinke |
| 6,238,430 B1 | 5/2001 | Klumb et al. |
| 6,258,117 B1 | 7/2001 | Camrud et al. |
| 6,262,079 B1 | 7/2001 | Grainger et al. |
| 6,264,624 B1 | 7/2001 | Desmond, III et al. |
| 6,264,672 B1 | 7/2001 | Fisher |
| 6,280,473 B1 | 8/2001 | Lemperle et al. |
| 6,283,983 B1 | 9/2001 | Makower et al. |

| | | | | | | |
|---|---|---|---|---|---|---|
| 6,284,862 B1 | 9/2001 | Kohn et al. | | 7,141,063 B2 | 11/2006 | White et al. |
| 6,287,329 B1 | 9/2001 | Duerig et al. | | 7,175,653 B2 | 2/2007 | Gaber |
| 6,287,333 B1 | 9/2001 | Appling et al. | | 7,229,473 B2 | 6/2007 | Falotico et al. |
| 6,302,907 B1 | 10/2001 | Hijlkema | | 2001/0010015 A1 | 7/2001 | Hijlkema |
| 6,309,350 B1 | 10/2001 | Van Tassel et al. | | 2001/0020173 A1 | 9/2001 | Klumb et al. |
| 6,319,277 B1 | 11/2001 | Rudnick et al. | | 2001/0029378 A1 | 10/2001 | Blaeser et al. |
| 6,319,492 B1 | 11/2001 | Kohn et al. | | 2001/0044651 A1 * | 11/2001 | Steinke et al. ............... 623/1.16 |
| 6,322,586 B1 | 11/2001 | Monroe et al. | | 2002/0040238 A1 | 4/2002 | Rudnick et al. |
| 6,350,277 B1 | 2/2002 | Kocur | | 2002/0052641 A1 | 5/2002 | Monroe et al. |
| 6,359,102 B1 | 3/2002 | Kemnitzer et al. | | 2002/0072656 A1 | 6/2002 | Van Tassel et al. |
| 6,383,211 B1 | 5/2002 | Staehle | | 2002/0077693 A1 | 6/2002 | Barclay et al. |
| 6,388,043 B1 | 5/2002 | Langer et al. | | 2002/0095204 A1 | 7/2002 | Thompson et al. |
| 6,391,032 B2 | 5/2002 | Blaeser et al. | | 2002/0120322 A1 | 8/2002 | Thompson et al. |
| 6,409,750 B1 | 6/2002 | Hyodoh et al. | | 2002/0120323 A1 | 8/2002 | Thompson et al. |
| 6,409,752 B1 | 6/2002 | Boatman et al. | | 2002/0123791 A1 | 9/2002 | Harrison |
| 6,447,508 B1 | 9/2002 | Sharkey et al. | | 2002/0138081 A1 | 9/2002 | Blaeser et al. |
| 6,451,034 B1 | 9/2002 | Gifford, III et al. | | 2002/0138126 A1 | 9/2002 | Camrud et al. |
| 6,475,477 B1 | 11/2002 | Kohn et al. | | 2002/0147489 A1 | 10/2002 | Hong et al. |
| 6,485,510 B1 | 11/2002 | Camrud et al. | | 2002/0156456 A1 | 10/2002 | Fisher |
| 6,488,700 B2 | 12/2002 | Klumb et al. | | 2002/0156457 A1 | 10/2002 | Fisher |
| 6,491,704 B2 | 12/2002 | Gifford, III et al. | | 2003/0045923 A1 | 3/2003 | Bashiri |
| 6,491,705 B2 | 12/2002 | Gifford, III et al. | | 2003/0074043 A1 | 4/2003 | Thompson |
| 6,491,938 B2 | 12/2002 | Kunz et al. | | 2003/0078649 A1 | 4/2003 | Camrud et al. |
| 6,527,791 B2 | 3/2003 | Fisher | | 2003/0120334 A1 | 6/2003 | Gerberding |
| 6,530,940 B2 | 3/2003 | Fisher | | 2003/0176914 A1 | 9/2003 | Rabkin et al. |
| 6,530,958 B1 | 3/2003 | Cima et al. | | 2003/0199969 A1 | 10/2003 | Steinke et al. |
| 6,562,021 B1 | 5/2003 | Derbin et al. | | 2003/0208262 A1 | 11/2003 | Gaber |
| 6,565,582 B2 | 5/2003 | Gifford, III et al. | | 2003/0211135 A1 | 11/2003 | Greenhalgh et al. |
| 6,565,596 B1 | 5/2003 | White et al. | | 2003/0212451 A1 | 11/2003 | Cox et al. |
| 6,569,191 B1 | 5/2003 | Hogan | | 2003/0220682 A1 | 11/2003 | Kujawski |
| 6,569,441 B2 | 5/2003 | Kunz et al. | | 2004/0054400 A1 | 3/2004 | Granada |
| 6,582,458 B1 | 6/2003 | White et al. | | 2004/0062788 A1 | 4/2004 | Richter |
| 6,582,472 B2 | 6/2003 | Hart | | 2004/0068316 A1 | 4/2004 | Schaeffer |
| 6,602,497 B1 | 8/2003 | Kohn et al. | | 2004/0086458 A1 | 5/2004 | Kohn et al. |
| 6,607,551 B1 | 8/2003 | Sullivan et al. | | 2004/0086462 A1 | 5/2004 | Kohn et al. |
| 6,613,073 B1 | 9/2003 | White et al. | | 2004/0093073 A1 | 5/2004 | Lowe et al. |
| 6,620,356 B1 | 9/2003 | Wong et al. | | 2004/0097959 A1 | 5/2004 | Thompson |
| 6,623,491 B2 | 9/2003 | Thompson | | 2004/0106971 A1 | 6/2004 | Schwartz et al. |
| 6,623,518 B2 | 9/2003 | Thompson et al. | | 2004/0106977 A1 | 6/2004 | Sullivan et al. |
| 6,623,521 B2 | 9/2003 | Steinke et al. | | 2004/0133260 A1 | 7/2004 | Schwartz et al. |
| 6,645,143 B2 | 11/2003 | Van Tassel et al. | | 2004/0143319 A1 | 7/2004 | Schwartz et al. |
| 6,652,555 B1 | 11/2003 | Van Tassel et al. | | 2004/0167616 A1 | 8/2004 | Camrud et al. |
| 6,659,105 B2 | 12/2003 | Burbank et al. | | 2004/0186551 A1 | 9/2004 | Kao et al. |
| 6,676,658 B2 | 1/2004 | Burbank et al. | | 2004/0191175 A1 | 9/2004 | Kohn et al. |
| 6,682,541 B1 | 1/2004 | Gifford, III et al. | | 2004/0193251 A1 | 9/2004 | Rudnick et al. |
| 6,685,736 B1 | 2/2004 | White et al. | | 2004/0224003 A1 | 11/2004 | Schultz |
| 6,689,153 B1 | 2/2004 | Skiba | | 2004/0236401 A1 | 11/2004 | Shin et al. |
| 6,689,158 B1 | 2/2004 | White et al. | | 2004/0243217 A1 | 12/2004 | Andersen et al. |
| 6,695,857 B2 | 2/2004 | Gifford, III et al. | | 2004/0243218 A1 | 12/2004 | Schaeffer |
| 6,699,257 B2 | 3/2004 | Gifford, III et al. | | 2005/0038503 A1 | 2/2005 | Greenhalgh et al. |
| 6,699,280 B2 | 3/2004 | Camrud et al. | | 2005/0106119 A1 | 5/2005 | Brandom et al. |
| 6,709,449 B2 | 3/2004 | Camrud et al. | | 2005/0123481 A1 | 6/2005 | Kohn et al. |
| 6,720,402 B2 | 4/2004 | Langer et al. | | 2005/0165203 A1 | 7/2005 | Kohn et al. |
| 6,736,838 B1 | 5/2004 | Richter | | 2006/0024266 A1 | 2/2006 | Brandom et al. |
| 6,746,477 B2 | 6/2004 | Moore | | 2006/0026815 A1 | 2/2006 | Padilla et al. |
| 6,749,627 B2 | 6/2004 | Thompson et al. | | 2006/0034769 A1 | 2/2006 | Kohn et al. |
| 6,786,922 B2 | 9/2004 | Schaeffer | | 2006/0036316 A1 | 2/2006 | Zeltinger et al. |
| 6,790,221 B2 | 9/2004 | Monroe et al. | | 2006/0115449 A1 | 6/2006 | Pacetti |
| 6,792,979 B2 | 9/2004 | Konya et al. | | 2006/0136041 A1 | 6/2006 | Schmid et al. |
| 6,802,849 B2 | 10/2004 | Blaeser et al. | | 2006/0182779 A1 | 8/2006 | Brandom et al. |
| 6,852,308 B2 | 2/2005 | Kohn et al. | | 2006/0204440 A1 | 9/2006 | Kohn et al. |
| 6,869,143 B2 | 3/2005 | Secord | | 2007/0010870 A1 | 1/2007 | Alt et al. |
| 6,878,159 B2 | 4/2005 | Iwasaka et al. | | 2007/0032854 A1 | 2/2007 | Schmid et al. |
| 6,916,868 B2 | 7/2005 | Kemnitzer et al. | | 2007/0032857 A1 | 2/2007 | Schmid et al. |
| 6,951,053 B2 | 10/2005 | Padilla et al. | | 2007/0061004 A1 | 3/2007 | Steinke |
| 6,962,604 B2 | 11/2005 | Hijlkema | | 2007/0142901 A1 | 6/2007 | Steinke |
| 6,964,680 B2 | 11/2005 | Shanley | | | | |
| 6,974,472 B2 | 12/2005 | Hong et al. | | FOREIGN PATENT DOCUMENTS | | |
| 6,974,475 B1 | 12/2005 | Wall | | | | |
| 6,991,647 B2 | 1/2006 | Jadhav | | JP | 9-313617 | 12/1997 |
| 7,041,126 B2 | 5/2006 | Shin et al. | | WO | WO 90/14046 A1 | 11/1990 |
| 7,056,493 B2 | 6/2006 | Kohn et al. | | WO | WO 94/21196 A2 | 9/1994 |
| 7,128,756 B2 | 10/2006 | Lowe et al. | | WO | WO 94/21196 A3 | 2/1995 |

| | | |
|---|---|---|
| WO | WO 96/14030 A1 | 5/1996 |
| WO | WO 97/07751 A1 | 3/1997 |
| WO | WO 97/42911 A1 | 11/1997 |
| WO | WO 98/22045 | 5/1998 |
| WO | WO 98/22073 A2 | 5/1998 |
| WO | WO 98/22073 A3 | 2/1999 |
| WO | WO 99/08740 A1 | 2/1999 |
| WO | WO 99/15106 A1 | 4/1999 |
| WO | WO 99/40874 A1 | 8/1999 |
| WO | WO 99/65421 A2 | 12/1999 |
| WO | WO 99/65421 A3 | 1/2000 |
| WO | WO 00/09195 A1 | 2/2000 |
| WO | WO 00/10623 A1 | 3/2000 |
| WO | WO 00/30565 A1 | 6/2000 |
| WO | WO 00/59405 A1 | 10/2000 |
| WO | WO 00/62708 A1 | 10/2000 |
| WO | WO 00/71058 A1 | 11/2000 |
| WO | WO 01/24735 A1 | 4/2001 |
| WO | WO 01/35864 A1 | 5/2001 |
| WO | WO 01/51114 A2 | 7/2001 |
| WO | WO 01/70298 A2 | 9/2001 |
| WO | WO 01/87180 A2 | 11/2001 |
| WO | WO 01/51114 A3 | 1/2002 |
| WO | WO 01/70298 A3 | 2/2002 |
| WO | WO 00/62708 C2 | 6/2002 |
| WO | WO 01/87180 A3 | 6/2002 |
| WO | WO 02/47582 A2 | 6/2002 |
| WO | WO 02/053204 A2 | 7/2002 |
| WO | WO 02/054990 A2 | 7/2002 |
| WO | WO 02/047582 A3 | 10/2002 |
| WO | WO 02/054990 A3 | 11/2002 |
| WO | WO 02/053204 A3 | 3/2003 |
| WO | WO 03/022178 A1 | 3/2003 |
| WO | WO 03/047464 A2 | 6/2003 |
| WO | WO 03/057076 A1 | 7/2003 |
| WO | WO 03/047464 A3 | 9/2003 |
| WO | WO 03/047464 C2 | 11/2003 |
| WO | WO 03/094798 A1 | 11/2003 |
| WO | WO 03/099161 A2 | 12/2003 |
| WO | WO 03/099161 A3 | 2/2004 |
| WO | WO 2004/019820 A1 | 3/2004 |
| WO | WO 2004/026112 A2 | 4/2004 |
| WO | WO 2004/032803 A1 | 4/2004 |
| WO | WO 2004/026112 C2 | 6/2004 |
| WO | WO 2004/026112 A3 | 10/2004 |
| WO | WO 2004/096340 A1 | 11/2004 |
| WO | WO 2004/110312 A1 | 12/2004 |
| WO | WO 2006/010636 A1 | 2/2006 |
| WO | WO 2006/014596 A1 | 2/2006 |
| WO | WO 2006/020616 A1 | 2/2006 |
| WO | WO 2006/107608 A1 | 10/2006 |
| WO | WO 2007/084444 A2 | 7/2007 |

OTHER PUBLICATIONS

Autieri, M.V. et al. "Antisense oligonucleotides to the p65 subunit of NF-Kb inhibit human vascualr smooth muscle cell adherence and proliferation and prevent neointima formation in rat carotid arteries," Biochemical and Biophysical Research Communications 213: 827-836, 1995.
Brauner, R. "Controlled periadverntitial administration of verapamil inhibits neointimal smooth muscle cell proliferation and ameliorates vasomotor abnormalities in experimental vein bypass grafts," The Journal of Thoracic and Cardiovascular Surgery 114: 53-63, 1997.
Carmeliet, P. et al. "Inhibitory role of plasminogen activator inhibitor-1 in arterial wound healing and neointima formation," Circulation 96: 3180-3191, 1997.
Epstein, S.E. et al. "Cytotoxic effects of a recombinant chimeric toxin on rapidly proliferating vascular smooth muscle cells," Circulation 84: 778-787, 1991.
Hu, Y. "Inhibition of neointima hyperplasia of mouse vein grafts by locally applied suramin," Circulation 100: 861-868, 1999.
Kurisu, Y. et al. "Protective effect of beraprost sodium, a stable prostacyclin analogue, on cardiac allograft vasculopathy in rats," Hiroshima Journal of Medical Science 56: 11-19, 1997.
Morishita, R. et al. "Novel in vitro gene transfer method for study of local modulators in vascular smooth muscle cells," Hypertension 21: 894-899, 1993.
Nerem, R.M. et al. "Tissue engineering and the vascular system, synthetic biodegradable polymer scaffolds," pp. 164-185, 1997.
Von Der Leyen, H.E. et al. "Gene therapy neointimal vascular lesion: in vivo transfer of endothelial cell nitric oxide synthase gene," PNAS USA 92:1137-1141, 1995.
Yasukawa, H. "Inhibition of intimal hyperplasia after balloon injury by antibodies to intercellular adhesion molecule-1 and lymphocyte funtion, Associated antigen-1," Circulation 95: 1515-1522, 1997.
*International Search Report and Written Opinion,* mailed Sep. 11, 2005 in related International Application No. PCT/US2005/025683, 13 pages.
Balcon, R. et al., *Recommendations on stent manufacture, implantation and utilization,* European Heart Journal, Oct. 1997, vol. 18, pp. 1536-1547.
Charles, Roger et al., *Ceramide-Coated Balloon Catheters Limit Neointimal Hyperplasia After Stretch Injury in Carotid Arteries,* Circulation Research, 2000; 87; pp. 282-288.
Coroneos, Emmanuel et al., *Differential Regulation of Sphingomyelinase and Ceramidase Activities by Growth Factors and Cytokines,* The Journal of Biological Chemistry, Oct. 6, 1995, vol. 270, No. 40, pp. 23305-23309.
Coroneos, Emmanuel et al., *Sphingolipid metabolites differentially regulate extracellular signal-regulated kinase and stress-activated protein kinase cascades,* Biochemical Journal, 1196; 316, pp. 13-17 (Printed in Great Britain).
Jacobs, Leila S. et al., *Sphingolipids as mediators of effects of platelet-derived growth factor in vascular smooth muscle cells,* American Journal of Physiology (American Physiological Society), 1993, pp. C740-C747.
Tanguay, Jean Francois et al., *Current Status of Biodegradable Stents,* Cardiology Clinics, Contemporary Interventional Techniques, Nov. 1994, vol. 12, No. 4, pp. 699-713, W.B. Saunders Company.
Nikol, S. et al., *Molecular biology and post-angioplasty restenosis,* Atherosclerosis, 1996; 123, pp. 17-31.
Phillips, Paul S. MD, et al., *The Stenter's Notebook,* 1998, (entire book), Physicians' Press, Birmingham, Michigan.
Ratner, Buddy D. et al., *Biomaterials Science, An Introduction to Materials in Medicine,* 2nd Edition, 2004, (entire book), Elsevier Academic Press.
Serruys, Patrick W. et al., *Handbook of Coronary Stents,* Fourth Edition, 2002, (entire book), Martin Dunitz Ltd.
Atala, Anthony et al., *Synthetic Biodegradable Polymer Scaffolds,* 1997, (entire book), Birkhauser Boston.
Co-pending U.S. Appl. No. 60/866,281, filed Nov. 17, 2006. Title: Halogen-Containing Aromatic Polyesters and Polyamides for Medical Applications.
Co-pending U.S. Appl. No. 60/885,600, filed Jan. 18, 2007. Title: Halogen-Containing Aromatic Polyesters and Polyamides for Medical Applications.
Co-pending U.S. Appl. No. 60/852,471, filed Oct. 17, 2006. Title: N-Substituted Monomers and Polymers.
Co-pending U.S. Appl. No. 60/852,513, filed Oct. 17, 2006. Title: N-Substituted Monomers and Polymers.

* cited by examiner

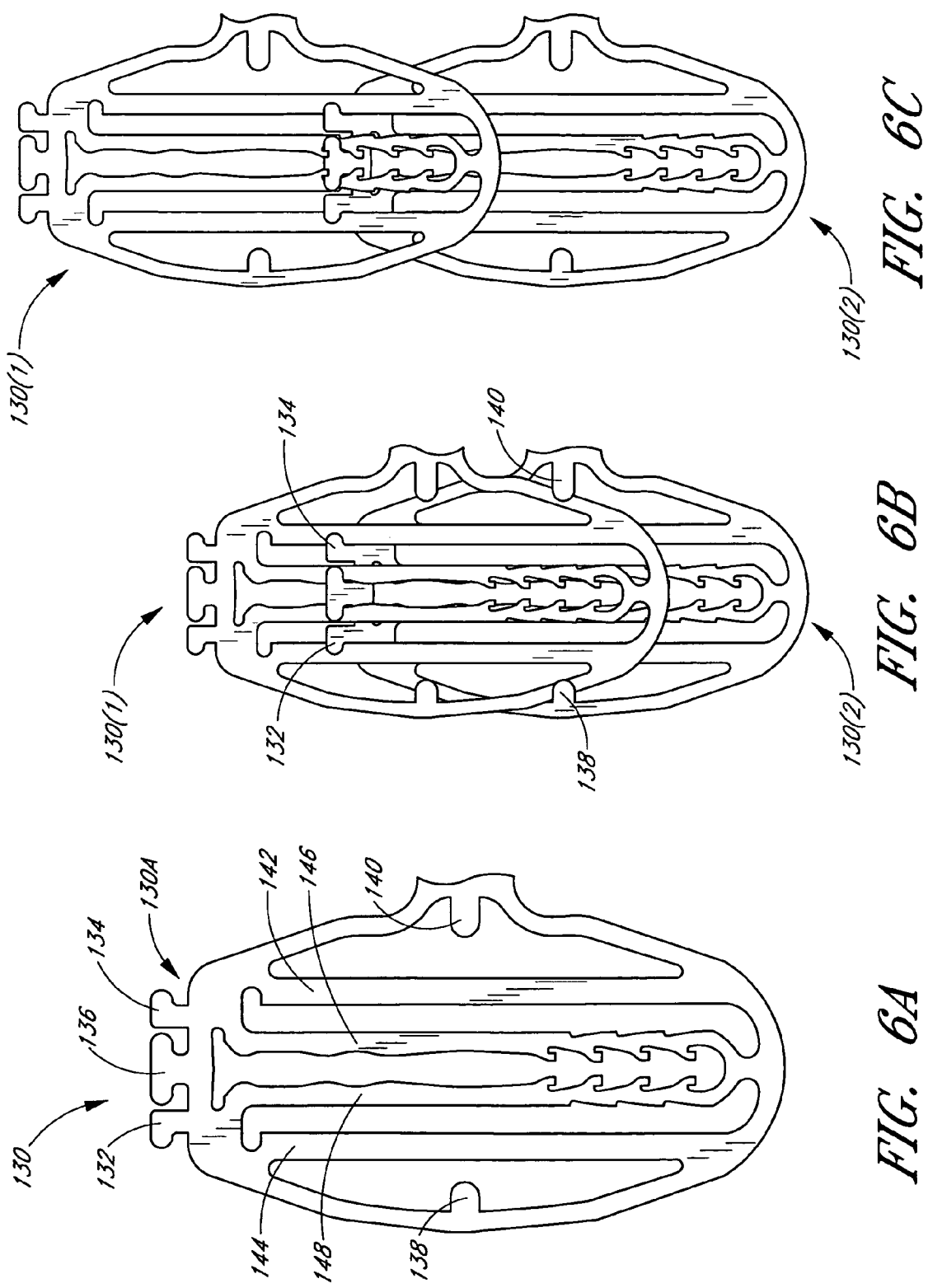

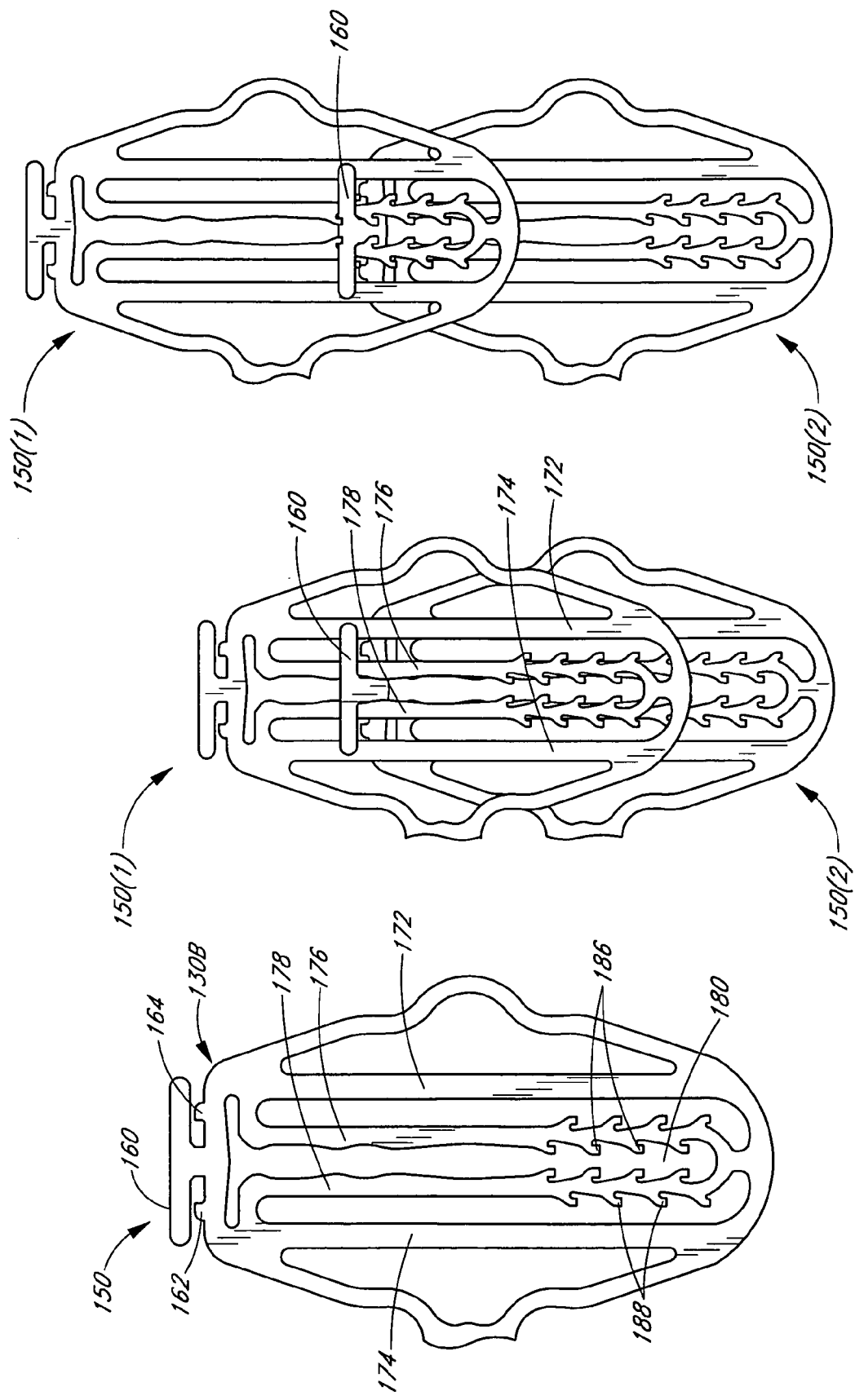

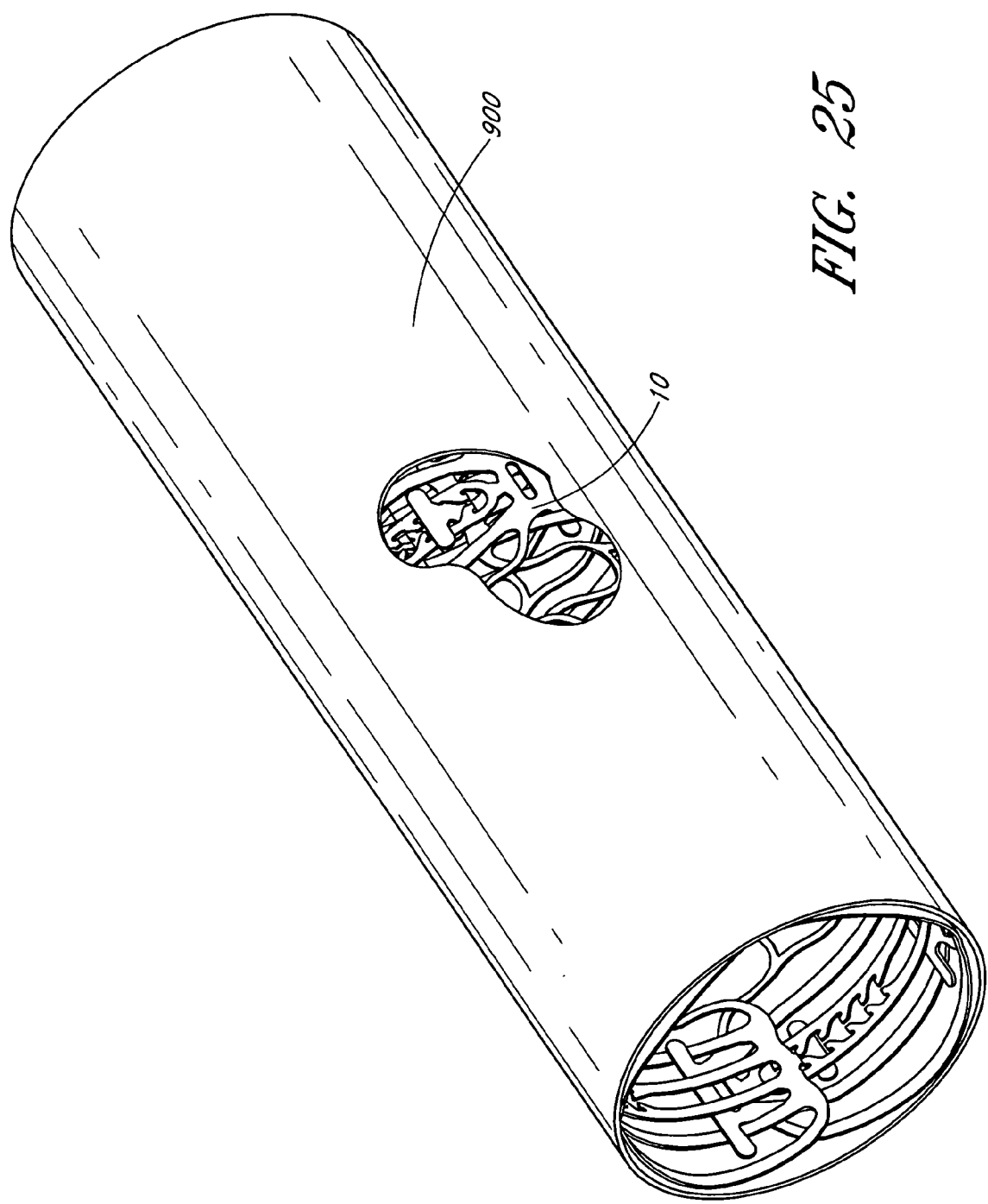

BALLOON EXPANDABLE CRUSH-RECOVERABLE STENT DEVICE

BACKGROUND OF THE INVENTION

1. Field of the Invention

The present invention relates generally to expandable medical implants for supporting a body lumen and, more particularly, to expandable, intraluminal devices, generally referred to as stents.

2. Description of the Related Art

Stents are implanted into body lumens, such as blood vessels, to maintain the patency of the lumens. These devices are frequently used in the treatment of atherosclerotic stenoses in blood vessels, especially in conjunction with percutaneous transluminal coronary angioplasty (PTCA) procedures. After treating a blood vessel, a stent is implanted to support the vessel wall and thereby reduce the likelihood of restenosis. Stents are most commonly implanted in coronary arteries; however, stents may also be used in a wide variety of other body lumens. For example, stents may be deployed in the biliary, carotid, superficial femoral and popliteal arteries or even veins Over the years, a wide variety of stent types have been proposed. Although the structures of stents may vary substantially, virtually all stents are configured to be expandable from a collapsed condition having a small diameter to an expanded condition having a larger diameter. While in the collapsed condition, the stent is delivered through the blood vessel, or other body lumen, to the treatment site. After the treatment site is reached, the stent is radially expanded to an implantable size for supporting the vessel wall. Expansion of the stent from the collapsed condition to the expanded condition can be achieved in a variety of different ways. Various types of stents are described below based on their means for expansion. For additional information, a variety of stents types are described by Balcon et al., "Recommendations on Stent Manufacture, Implantation and Utilization," European Heart Journal (1997), vol. 18, pages 1536-1547, and Phillips, et al., "The Stenter's Notebook," Physician's Press (1998), Birmingham, Mich.

Balloon expandable stents are manufactured in the collapsed condition and are expanded to a desired diameter with a balloon. During delivery, a balloon expandable stent is typically mounted on the exterior of an inflatable balloon located along the distal end portion of a catheter. After reaching the treatment site, the stent is expanded from the collapsed condition to the expanded condition by inflating the balloon. The stent is typically expanded to a diameter that is greater than or equal to the inner diameter of the body lumen. The expandable stent structure may be held in the expanded condition by mechanical deformation of the stent as taught in, for example, U.S. Pat. No. 4,733,665 to Palmaz. Alternatively, balloon expandable stents may be held in the expanded condition by engagement of the stent walls with respect to one another as disclosed in, for example, U.S. Pat. No. 4,740,207 to Kreamer, U.S. Pat. No. 4,877,030 to Beck et al., and U.S. Pat. No. 5,007,926 to Derbyshire. Further still, the stent may be held in the expanded condition by one-way engagement of the stent walls together with endothelial growth into the stent, as disclosed in U.S. Pat. No. 5,059,211 to Stack et al.

Balloon expandable stents are typically manufactured from stainless steel and generally have a high radial strength. The term "radial strength," as used herein, describes the external pressure that a stent is able to withstand without incurring clinically significant damage. Due to their high radial strength, balloon expandable stents are commonly used in the coronary arteries to ensure patency of the vessel. During deployment in a body lumen, the inflation of the balloon can be regulated for expanding the stent to a particular desired diameter. Accordingly, balloon expandable stents are often preferred in applications wherein precise placement and sizing are important. Balloon expandable stents are also commonly used for direct stenting, wherein there is no pre-dilation of the vessel before stent deployment. Rather, during direct stenting, the expansion of the inflatable balloon dilates the vessel while also expanding the stent.

Although balloon expandable stents are the first stent type to be widely used in clinical applications, it is well recognized that balloon expandable stents suffer from a variety of shortcomings which may limit their effectiveness in many important applications. For example, in one significant shortcoming, existing balloon expandable stents are not biased toward the expanded condition and therefore do not return to the expanded condition after being deformed, bent, or pinched. Accordingly, when a high external pressure overcomes the radial strength of a balloon expandable stent, the stent may be caused to permanently deform inward (i.e. collapse) such that the lumen is substantially reduced in size. Worse yet, external pressures may cause the stent to completely collapse, with potentially fatal clinical implications. Therefore, balloon expandable stents are not well-adapted for use in blood vessels which are subjected to large torsional or flexion/extension stresses (e.g., the superficial femoral artery and popliteal artery) and/or wherein the stent is vulnerable to large external pressures (e.g., the superficial femoral artery and carotid artery).

In another shortcoming, balloon expandable stents often exhibit substantial recoil (i.e., a reduction in diameter) immediately following deflation of the inflatable balloon. Accordingly, it may be necessary to over-inflate the balloon during deployment of the stent to compensate for the subsequent recoil. This is disadvantageous because it has been found that over-inflation may damage the blood vessel. Furthermore, a deployed balloon expandable stent may exhibit chronic recoil over time, thereby reducing the patency of the lumen. Still further, balloon expandable stents often exhibit foreshortening (i.e., a reduction in length) during expansion, thereby creating undesirable stresses along the vessel wall and making stent placement less precise. Still further, many balloon expandable stents, such as the original Palmaz-Schatz stent and later variations, are configured with an expandable mesh having relatively jagged terminal prongs, which increases the risk of injury to the vessel, thrombosis and/or restenosis.

Self-expanding stents are manufactured with a diameter approximately equal to, or larger than, the vessel diameter and are collapsed and constrained at a smaller diameter for delivery to the treatment site. Self-expanding stents may be placed within a sheath or sleeve to constrain the stent in the collapsed condition during delivery. Alternatively, detachable tabs or pins may be used for locking the stent in the collapsed condition. After the treatment site is reached, the constraint mechanism is removed and the stent self-expands to the expanded condition. Typically, self-expansion of the stent results from the inherent properties of the material constituting the stent. Most commonly, self-expanding stents are made of Nitinol or other shape memory alloy.

Because self-expanding stents are biased towards the preset expanded condition, if the self-expanding stent is caused to deform under pressure, the stent will return to its expanded condition when the pressure is removed. Accordingly, self-expanding stents overcome many of the shortcomings, such as the risk of permanent collapse, associated with balloon expandable stents. Therefore, self-expanding stents are often deployed in areas of the body where large external forces may cause the vessel, and therefore the stent, to temporarily deform radially inward. After the external force is reduced or removed, the self-expanding stent returns to its fully expanded condition, thereby eliminating the danger of permanent stent deformation and obstruction of the lumen.

One of the first self-expanding stents used clinically is the braided "WallStent," as described in U.S. Pat. No. 4,954,126 to Wallsten. The WallStent generally comprises a metallic mesh in the form of a Chinese finger cuff. The cuff provides a braided stent that is not superelastic, but technically still falls in the self-expanding stent family. Although the WallStent provided a significant improvement in stent technology for certain applications, such as the treatment of long lesions, the WallStent and other stents of this type often exhibit undesirable metal prongs that remain along the longitudinal ends thereof as a result of the manufacturing process. Another disadvantage of the WallStent is the inherent rigidity of the material (e.g., a cobalt-based alloy having a platinum core) used to form the stent. The combination of the rigidity and the terminal prongs has been found to produce substantial difficulties during navigation through the patient's vasculature. Accordingly, the procedure produces undesirable risks from the standpoint of injury to healthy tissue along the passage to the target vessel.

Another example of a self-expanding stent is disclosed in U.S. Pat. No. 5,192,307 to Wall wherein a stent-like prosthesis is formed of plastic or sheet metal that is expandable or contractible for placement. The stent may be biased in an open position and lockable in a closed position or, alternatively, may be biased towards a closed position and lockable in an open position. In the former case, a pin may be used to hold the stent in the collapsed condition. The pin is removed to allow the stent to assume the expanded condition. One or more hooks may be formed into the wall for locking the stent. The hooks engage complementary recesses formed in an opposing wall to mechanically interlock the rolled up sheet forming the stent.

Although self-expanding stents provide a number of advantages over balloon expandable stents, self-expanding stents also suffer from a wide variety of shortcomings. In one well-recognized shortcoming, self-expanding stents lack the high radial strength of balloon expandable stents and therefore self-expanding stents may deform under relatively low external pressures. In another shortcoming, self-expandable stents often exhibit significant foreshortening during radial expansion. As a result, stents of this type may not provide predictable longitudinal coverage when fully deployed. Furthermore, self-expanding stents necessarily require a constraining mechanism for holding the stent in the collapsed condition during delivery. For example, as described above, a self-expanding stent may be placed in a separate deployment sheath for constraining the stent during delivery. During deployment of a self-expanding stent, the sheath is retracted to uncover the stent incrementally from the distal end to the proximal end, thereby allowing the stent to expand from one end to the other. However, this often results in the stent jumping or springing forward from the delivery system in an undesirable manner, sometimes causing the stent to buckle or bunch up during delivery. Still further, it has been found that self-expanding stents do not re-dilate well in cases of retreatment and are not well suited for direct stenting.

In yet another shortcoming, self-expanding stents typically impose a continuous chronic outward stress on the vessel wall that may create significant risks of damage to the vessel wall and may lead to restenosis. It is common to find that, after two to four weeks, a self-expanding stent has expanded well into the wall of the artery, thereby supporting the vessel from within the smooth muscle layer, rather than from within the lumen. This is not a desirable result since most physicians intuitively feel it is advantageous to preserve the native, physiologically correct vessel properties as far as possible.

In addition, self-expanding stents are currently available only in 0.5 mm increments. This is a problem because exact sizing, within 0.1 to 0.2 mm expanded diameter, may be necessary to adequately reduce the effects of restenosis. Furthermore, these devices are often oversized by up to 30-50% to ensure location retention and vessel patency, thereby producing a chronic outward stress, as described above. Thus, greater selection and adaptability in expanded size is needed. As a result of these and other shortcomings, self-expanding stents have limited effectiveness in many important applications.

Heat expandable stents are similar in nature to self-expanding stents. However, this type of stent utilizes the application of heat to produce expansion of the stent structure. Stents of this type may be formed of a shape memory alloy, such as Nitinol. Still other types of heat expandable stents may be formed with a tin-coated, heat expandable coil. Heat expandable stents are often delivered to the affected area on a catheter capable of receiving a heated fluid. Heated saline or other fluid may be passed through the portion of the catheter on which the stent is located, thereby transferring heat to the stent and causing the stent to expand. However, heat expandable stents have not gained widespread popularity due to the complexity of the devices, unreliable expansion properties and difficulties in maintaining the stent in its expanded state. Still further, it has been found that the application of heat during stent deployment may damage the blood vessel.

In summary, although a wide variety of stents have been proposed over the years for maintaining the patency of a body lumen, none of the existing schemes has been capable of overcoming most or all of the above described shortcomings. As a result, clinicians are forced to weigh advantages against shortcomings when selecting a stent type to use in a particular application. Accordingly, an urgent need exists for a new and improved stent structure that successfully combines the desirable qualities of a balloon expandable stent and a self-expanding stent. It is desirable that such a stent be balloon expandable for providing accurate placement and sizing at a treatment site. It is also desirable that such a stent has sufficient radial strength to maintain patency of the lumen while subjected to substantial external forces. It is also desirable that such a stent be crush-recoverable, such that the stent returns to its deployed state in the event that the stent becomes crushed or pinched. It is also desirable that such a stent be provided with an effective constraining mechanism for holding the stent in the collapsed condition during delivery. It is also desirable that such a stent be configured to exhibit little or no longitudinal foreshortening during radial expansion. It is also desirable that such a stent be sufficiently flexible along the longitudinal axis to conform to the curved shape of a body lumen. It is also desirable that such a stent has the capability to conform to the interior of the body lumen. The present invention addresses these needs.

SUMMARY OF THE INVENTION

Preferred embodiments of the present invention relate to an improved intraluminal stent that is both crush-recoverable and balloon expandable. During use, the stent provides a high radial strength and tunable (adaptable) surface coverage, thereby yielding a device that can be precisely placed in a blood vessel while maintaining the patency of the vessel under a wide variety of conditions. When formed of a superelastic or shape memory material, the stent provides a device that returns to its deployed (i.e., expanded) condition in the event that external pressures cause the stent to temporarily deform inward. Further still, the stent is preferably provided with a constraining mechanism configured to hold the stent in the undeployed (i.e., collapsed) condition during delivery, thereby further facilitating deployment and precise placement of the stent at the treatment site. In an advantageous feature, the constraining mechanism is integrated into the stent structure, thereby eliminating the need for pins, sheaths or other separate components during delivery to the treatment site.

In one preferred embodiment, a balloon expandable crush-recoverable stent comprises a tubular member including a series of slidably interconnected elements fabricated from a shape-memory material. The interconnected elements are configured for allowing the tubular member to be adjusted from a collapsed diameter to an expanded diameter without requiring any substantial material deformation of the interconnected elements. In one variation, the stent further comprises a locking mechanism configured for providing mono-directional expansion and maintaining the tubular member in the expanded diameter after deployment at a treatment site. In another variation, the stent comprises a constraining mechanism configured for maintaining the tubular member in the collapsed diameter until released by radial expansion of an inflatable balloon during deployment at a treatment site. In another variation, a balloon catheter may be included with the stent for providing a stent delivery system.

In an advantageous feature, preferred stent embodiments according to the present invention allow precise sizing, while also allowing for deployment at relatively low inflation pressures. Preferred embodiments advantageously provide the necessary qualities for all stent applications including biliary, coronary, carotid, superficial femoral and popliteal arteries or even veins. Because the stent includes a constraining mechanism that is integrated into the stent structure, the stent does not require a retractable sheath. However, a sheath may be used for additional protection during delivery to the treatment site. When a sheath is used, it is preferably formed from a very thin flexible material.

In another preferred embodiment, a balloon expandable crush-recoverable stent comprises a flat sheet fabricated from a shape-memory material. The flat sheet may be rolled into a cylindrical configuration to provide a tubular member, the tubular member being adjustable from a collapsed diameter to an expanded diameter without requiring any substantial plastic deformation of the flat sheet. The tubular member comprises a locking mechanism configured for providing mono-directional expansion and maintaining the tubular member in the expanded diameter after deployment at a treatment site. The tubular member also comprises a constraining mechanism configured for maintaining the tubular member in the collapsed diameter until released by radial expansion of an inflatable balloon during deployment at a treatment site.

In another preferred embodiment, a balloon expandable crush-recoverable stent comprises a series of pivotally connected links fabricated from a shape-memory material. The pivotally connected links being configured to provide a tubular member that is adjustable from a collapsed diameter to an expanded diameter by pivoting movement of the links. A locking mechanism is provided such that the pivoting links are held in the open position for maintaining the tubular member in the expanded diameter after deployment at a treatment site. A constraining mechanism is also provided such that the pivoting links are held in the closed position for maintaining the tubular member in the collapsed diameter until released by radial expansion of an inflatable balloon during deployment at a treatment site.

In another preferred embodiment, a expandable stent comprises a series of slidably interconnected elements fabricated from a biocompatible material. The interconnected elements are configured to provide a tubular member that is adjustable from a collapsed diameter to an expanded diameter without requiring any substantial material deformation of the elements. The stent further comprises a locking mechanism configured for maintaining the tubular member in the expanded diameter after deployment at a treatment site. The stent also comprises a constraining mechanism disposed along the interconnected elements for maintaining the tubular member in the collapsed diameter until released by radial expansion of an inflatable balloon during deployment at a treatment site.

In another preferred embodiment, an expandable stent comprises at least first and second expandable modules. Each of the expandable modules forms a substantially tubular member and is adjustable from a collapsed condition to an expanded condition. A flexible coupling portion is provided for coupling the first and second expandable modules together. A constraining mechanism is provided along at least one of the first and second expandable modules for maintaining the stent in the collapsed condition during delivery to a treatment site. In an advantageous feature of this embodiment, each of the expandable modules is substantially independently expandable. Accordingly, each of the expandable modules may be expanded to precisely conform to the diameter of the body lumen at its particular location along a treatment site. Therefore, this embodiment is well suited for use in body lumens having a varying internal diameter.

In another preferred embodiment, an expandable stent for supporting a blood vessel comprises a tubular member fabricated from a biocompatible material. The tubular member has a first end portion and a second end portion and is configured for expansion from a collapsed diameter to an expanded diameter. The tubular member includes a central region disposed between the first end portion and the second end portion. A locking mechanism is provided for maintaining the tubular member in the expanded diameter after deployment at a treatment site. A constraining mechanism is provided for maintaining the tubular member in the collapsed diameter until released by radial expansion of an inflatable balloon during deployment at a treatment site. In this embodiment, at least a portion of the central region of the tubular member is formed with a substantially impermeable wall. The impermeable wall is well suited for providing enhanced support along a selected segment of a blood vessel, such as along an aneurysm. In one variation, a portion of the wall may be formed with an opening for allowing blood to flow through the wall and into a side branch vessel.

In another preferred embodiment, a balloon expandable crush-recoverable stent comprises first and second flat sheets that are formed into first and second rows of radial elements. The sheets are configured such that the respective radial elements in the first and second sheets are slidably interconnected to provide a series of expandable tubular modules. Each of the expandable modules may be expanded to a different diameter for conforming to the shape of a body lumen.

In another preferred embodiment, a balloon expandable crush-recoverable stent includes first and second flexible members, each member extending along the longitudinal axis of the stent. The first and second flexible members are slidably interconnected along a plurality of points and are configured to provide at least a portion of a tubular member that is expandable from a collapsed condition to an expanded condition.

In another preferred embodiment, a balloon expandable stent comprises at least two substantially flat elements that are rolled into a cylindrical configuration to provide a tubular member. Each of the flat elements forms a portion of a circumference of the tubular member. The flat elements are slidably interconnected for allowing the tubular member to expand from a collapsed diameter to an expanded diameter without any substantial plastic deformation of the elements. In this embodiment, an expandable sheath is disposed over the tubular member. The expandable sheath is configured to expand during deployment of the stent at a treatment site.

In yet another preferred embodiment, a stent delivery system comprises an elongate catheter with an inflatable balloon disposed along a distal end portion thereof. A balloon expandable stent is disposed along the outer surface of the inflate balloon. If desired, an adhesive or other material may be used to ensure that the stent is securely held on the surface of the balloon. The stent comprises a tubular member including a series of substantially non-deforming slidably interconnected elements. The stent preferably includes a constraining mechanism for holding the stent in the collapsed condition during delivery to the treatment site. Furthermore, the stent preferably includes a ratcheting mechanism for allowing the stent to expand while inhibiting recoil from the expanded condition. The stent is preferably fabricated from a shape memory material to provide a crush-recoverable structure. As a result, the deployed stent advantageously returns to its expanded diameter after undergoing plastic deformation.

In yet another preferred embodiment, a method for treating a vessel at a treatment site comprises providing an elongate catheter having an inflatable balloon disposed along a distal end portion thereof. An expandable stent is disposed over the inflatable balloon for delivery to the treatment site. The expandable stent is formed from a plurality of substantially non-deforming interconnected elements. The stent preferably includes a constraining mechanism for holding the stent in the collapsed condition during delivery to the treatment site. As the balloon is inflated at the treatment site, the interconnected elements slide apart from each other along the surface of the balloon, thereby causing the diameter of the stent to adjust from a collapsed condition to an expanded condition. Accordingly, in an advantageous feature, the expanded diameter of the stent can be precisely controlled by inflation of the balloon. The stent further comprises a locking mechanism configured for providing mono-directional expansion and thereby maintaining the tubular member in the desired expanded diameter after deployment at the treatment site.

In yet another preferred embodiment, a balloon expandable crush-recoverable stent comprises first and second expandable modules, wherein each module comprising a series of slidably interconnected elements fabricated from a shape-memory material. The interconnected elements are configured for allowing the module to be adjusted from a collapsed diameter to an expanded diameter. A locking mechanism is disposed on each of the first and second expandable modules. The locking mechanism is configured such that the interconnected elements are slidable in only one direction for maintaining the expandable module in the expanded diameter. A constraining mechanism is disposed on each of the first and second expandable modules. The constraining mechanism is configured to maintain the respective expandable module in the collapsed diameter until released by radial expansion of an inflatable balloon during deployment at a treatment site. A flexible coupling portion is provided for coupling the first and second expandable modules together in a manner wherein each of the expandable modules is substantially independently expandable.

BRIEF DESCRIPTION OF THE DRAWINGS

FIG. 6A is a plan view illustrating an alternative structure of a radial element that may be interconnected with similar structures to form a balloon expandable crush-recoverable stent.

FIG. 6B is a plan view illustrating slidably interconnected radial elements of the type illustrated in FIG. 6A which are in the collapsed condition.

FIG. 6C is a plan view illustrating slidably interconnected radial elements of the type illustrated in FIG. 6A which are locked-out in the expanded condition.

FIG. 7A is a plan view illustrating another alternative structure of a radial element that may be interconnected with similar structures to form a balloon expandable crush-recoverable stent.

FIG. 7B is a plan view illustrating slidably interconnected radial elements of the type illustrated in FIG. 7A which are in the collapsed condition.

FIG. 7C is a plan view illustrating slidably interconnected radial elements of the type illustrated in FIG. 7A which are locked-out in the expanded condition.

FIG. 25 illustrates another variation of a balloon expandable stent wherein an expandable sheath is disposed over the expandable stent structure.

DETAILED DESCRIPTION OF THE PREFERRED EMBODIMENT

Figure 1:
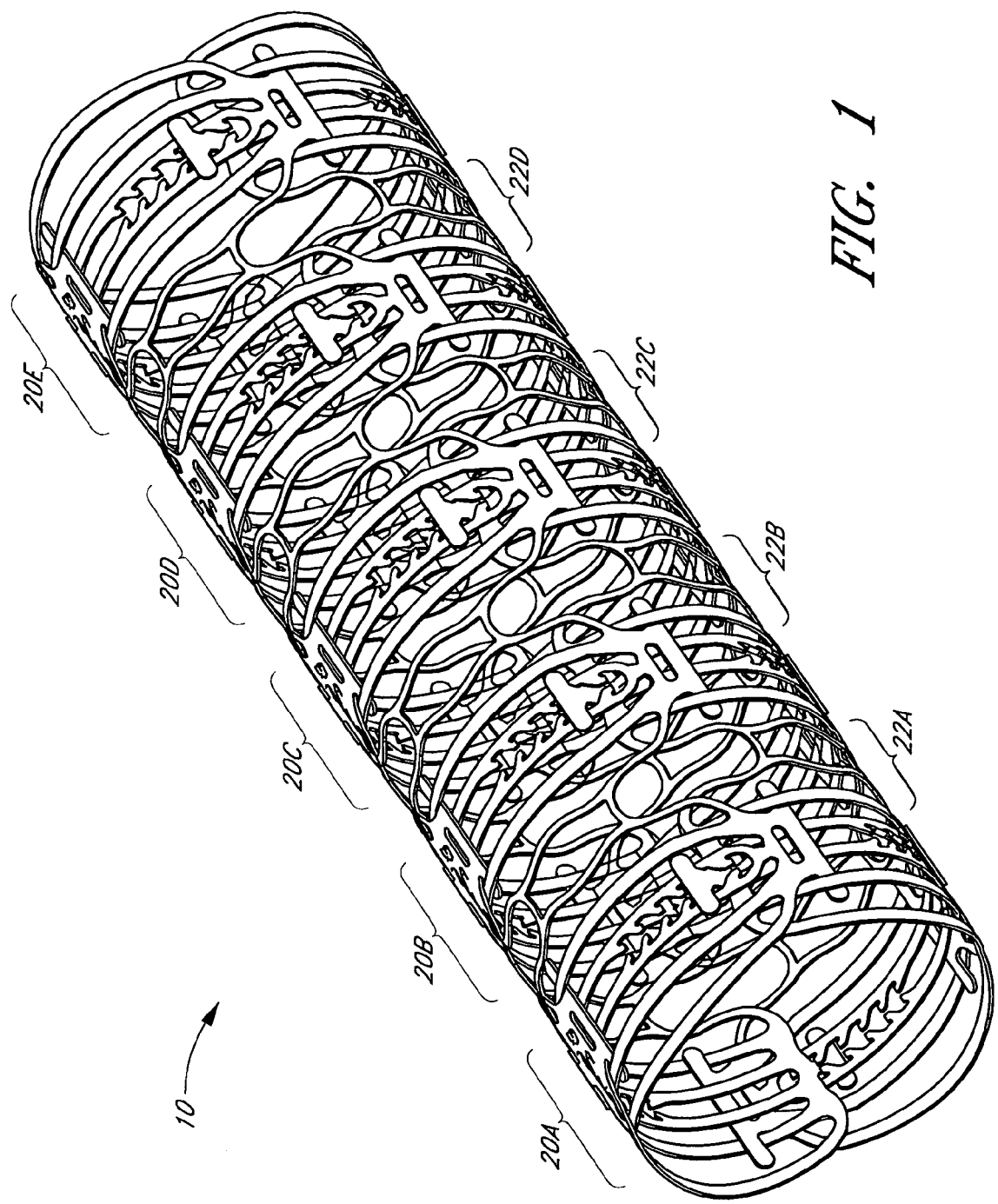
FIG. 1 is a perspective view illustrating a balloon expandable crush-recoverable stent according to one preferred embodiment of the present invention.

Preferred embodiments of the present invention provide a radially expandable stent used to open, support or expand a body passageway. Embodiments of the stent are preferably fabricated from a bio-compatible, shape-memory material to provide the stent with a crush-recoverable structure. In the following description of the present invention, the term "stent" may be used interchangeably with the term "prosthesis" and should be interpreted broadly to include a wide variety of devices configured for supporting a segment of a body passageway. Furthermore, it should be understood that the term "body passageway" encompasses any lumen or duct within a body, such as those described herein, as well as any other artery, vein, or blood vessel. Still further, it should be understood that the term "shape-memory material" is a broad term that includes a variety of known shape memory alloys, such as nickel-titanium alloys, as well as any other materials that return to a previously defined shape after undergoing substantial plastic deformation.

In one preferred embodiment of the present invention, the assembled stent generally comprises a tubular member having a length in the longitudinal axis and a diameter in the radial axis sized for insertion into the body lumen. The tubular member is preferably formed with a "clear through-lumen," which is defined as having little or no structure protruding into the lumen in either the collapsed or expanded condition. Furthermore, the tubular member preferably has smooth marginal edges to minimize the trauma of edge effects on the body lumen. Furthermore, the tubular member is preferably thin-walled and sufficiently flexible to facilitate delivery through tortuous vasculature to small vessels. The thin walled structure advantageously minimizes turbulence, and the associated risk of thrombosis, in the blood flow through the lumen. Those skilled in the art will appreciate that the thin profile of the deployed tubular member may also advantageously facilitate rapid endothelialization of the stent. It will also be appreciated that the length and diameter of the tubular member may vary considerably according to the desired application without departing from the scope of the invention.

Embodiments of an intraluminal stent according to the present invention are preferably provided with a series of interconnected "slide and lock elements" generally referred to herein as "radial elements." The radial elements are slidably interconnected in a manner wherein the stent exhibits ratcheting, mono-directional expansion during deployment. In addition, one or more radial element is preferably provided with a constraining mechanism for resisting stent expansion. Accordingly, the constraining mechanism advantageously allows the stent to be securely held in the collapsed condition during delivery through the patient's vasculature to the treatment site.

An expandable member, such as an inflatable balloon, is preferably used to deploy the stent at the treatment site. As the balloon is expanded, the radial force of the balloon overcomes the initial resistance of the constraining mechanism, thereby allowing the stent to expand. As the balloon is inflated, the radial elements slide with respect to each other along the surface of the balloon until the stent has been expanded to a desired diameter. The radial elements are preferably configured to provide a ratcheting effect such that the stent is maintained (i.e., "locked-out") in the expanded diameter after the balloon is deflated and removed from the body passage.

The stent preferably comprises at least one expandable module, which consists of a series of sliding and locking radial elements. Preferably, a series of similar expandable modules are connected along the longitudinal axis via flexible coupling portions. Each radial element within a module is preferably a discrete, unitary structure that does not stretch or otherwise exhibit any substantial permanent deformation during stent deployment. More particularly, the structure (e.g., radial element) may flex or bend; however, unlike conventional balloon expandable stents, no substantial plastic deformation of the element is required during expansion of the stent from a collapsed diameter to an expanded diameter. Elements of this type are generally referred to herein as "non-deforming elements." Accordingly, the term "non-deforming element" in intended to generally describe a structure that substantially maintains its original dimensions (i.e., length and width) during deployment of the stent. Each radial element is preferably formed as a flat sheet that is cut or otherwise shaped to provide a slide and lock mechanism.

Due to the arrangement of the sliding and locking interconnection, adjacent radial elements may slide circumferentially apart from one another, but are substantially prevented from sliding circumferentially toward one another. Accordingly, the stent may be radially expanded from a small diameter to a large diameter with very little recoil after deployment. As will be apparent from the following detailed description, the amount of recoil can be customized for the application by adjusting the size and the spacing between the teeth along the deflectable members. Preferably, the stent is configured to exhibit recoil after deployment of less than about 5%.

Preferred embodiments of the intraluminal stent provide a substantially non-deforming, crush-recoverable stent structure with excellent radial strength that can be securely held in the collapsed condition and then expanded at the treatment site using an inflatable balloon. Until now, none of the existing stent types has successfully combined an inflatable balloon with a stent formed from a shape memory material to provide a stent having most or all of the desired features for a wide variety of applications. For example, U.S. Pat. No. 6,179,878 to Duerig discloses a composite stent device comprising a shape memory alloy stent sleeve that is treated to exert an outward force on a body lumen. During delivery, an outer restraint sleeve restricts the maximum transverse dimension to which the stent sleeve can expand outwardly. During deployment at a treatment site, the balloon is inflated such that the outer restraint sleeve is expanded plastically, thereby allowing the stent to expand. However, this stent type may not have adequate radial strength for many applications and imposes an undesirable chronic outward stress on the vessel wall. As discussed above, it has been found that a chronic outward stress may damage the vessel wall and may lead to restenosis. Furthermore, the stent may lack sufficient flexibility during delivery to the treatment site and can be cumbersome to utilize. Accordingly, as will be described in more detail below, the present invention provides a substantial improvement over the existing state of the art by providing a balloon expandable, crush-recoverable stent having a desirable combination of features which has not been heretofore available.

With reference now to FIG. 1, for purposes of illustration, one preferred embodiment of an intraluminal stent 10 is illustrated in the expanded condition. The stent 10 comprises, generally, a plurality of expandable modules 20A-20E interconnected by flexible coupling portions 22A-22D. Each module comprises one or more radial elements that are slidably interconnected for allowing the stent to expand without any stretching or substantial material deformation of the individual elements. In an advantageous feature, each individual module (e.g., module 20A) has the ability to radially expand independently of the other modules (e.g., modules 20B-20E). Accordingly, the diameter of the deployed stent may vary along the longitudinal axis. As a result, the stent may be accurately and precisely expanded to match the particular shape of the vessel at the treatment site. When used for direct stenting, a balloon may be used to expand the modules, either together or individually, while simultaneously pushing against the vessel wall until the desired diameters are achieved.

Figure 2:
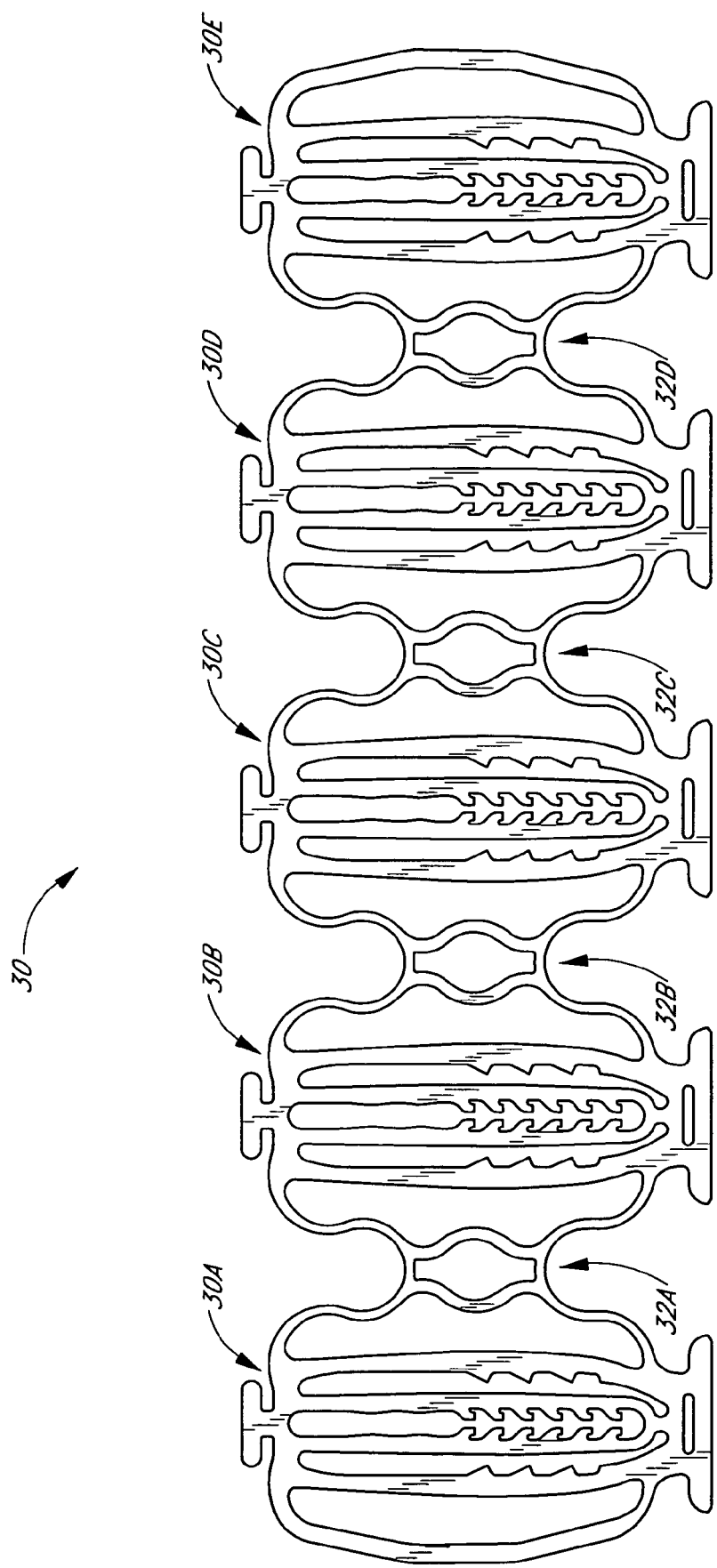
FIG. 2 is a plan view illustrating a row of radial elements which forms a portion of the stent of FIG. 1.

With reference now to FIG. 2, a portion of the stent is depicted as a substantially flat sheet having contoured edges and cut-away portions. The illustrated sheet has been shaped to provide a single row 30 of five radial elements 30A-30E. Similar rows of radial elements are slidably interconnected to form the cylindrical stent 10 of FIG. 1. In the stent embodiment of FIG. 1, four rows, each identical to the row 30 shown in FIG. 2, are slidably interconnected. However, in an advantageous feature of the illustrated embodiment, the number of interconnected rows in the assembled stent may be selected to suit the particular application. Accordingly, the row 30 of radial elements 30A-30E may be interconnected with any number of similar rows to provide a stent having a desired diameter. Furthermore, during manufacture, it will be appreciated that the row 30 may be shaped with any length, such as by varying the number and width of the radial elements.

When assembled, each radial element 30A-30E in the row 30 forms a portion of an independently expandable module 20A-20E of FIG. 1. In an important feature, it will be appreciated that the distance between radial element 30A and element 30E remains substantially constant during deployment and therefore little or no foreshortening of the stent occurs during deployment. Furthermore, it will be appreciated that each row 30 of radial elements 30A-30E is a substantially non-deforming structure which allows the stent to expand through slidable interconnections, rather than through material deformation.

With continued reference to FIGS. 1 and 2, spring-like linkage elements 32A-32D are configured for connecting radial elements 30A-30E together for providing the stent 10 with excellent longitudinal flexibility. Accordingly, the stent is provided with the ability to bend for conforming to a curved body lumen. The linkage elements 32A-32D form a portion of the flexible coupling portions 22A-22D of FIG. 1. When assembled, the flexible coupling portions 22A-22D are preferably substantially decoupled from the functioning slide and lock mechanisms of the expandable modules 20A-20E. Furthermore, the flexible coupling portions 22A-22D are configured with sufficient flexibility to allow each of the individual modules to expand in a substantially independent manner. Accordingly, the flexible coupling portions 22A-22D advantageously allow the stent to achieve a high degree of flexibility without compromising the functionality and reliability of the expandable modules. In an advantageous feature of the present invention, the independent nature of the modules and flexible coupling portions provides excellent design flexibility and allows for various combinations of features that can be configured for suiting a particular need. Still further, the linkage elements may be advantageously configured to provide the desired combination of axial strength and flexibility.

Figure 3:
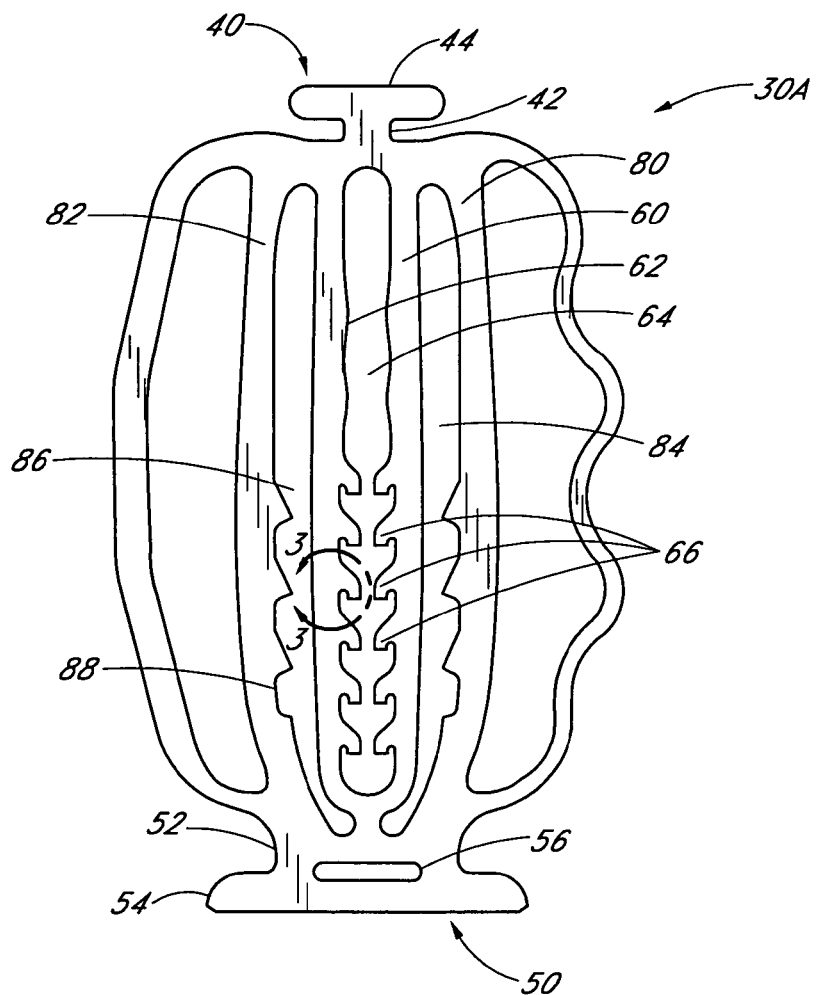
FIG. 3 is a plan view illustrating a single radial element that forms a portion of the row of FIG. 2.
Figure 3A:
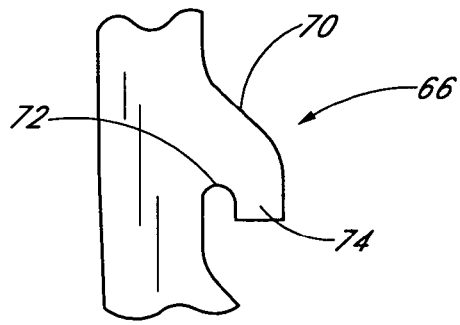
FIG. 3A is an enlarged view of a tooth from the radial element of FIG. 3.

With reference now to FIG. 3, a single radial element 30A is illustrated in isolation for ease of description. The radial element 30A comprises a variety of mechanical features including a first engagement member in the form of a locking tab 40 at a first end and a second engagement member in the form of a hold-down tab 50 at a second end. The locking tab 40 is provided with a thin neck portion 42 and a wide head portion 44. The hold-down tab 50 is also provided with a thin neck portion 52 and a wide head portion 54. A slot 56 is provided along the neck portion 52 of the hold-down tab 50 to provide the head portion 54 with additional bending flexibility. The radial element 30A further comprises first and second deflectable members 60, 62 spaced apart by a longitudinal gap 64. The deflectable members 60, 62 are each provided with a plurality of angled teeth 66 disposed along the gap 64 in an opposing configuration. FIG. 3A is an enlarged view illustrating one preferred shape of an angled tooth 66 provided along an inner edge of one deflectable member 62. The tooth 66 has a body 74 with and angled side 70 and a capturing side 72, which is provided between the body 74 and the deflectable member 62. With reference again to FIG. 3, the radial element 30A is further provided with first and second containment members 80, 82. The containment members are disposed outside the deflectable members 60, 62 such that first and second gaps 84, 86 are located between the containment members 80, 82 and the deflectable members 60, 62.

In preferred embodiments, one or more capturing portions in the form of recesses 88 are provided along each of the containment members 80, 82. In the illustrated embodiment, the recesses 88 are provided along the inner edges of the containment members 80, 82. The recesses are sized and shaped for receiving and capturing the hold-down tab 50 from an interconnected radial element. When the hold-down tab 50 is captured in the recesses 88, movement between adjacent interconnected radial elements is resisted such that the stent is "held-down" (i.e., constrained) in a collapsed condition. Accordingly, the recesses 88 are configured for resisting undesirable expansion of the stent during delivery to the treatment site. The illustrated embodiment is provided with a number of recesses, such that the stent may be constrained at a variety of different diameters during delivery. In preferred embodiments, the recesses 88 are disposed along the containment members 80, 82 in a location such that movement between interconnected radial elements is resisted only when the stent is in the collapsed condition.

In another advantageous feature, embodiments provided with a constraining mechanism may be delivered to a treatment site without a delivery sheath. However, if desired for a particular application, embodiments of the present invention may be used with a delivery sheath to further constrain the stent in the collapsed condition and to protect the inner wall of the vessel during stent delivery. For example, a retractable delivery sheath may be configured for enclosing the stent during delivery. After the treatment site is reached, the sheath is withdrawn to expose the stent. In another alternative configuration, a vessel sheath may be used with preferred stent embodiments, such as, for example in a vessel graft.

Figure 4B:
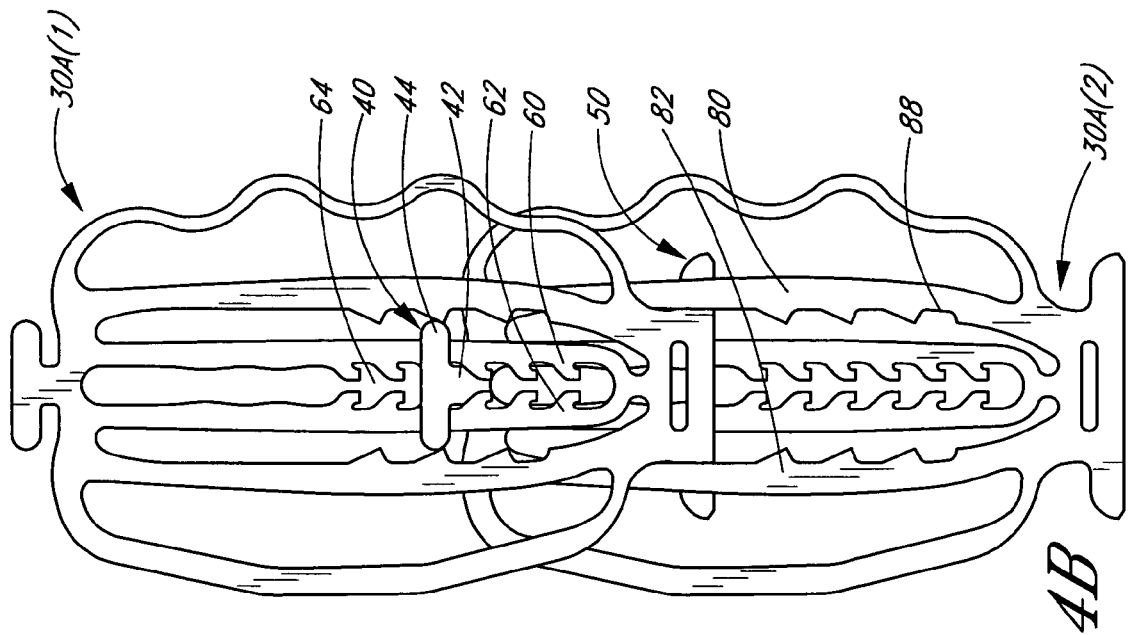
FIG. 4B is a plan view illustrating the two slidably interconnected radial elements of the type illustrated in FIG. 2 which are locked-out in the expanded condition.
Figure 4A:
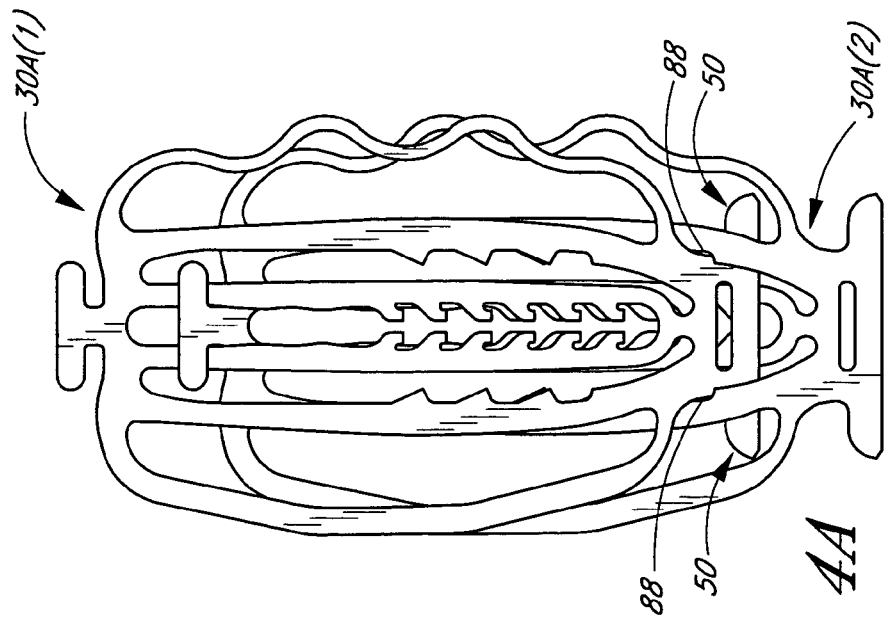
FIG. 4A is a plan view illustrating two slidably interconnected radial elements of the type illustrated in FIG. 2 which are constrained in the collapsed condition.

With reference now to FIGS. 4A and 4B, the slide and lock relationship between two identical interconnected radial elements 30A(1), 30A(2) is illustrated. For ease of description, the radial elements are shown lying flat in a plan view. However, during use, each of the radial elements will be curved to form a portion of the circumference of the stent. With particular reference now to FIG. 4A, the overlapping radial elements are illustrated in the collapsed configuration wherein the hold-down tab 50 of radial element 30A(1) is held within the recesses 88 of radial element 30A(2). The cooperation between the hold-down tab and the recesses provides a constraining mechanism for resisting slidable movement between the radial elements. However, as described above, the constraining mechanism is configured such that, under sufficient radial force (e.g., during expansion of the balloon), the hold-down tab 50 is releasable from the recesses 88. When released, the hold-down tab is allowed to slide along the containment members 80, 82. With reference now to FIG. 4B, the radial elements are illustrated in the expanded condition wherein the hold-down tab 50 of radial element 30A(1) has been released from the recesses 88 of radial element 30A(2) for allowing the radial elements to slide apart.

With continued reference now to FIGS. 4A and 4B, the gap 64 between the deflectable members 60, 62 of radial element 30A(1) is sized for receiving the locking tab 40 from radial element 30A(2). In particular, the neck portion 42 of the locking tab 40 from radial element 30A(2) extends through the gap 64, with the wider head portion 44 located above the deflectable members 60, 62 of radial element 30A(1). The hold-down tab 50 of radial element 30A(1) is slidably disposed over the deflectable members 60, 62 of radial element 30A(2) and beneath the containment members 80, 82 of radial element 30A(2). During expansion, the interconnections between the hold-down tab 50 and the containment members 80, 82 advantageously hold the radial elements in a desirable slidable relationship. As a result, this feature advantageously maintains the deflectable members in a secure position and ensures a proper interaction between the locking tabs 40 and the deflectable members 60, 62.

With particular reference to FIG. 4B, the opposing sets of teeth 66 along the deflectable members 62, 64 are angled such that the neck portion 42 of the locking tab 40 of radial element 30A(2) is capable of sliding between the opposing teeth 66 during expansion of the module. During the expansion, the locking tab 40 contacts the angled sides of the teeth which, in turn, causes the deflectable members 60, 62 to deflect outward and apart. The deflection (i.e., spreading apart) of the deflectable members 60, 62 widens the gap 64 to a sufficient width wherein the neck portion 42 of the locking tab 40 may slidably pass through while the wider head portion 44 rides along the top of the deflectable members 60, 62.

Due to the shape of the teeth, the neck portion 42 of the locking tab 40 is prevented from moving back through the gap 64, such as when a radially compressive force is applied to the module. More particularly, when the locking tab 40 contacts the capturing sides 72 of teeth 66, the deflectable members 60, 62 are not caused to deflect outward. As a result, the locking tab 40 is prevented from passing between the opposing teeth 66. Accordingly, the relationship between the deflectable members 60, 62 and the locking tab 40 advantageously provides mono-directional (i.e., ratcheting) expansion for locking the module in the expanded condition after deployment in a body lumen.

Preferably, a plurality of teeth is provided along the deflectable members such that the radial elements may be expanded and locked at any desired diameter. Accordingly, the invention allows for excellent sizing, preferably allowing for increments in the range of about 0.05 to 0.20 mm. Due to the close spacing of the teeth, the mono-directional lockout configuration of the present invention allows the stent to be expanded with very little recoil, thereby minimizing the need for over expansion during initial deployment. Furthermore, in contrast to typical deformable stents (e.g., conventional balloon-expandable stents), there is no elastic region of deformation to cause the stent to recoil after the balloon is deflated. Accordingly, in preferred embodiments of the present invention, stent recoil after deployment (i.e., the collapse from an expanded diameter) is less than about 5%. Therefore, after expansion at the treatment site, the stent will remain well positioned along the vessel wall without the need for harmful and damaging over-expansion.

Although the sets of opposing teeth are illustrated as being located along the inside of the deflectable members, it will be apparent to those skilled in the art that the location and shape of the teeth may be reconfigured without departing from the scope of the invention. For example, in one alternative embodiment, the teeth may be provided along the outside of the deflectable members in place of, or in addition to, the illustrated teeth. Still further, it will be appreciated that, although angled teeth and locking tabs are illustrated for providing mono-directional expansion, any other structure capable of allowing relative slidable movement of radial elements in only one direction is contemplated to be within the scope of the invention.

With reference now to FIGS. 1-4B, one preferred method of deploying the stent 10 in a blood vessel will be described in greater detail. Although the method of use is described with respect to a stent having multiple expandable modules wherein each module comprises multiple radial elements, the method may also be applied to a variety of alternative embodiments that fall within the scope of the present invention.

First, a catheter is provided wherein an inflatable balloon, such as an angioplasty balloon, is provided along a distal end portion. One example of a balloon catheter for use with a stent is described in U.S. Pat. No. 4,733,665 to Palmaz, which is incorporated by reference herein. An expandable stent 10 of the type illustrated in FIG. 1 is disposed over the inflatable balloon in a collapsed condition for delivery to a treatment site. The stent 10 preferably comprises a series of independently expandable modules 20A-20E which are formed from interconnected rows 30 of radial elements 30A-30E wherein each radial element is formed with a hold-down tab 50 and recesses 88. The recesses 88 are shaped for capturing the hold-down tab of the adjacent radial element. If desired, a sheath or other cover may be disposed over the stent to protect the blood vessel during delivery.

A location in the patient's body is selected for deployment of the stent 10. During delivery, while the stent is disposed along the catheter, the hold-down tabs 50 of each radial element are securely held within the recesses 88 of the adjacent radial element. Accordingly, the stent is maintained in the collapsed condition as the catheter is advanced through the patient's vasculature. After reaching the treatment site, the inflatable balloon is selectively expanded to a desired diameter, thereby producing a radial force which causes the hold-down tabs 50 to become released from the recesses 88. As the hold-down tabs are released, the radial elements become slidable relative to one another. Accordingly, the stent may be selectively and precisely expanded in diameter without any substantial material deformation of stent components. As the radial elements slide along each other during expansion, the locking tabs 40 enter the opposing teeth 66 of the interconnected radial elements for maintaining the stent in the expanded condition.

When the desired diameter is achieved, the inflatable balloon is deflated and removed. At this time, the locking tabs 40 settle securely back into the teeth 66 to hold the modules 20A-20E in the expanded condition, as shown in FIG. 1. Preferably, a large number of teeth are provided such only a small amount of movement is required before the locking tabs are securely held in place by into the teeth. Therefore, the module may be expanded to a precise diameter with very little recoil. In alternative methods, this process may be repeated for each module individually or may be achieved for all modules simultaneously through the expansion of a single expandable member. Still further, a plurality of balloons may be provided along a catheter, wherein each module is disposed along a different balloon, thereby allowing for simultaneous and independent expansion. After the stent is properly deployed, the balloon catheter is removed from the patient's vasculature.

As discussed above, embodiments of the stent are preferably formed, at least in part, from a shape memory alloy. Therefore, each of the individual modules exhibits crush-recovery after deformation. Because the stent is crush-recoverable and exhibits excellent longitudinal flexibility, the stent may be effectively utilized in areas of the body where there are significant torsional or flexion/extension stresses (e.g., superficial femoral artery and popliteal artery). Similarly, the stent may be used in areas of the body which are vulnerable to external pressures (e.g., superficial femoral artery and carotid artery).

Figure 5B:
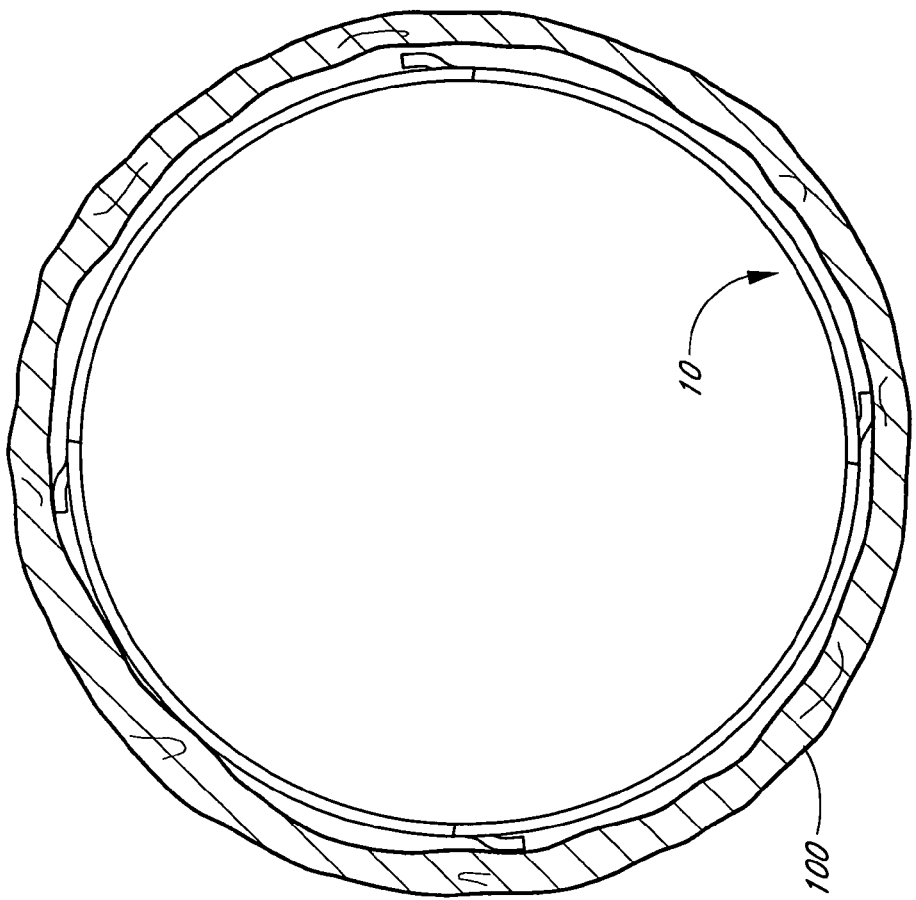
FIG. 5B illustrates the crush-recoverable stent of FIG. 5A after the external pressure has been removed and wherein the stent has returned to its original expanded diameter.
Figure 5A:
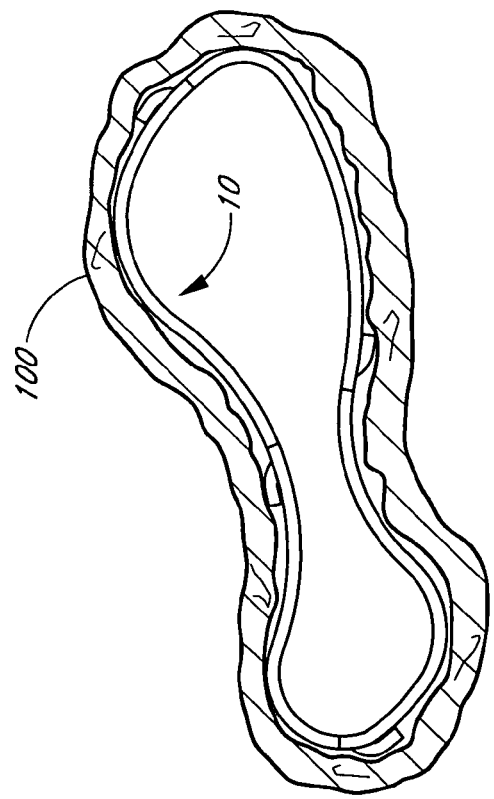
FIG. 5A is an end view of an implanted crush-recoverable stent of the type shown in FIG. 1 wherein an external pressure has caused the stent to temporarily deform inward.

After deployment, an expanded stent may be subjected to non-uniform external pressures that may cause the stent to form a flattened or "half-moon" shape. This occurs since vascular disease is often not uniform and therefore lesions are typically eccentrically shaped with localized irregularities. For purposes of illustration, FIG. 5A illustrates a cross-section view of the stent 10 shown in FIG. 1 according to the present invention deployed within a blood vessel 100. As illustrated, an external pressure along the blood vessel 100 has caused the stent to collapse inward. With reference now to FIG. 5B, the stent 10 is shown after the external pressure has been removed and wherein the stent has returned to the fully expanded condition.

It will be appreciated that crush-recoverability of preferred embodiments is enhanced because the stents have individual radial elements disposed along the circumference for resisting collapse in any one location. Furthermore, in the event that the stent is subjected to large external pressures, the stent construction allows for crush recovery along the entire device. This is a substantial improvement over stent configurations known in the art, which typically exhibit only localized recovery or partial recovery. It will further be appreciated that stents constructed according to the present invention are particularly advantageous over existing stents when exposed to non-uniform, irregular pressures.

Due to the unique combination of features, preferred stents constructed according to the present invention provide a number of advantages over conventional balloon-expandable stents. For example, because preferred embodiments of the stent are expanded using interconnected slide and lock elements, rather than by material deformation of stent components, there is no foreshortening of the stent during expansion. This is a particularly advantageous feature because foreshortening decreases the clinician's ability to precisely place a stent in a blood vessel or other body lumen. Furthermore, in another important advantage, the stent's diameter may be expanded using a relatively low inflation pressure. This feature enhances the clinician's ability to control the deployment of the stent and thereby reduces or eliminates damage to the vessel wall. Still further, as discussed above, it is not necessary to over-dilate the stent during deployment, thereby reducing injury to the vessel. In addition, as discussed above, the deployed stent provides a crush-recoverable structure. Accordingly, in the event that the stent is deformed due to external pressures, the stent returns to its deployed diameter after the pressure is removed. Further still, the stent does not exert a chronic outward stress on the body lumen, nor does the stent exhibit chronic recoil over time. Also, it is not necessary to over-inflate the stent during deployment to compensate for recoil. Due to the ratcheting effect, exact placement and sizing may be achieved. Also, due to the flexible coupling portions, the stent may be delivered through tortuous vasculature to a small vessel. Further still, the modular design is well-suited for creating a stent for a particular application in a cost-effective manner.

Preferred embodiments of the present invention also provide a number of advantages as compared with self-expanding stents. For example, the deployed stent provides a high radial strength that resists deformation under low external pressures and does not produce an undesirable chronic expansion force along the inner wall of the vessel. Furthermore, due to the ratcheting effect of the radial elements (i.e., slide and lock mechanisms), the clinician advantageously maintains excellent control over the position and diameter of the stent during the deployment process. As a result, the stent may be accurately and precisely placed in the vessel without foreshortening or jumping during deployment. Furthermore, the stent requires no substantial deformation of materials during expansion. In yet another advantageous feature, the stent provides excellent longitudinal flexibility due to the flexible coupling portions between the expandable modules. Still further, the stent is provided with smooth interior and exterior surfaces for preventing injury to the vessel and reducing the risk of thrombosis.

In yet another advantageous feature, it will be appreciated that preferred embodiments of the stent may also be used for combination stent/vascular grafts. For example, embodiments of a balloon expandable crush-recoverable stent described above, or alternative stent embodiments manufactured from a non-crush-recoverable material could be advantageously used in combination with a vascular graft material. In an improvement over existing techniques, the expansion characteristics of the improved stent allow the graft to achieve improved radial apposition and permanent positioning without a risk of delaminating or shortening. In the present invention, when the member is expanded, there is no distortion along the longitudinal axis of the member and therefore the length remains substantially constant as the member is expanded.

The ratcheting, slide and lock geometry of preferred stent embodiments also provides several advantages during the treatment of carotid artery atherosclerosis. For example, clinicians typically predilate a carotid artery lesion, such as with a balloon catheter, to push the plaque against the vessel wall before stent placement. A self-expanding stent may then be placed in the artery to help maintain vessel patency. However, a stent constructed according to the present invention advantageously allows for direct stenting of carotid arteries, thereby simplifying the procedure. Furthermore, the stent provides enhanced radial strength for resisting deformation due to external pressures and also provides crush-recoverability in the event that deformation occurs. In addition, the amount of surface coverage can be increased to better stabilize plaque during stenting. Accordingly, preferred embodiments of the present invention combine the desirable features of self-expanding stents and balloon expandable stents to substantially improve the effectiveness of the procedure and reduce the likelihood of plaque embolization during deployment.

Preferred stent embodiments, as described herein, may be formed from a variety of suitable materials. For example, as discussed above, stents is formed of any shape memory material known in the art including, without limitation, nickel-titanium alloys, Nitinol and Elastinite®, for providing a crush-recoverable structure. Alternatively, thermal shape memory polymers or metallic materials may be used to provide a crush-recoverable structure. When thermal memory materials are used, the transition temperature may be set such that the stent is in a collapsed condition at a normal body temperature. However, with the application of heat, such as via a hot balloon catheter or a hot liquid (e.g., saline) perfusion system, the stent expands to assume its final diameter in the body lumen.

Although preferred stent embodiments have been described as being crush-recoverable, those skilled in the art will appreciate that stent constructions according to the present invention may also be formed from a variety of other materials. For example, in alternative embodiments, functional stents with applications not exhibiting substantial crush recovery may be formed of non-super elastic materials, such as 316 stainless steel, tantalum, titanium, tungsten, gold, platinum, iridium, rhodium and alloys thereof or pyrolytic carbon. In still other alternative embodiments, the stents may be formed of a corrodible material, such as, for instance, a magnesium alloy.

In still other preferred embodiments, stents may be formed from biocompatible polymers that are biostable (e.g., non-degrading and non-erodible). Examples of suitable non-degrading materials include, but are not limited to, polyurethane, Delrin, high density polyethylene, polypropylene, and poly(dimethyl siloxane). Further still, the stents may be formed from biocompatible polymers that are bio-resorbable (e.g., bio-erodible or bio-degradable). Bio-resorbable materials are preferably selected from the group consisting of any hydrolytically degradable and/or enzymatically degradable biomaterial. Examples of suitable degradable polymers include, but are not limited to, polyhydroxybutyrate/polyhydroxyvalerate copolymers (PHV/PHB), polyesteramides, polylactic acid, hydroxy acids (i.e. lactide, glycolide, hydroxybutyrate), polyglycolic acid, lactone based polymers, polycaprolactone, poly(propylene fumarate-co-ethylene glycol) copolymer (aka fumarate anhydrides), polyamides, polyanhydride esters, polyanhydrides, polylactic acid/polyglycolic acid with a calcium phosphate glass, polyorthesters, silk-elastin polymers, polyphosphazenes, copolymers of polylactic acid and polyglycolic acid and polycaprolactone, aliphatic polyurethanes, polyhydroxy acids, polyether esters, polyesters, polydepsidpetides, polysaccharides, polyhydroxyalkanoates, and copolymers thereof. Further still, the stents may be formed of a polycarbonate material, such as, for example, tyrosine-derived polycarbonates, tyrosine-derived polyarylates, iodinated and/or brominated tyrosine-derived polycarbonates, iodinated and/or brominated tyrosine-derived polyarylates. For additional information, see U.S. Pat. Nos. 5,099,060, 5,198,507, 5,587,507, 5,658,995, 6,048,521, 6,120,491, 6,319,492, 6,475,477, 5,317,077, and 5,216,115, each of which is incorporated by reference herein. In yet another alternative embodiment, shape-shifting polymers may be used to fabricate stents constructed according to the present invention. Suitable shape-shifting polymers may be selected from the group consisting of polyhydroxy acids, polyorthoesters, polyether esters, polyesters, polyamides, polyesteramides, polydepsidpetides, aliphatic polyurethanes, polysaccharides, polyhydroxyalkanoates, and copolymers thereof. For addition disclosure on bio-degradable shape-shifting polymers, see U.S. Pat. No. 6,160,084, which is incorporated by reference herein. For additional disclosure on shape memory polymers, see U.S. Pat. Nos. 6,388,043 and 6,720,402, each of which are incorporated by reference herein. Additionally the device could be comprised of any number of other polymers. In still other alternative embodiments, metals and polymers may be used to fabricate stent embodiments in a composite, laminate reinforced material, or one that is simply coated with the material.

Stents according to the present invention are preferably formed with thin walls for providing a low crossing profile and for allowing excellent longitudinal flexibility. In preferred embodiments, the wall thickness is about 0.0001 inches to about 0.0250 inches, and more preferably about 0.0010 to about 0.0100 inches, and still more preferably about 0.0018 inches to about 0.0022. However, the wall thickness depends, at least in part, on the selected material. For example, the thickness may be less than about 0.0060 inches for plastic and degradable materials and may be less than about 0.0020 inches for metal materials. More particularly, when a plastic material is used, the thickness is preferably in the range of about 0.0040 inches to about 0.0045 inches. However, a stent having a diameter of about 6 mm, such as for biliary and other peripheral vascular applications, the material thickness is preferably about 0.0018 inches to about 0.0022. The above thickness ranges have been found to provide preferred characteristics through all aspects of the device including assembly and deployment. However, it will be appreciated that the above thickness ranges should not be limiting with respect to the scope of the invention and that the teachings of the present invention may be applied to devices having dimensions not discussed herein.

Preferred methods of fabricating the individual stent elements include, but are not limited to, laser cutting, laser ablation, die-cutting, chemical etching, and stamping and water jet cutting of either tube or flat sheet material. Further one may use plasma etching or other methods known in the art which are capable of producing high-resolution and polished components. Once the base geometry is achieved, the frames can be processed numerous ways. For example, elements can be electropolished and then assembled, or electropolished, coated, and then assembled, or assembled and then electropolished. The current invention is not limited to the means by which stent or stent elements can be fabricated.

The method of manufacture, in some embodiments, depends on the material used to form the stent. Chemical etching provides high-resolution components at relatively low price, particularly in comparison to high cost of competitive product laser cutting. Some methods allow for different front and back etch artwork, which could result in chamfered edges, which may be desirable to help improve engagements of lockouts. In one preferred method of manufacture, the components of the stent may be heat set at various desired diameters. For example, the stent may be set to have a diameter equal to that of the deflated balloon, as deployed, at a maximum diameter, or greater than the maximum diameter. In a preferred embodiment, the stent is heat set at beyond the maximum diameter then built mid diameter than placed over catheter and reverse ratcheted and locked into smaller diameter and onto catheter with positive catch hold down mechanism to achieve a small profile and excellent retention.

With reference now to FIGS. 6A through 6C, a first alternative embodiment of a radial element 130 is illustrated for use with a balloon expandable, crush-recoverable stent constructed according to the present invention. With particular reference to FIG. 6A, the radial element 130 is provided with guide tabs 132, 134 and a locking tab 136 disposed therebetween. With reference now to FIGS. 6B and 6C, the slide and lock relationship between interconnected radial elements 130 (1) and 130(2) is illustrated. The guide tabs 132, 134 of radial element 130(2) ride along first and second containment members 142, 144 of radial element 130(1). The locking tab 136 of radial element 130(2) extends through a gap 150 between first and second deflectable members 146, 148 of radial element 130(1). Hold-down tabs 138, 140 on radial element 130(2) are also provided for holding radial element 130(1) in a desirable slidable arrangement. FIG. 6B illustrates the radial elements in a collapsed condition and FIG. 6C illustrates the radial elements in the expanded condition. After expansion, the locking tab 136 of 130(2) is disposed in the gap between deflectable members 146, 148 of 130(1) and is prevented from collapsing by the teeth of radial element 130(1).

With reference now to FIGS. 7A through 7C, a second alternative embodiment of a radial element 150 is illustrated for use with a balloon expandable, crush-recoverable stent constructed according to the present invention. With particular reference to FIG. 7A, the radial element 150 is provided an upper locking tab 160 and two lower locking tabs 162, 164 disposed underneath. The upper locking tab 160 is configured to extend through a gap 180 between first and second deflectable members 176, 178. The outer edges of the upper locking tab 160 are held beneath first and second containment members 172, 174. In an important feature of this embodiment, teeth 186, 188 are provided along both sides of each of the deflectable members 176, 178. More particularly, the inner teeth 186 engage the upper locking tab and the outer teeth 188 are received in the space between the lower locking tabs 162, 164 and a neck portion of the locking tab 160. With reference now to FIGS. 7B and 7C, radial elements 150(1) and 150(2) are slidably interconnected such that upper locking tab 160 of radial element 150(2) is disposed over deflectable members 176, 178 and under containment members 172, 174. FIG. 7B illustrates the interconnected radial elements in the collapsed condition and FIG. 7C illustrates the interconnected radial elements in an expanded condition. Similarly, the inner teeth of radial element 150(1) engage the locking tab 160 of radial element 150(2) such that the radial elements are held in the expanded condition. Furthermore, the outer teeth of 150(1) engage the tabs 162, 164 to further prevent undesirable collapse.

For purposes of illustrations, certain preferred constraining mechanisms have been illustrated and described above for holding the interconnected radial elements in the collapsed condition. However, it will be appreciated that embodiments of the present invention may be configured with a wide variety of constraining mechanisms for receiving and capturing a portion of an adjacent radial element. For example, in various other embodiments, constraining mechanisms may take the form of catches, bendable tabs, deflectable elements, and adhesive connections.

Figure 8:
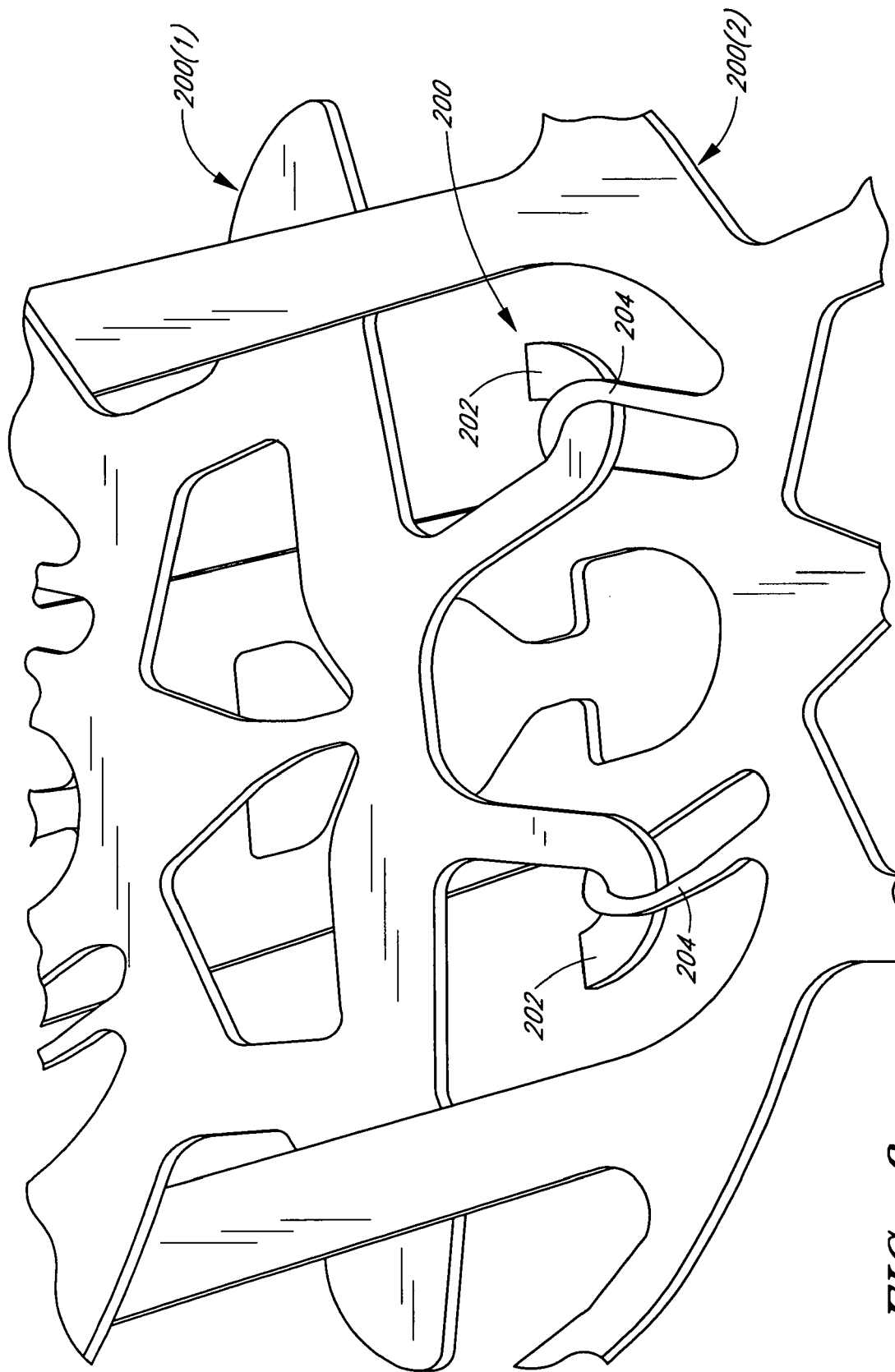
FIG. 8 illustrates an alternative constraint mechanism comprising interconnecting hooks and loops for maintaining the stent in the collapsed condition during stent delivery.

With reference now to FIG. 8, one alternative embodiment of a constraining mechanism 200 generally comprises hooks 202 provided along a first radial element 200(1) which cooperate with loops 204 provided along a second radial element 200(2). The hooks 202 are configured to be sufficiently flexible such that they may be released from the loops 204 under sufficient radial force (e.g., during inflation of the balloon). In an advantageous feature, the flexibility of the hooks can be selected such that the constraining mechanism 200 releases at a particular desired force.

Figure 9:
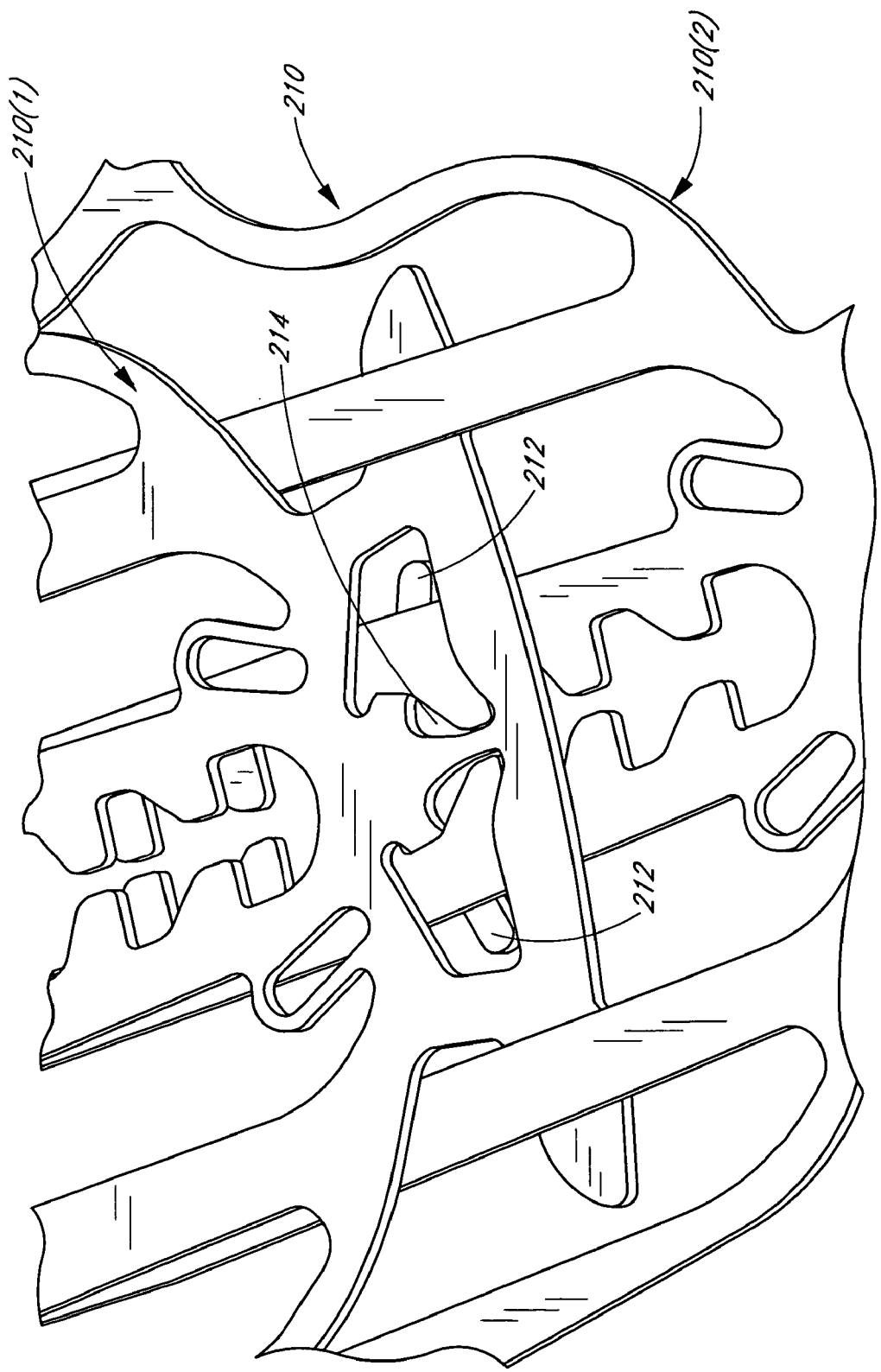
FIG. 9 illustrates another alternative constraint mechanism comprising a deflectable wing for maintaining the stent in the collapsed condition during stent delivery.

With reference now to FIG. 9, another alternative embodiment of a constraining mechanism 210 is illustrated that may be used alone or in combination with other constraining mechanisms. This constraining mechanism 210 generally comprises a wing 212 on a first radial element 210(1) that is held within a gap 214 formed in an adjacent radial element 210(2). The wing 212 is configured to bow or flex by a sufficient amount such that it may be released from the gap 214 under a radial force. In the illustrated embodiment, a plurality of gaps is provided such that the stent may be held-down in a collapsed condition at a variety of different diameters. It will be appreciated that this embodiment, as well as other preferred embodiments described herein, comprises a constraining mechanism that is integrated into the structure of the interconnected radial elements. According, in an advantageous feature, there is no structure to remove or break-away for releasing the stent from the collapsed condition during deployment.

Figure 10:
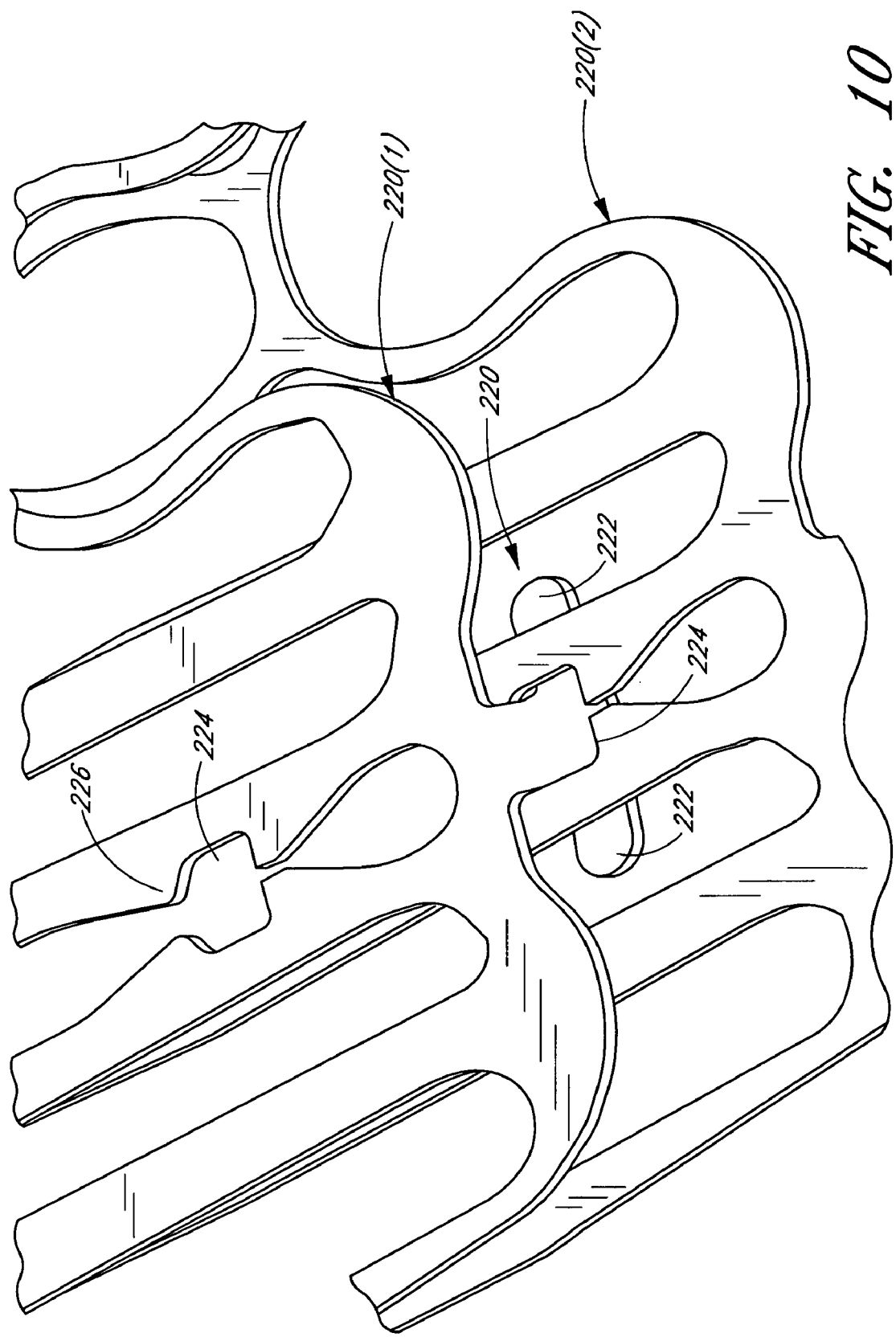
FIG. 10 illustrates yet another alternative constraint mechanism comprising a tab and a gap for maintaining the stent in the collapsed condition during stent delivery.

With reference now to FIG. 10, another alternative embodiment of a constraining mechanism 220 is illustrated wherein a tab 222 on a first radial element 220(1) is received within a gap 224 on a second radial element 220(2). The gap 224 is provided with a neck portion 226 that prevents the tab 222 from sliding out in the absence of force. However, under sufficient radial force, the neck portion 226 of radial element 220(2) bows outward to provide a sufficiently large gap such that the tab 222 of radial element 220(1) may slide there between.

Figure 11A:
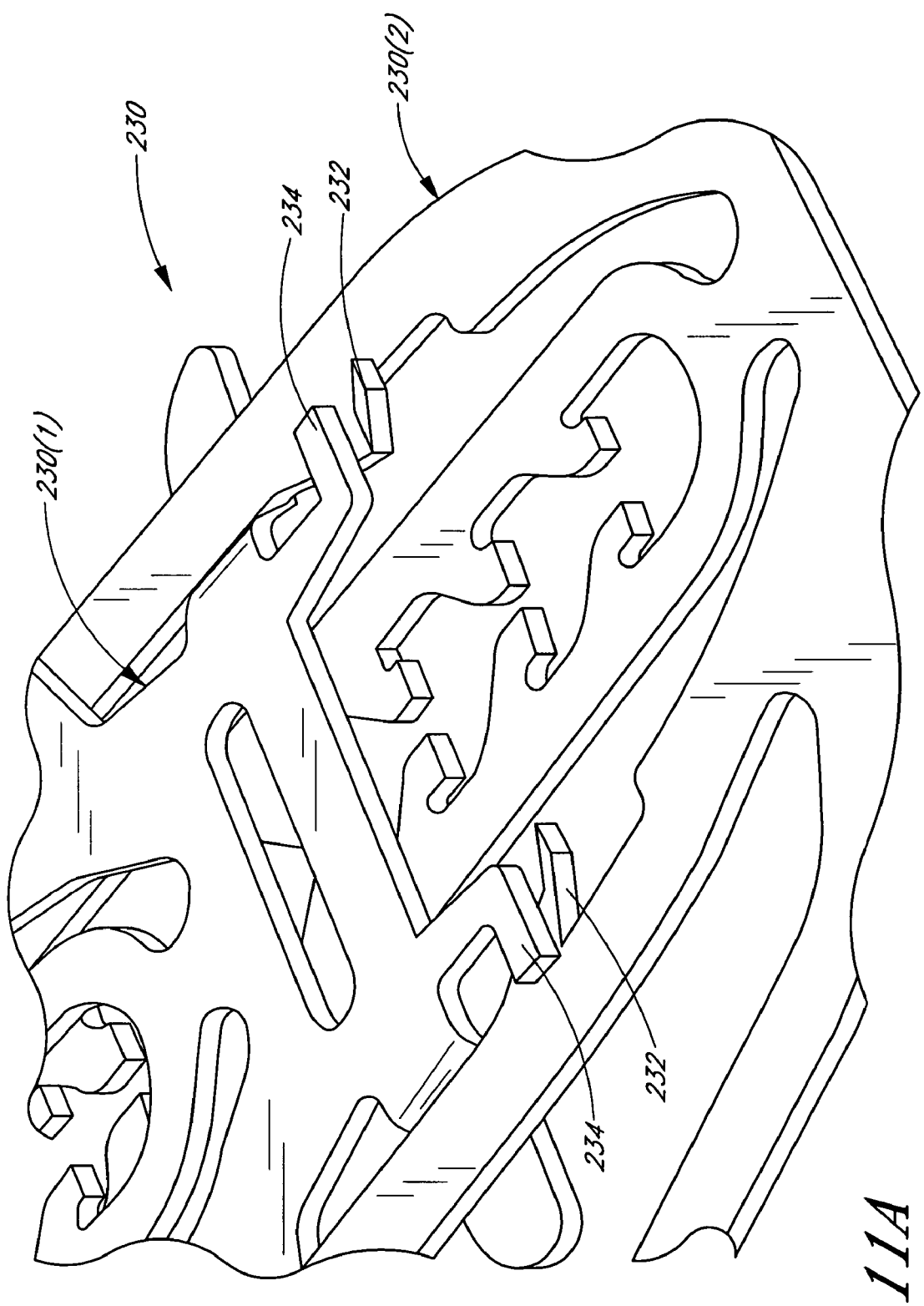
FIG. 11A illustrates yet another alternative constraint mechanism comprising deflectable arms and locks which may be used to maintain the stent in a collapsed condition during stent delivery.
Figure 11B:
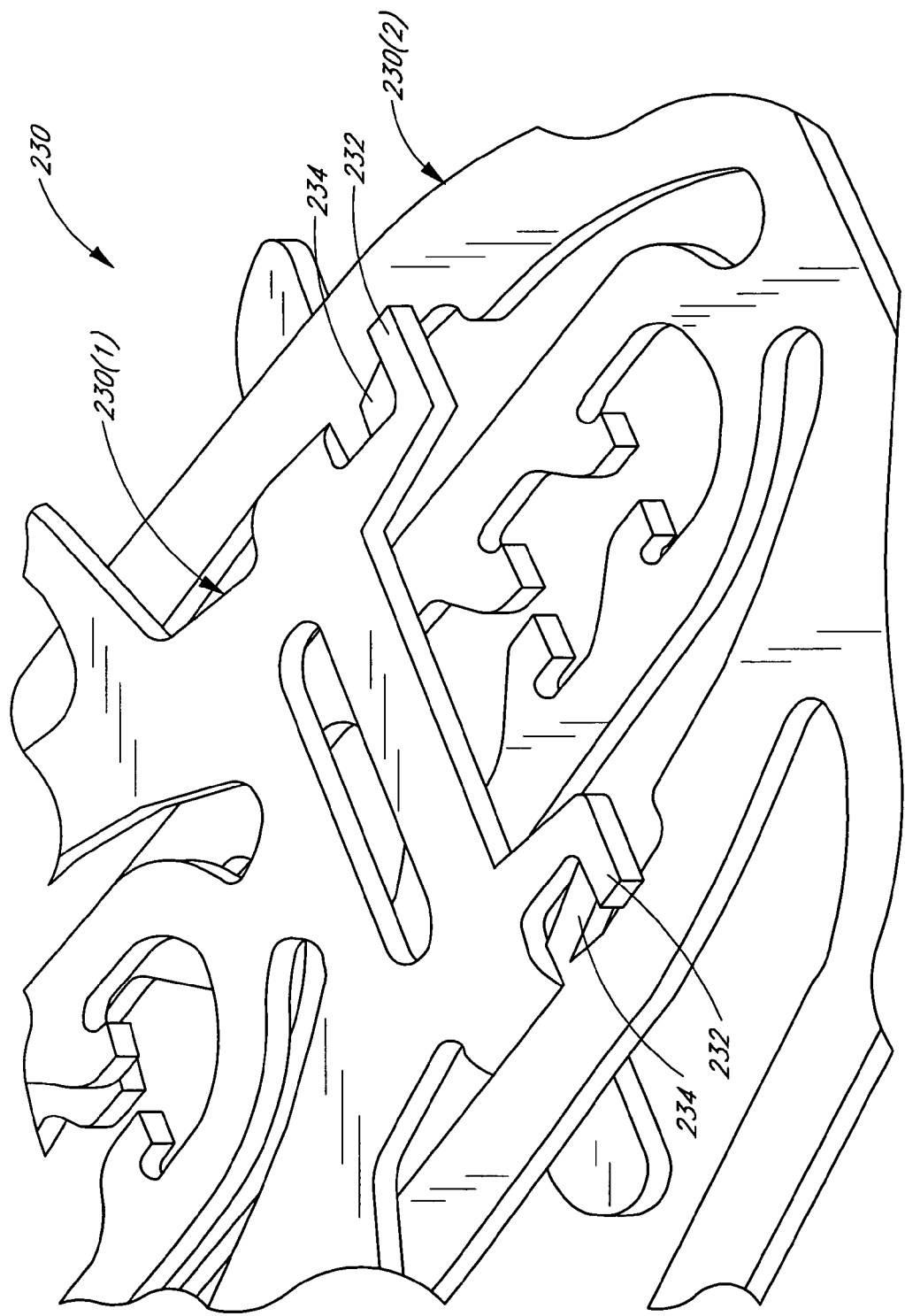
FIG. 11B illustrates the constraint mechanism of FIG. 11A wherein the arms are sliding over the locks for movement into the locked position.
Figure 11C:
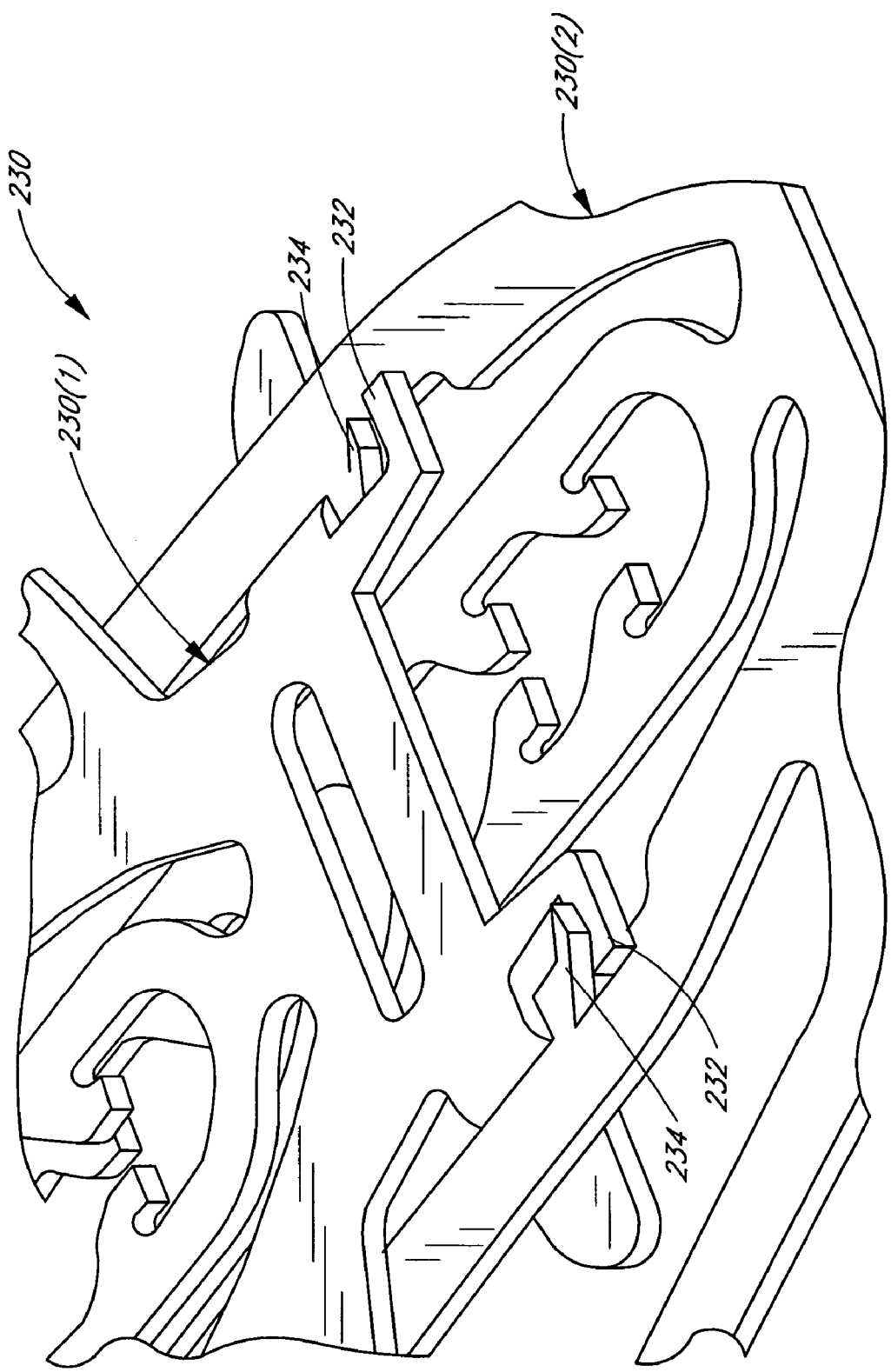
FIG. 11C illustrates the constraint mechanism of FIG. 11A wherein the arms have passed over the locks such that the adjacent interconnected elements are constrained in the collapsed condition.

With reference now to FIGS. 11A-11C, yet another alternative embodiment of a constraining mechanism 230 is illustrated for holding adjacent radial elements in a collapsed condition during delivery. The constraining mechanism 230 generally comprises arms 234 extending from a first end of a first radial element 230(1) and corresponding locks 232 that are provided along a second radial element 230(2). FIG. 11A illustrates the first and second interconnected radial elements in an unlocked configuration. FIG. 11B illustrates the arms 234 of the first radial element sliding over the locks 232 of the second radial element as the radial elements are being moved into a locked (i.e., collapsed) position. As the arms 234 slide, the locks 232 flex to allow the arm to pass over. As shown in FIG. 11C, the arms 234 are located beyond the locks 232 such that the arms 234 are held down in a crimped position. When a balloon is inflated, the first radial element bows such that the arms 234 slide out from underneath the locks 232 for allowing the radial elements to slide with respect to each other.

Figure 12:
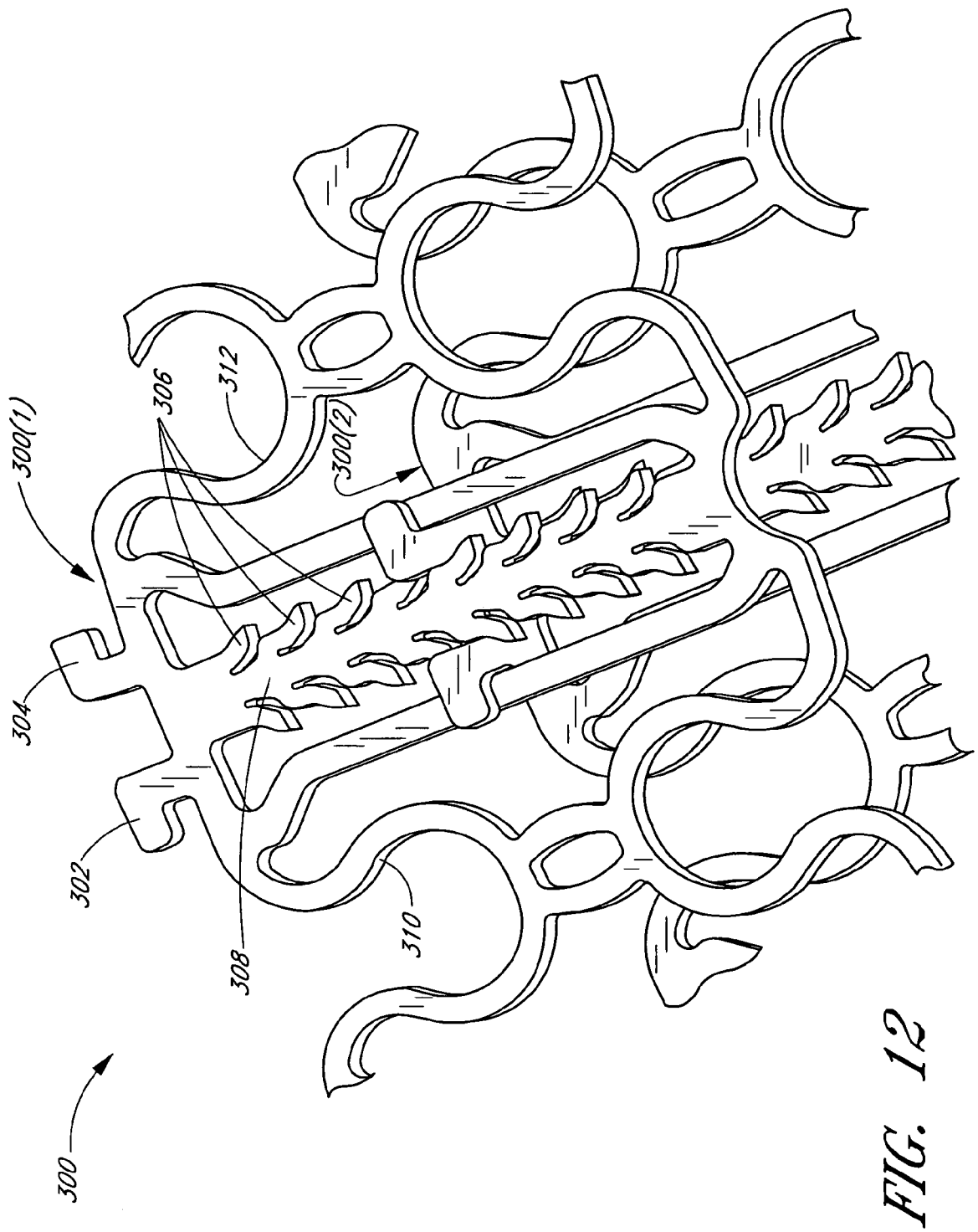
FIG. 12 illustrates an alternative locking mechanism comprising deflectable teeth which deflect inward to provide a stent exhibiting mono-directional expansion.

In yet another alternative embodiment of a balloon expandable crush-recoverable stent, it will be appreciated that deflectable teeth may be used, rather than deflectable members, to provide the stent with mono-directional expansion. For example, FIG. 12 illustrates a portion of another stent embodiment 300 wherein two radial elements 300(1), 300(2) are slidably interconnected. Each radial element is provided with a longitudinal member 308 having a plurality of deflectable teeth 306. Similar radial elements may be coupled via flexible linkage elements 310, 312 to provide a stent having a desired axial length. In this embodiment, locking tabs 302, 304 are configured to ride along the sides of the deflectable teeth 306. Each of the teeth is sufficiently flexible such that the teeth may deform inward toward the longitudinal member 308 (i.e., within the plane of the radial element) for allowing the locking tabs 302, 304 to pass in one direction. However, due to the angle of the teeth, the locking tabs are prevented from moving in the other direction, thereby providing yet another preferred mechanism for maintaining the stent in the expanded condition after deployment.

Figure 13:
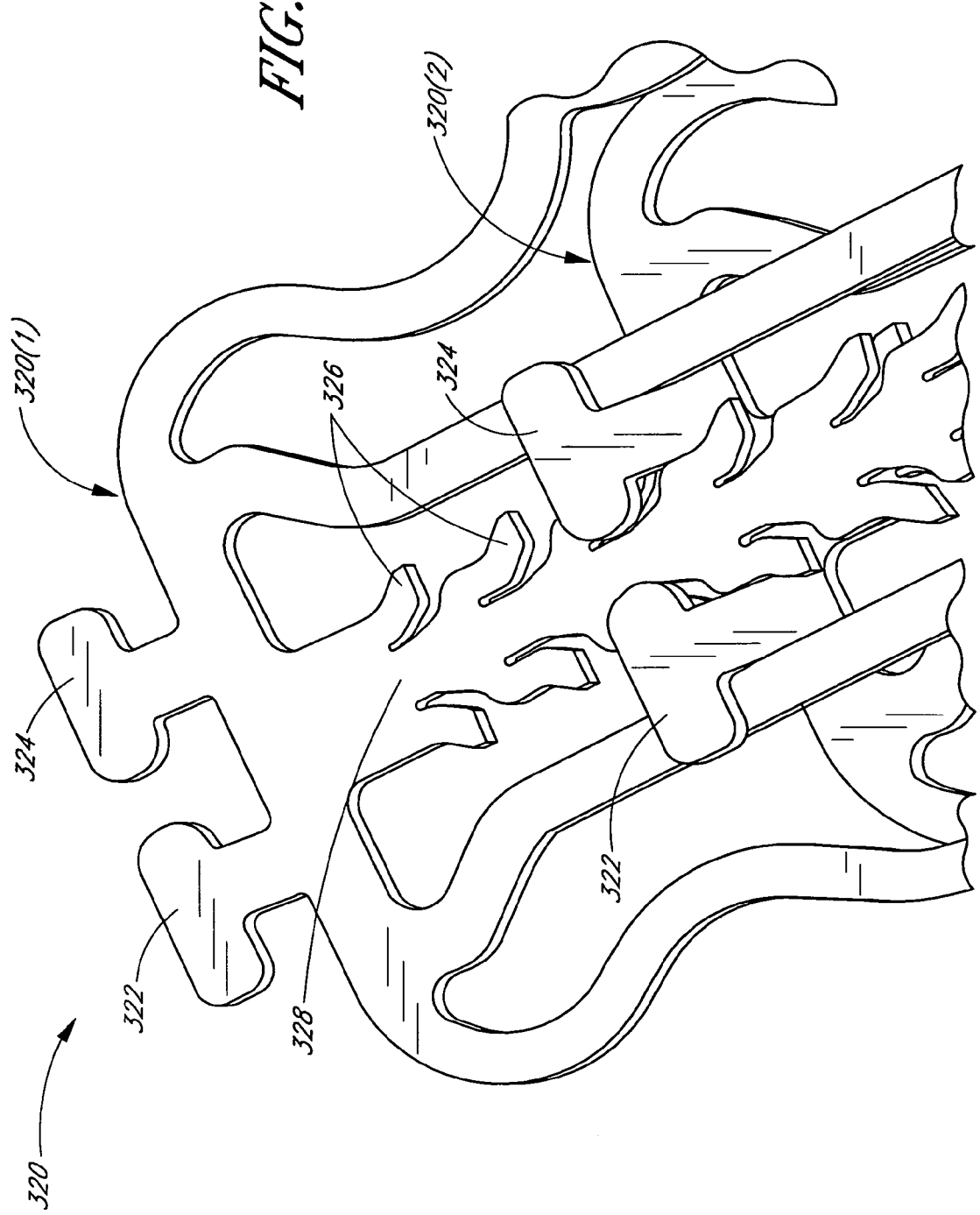
FIG. 13 illustrates another alternative locking mechanism comprising deflectable teeth which deflect downward to provide a stent exhibiting mono-directional expansion.
Figure 14:
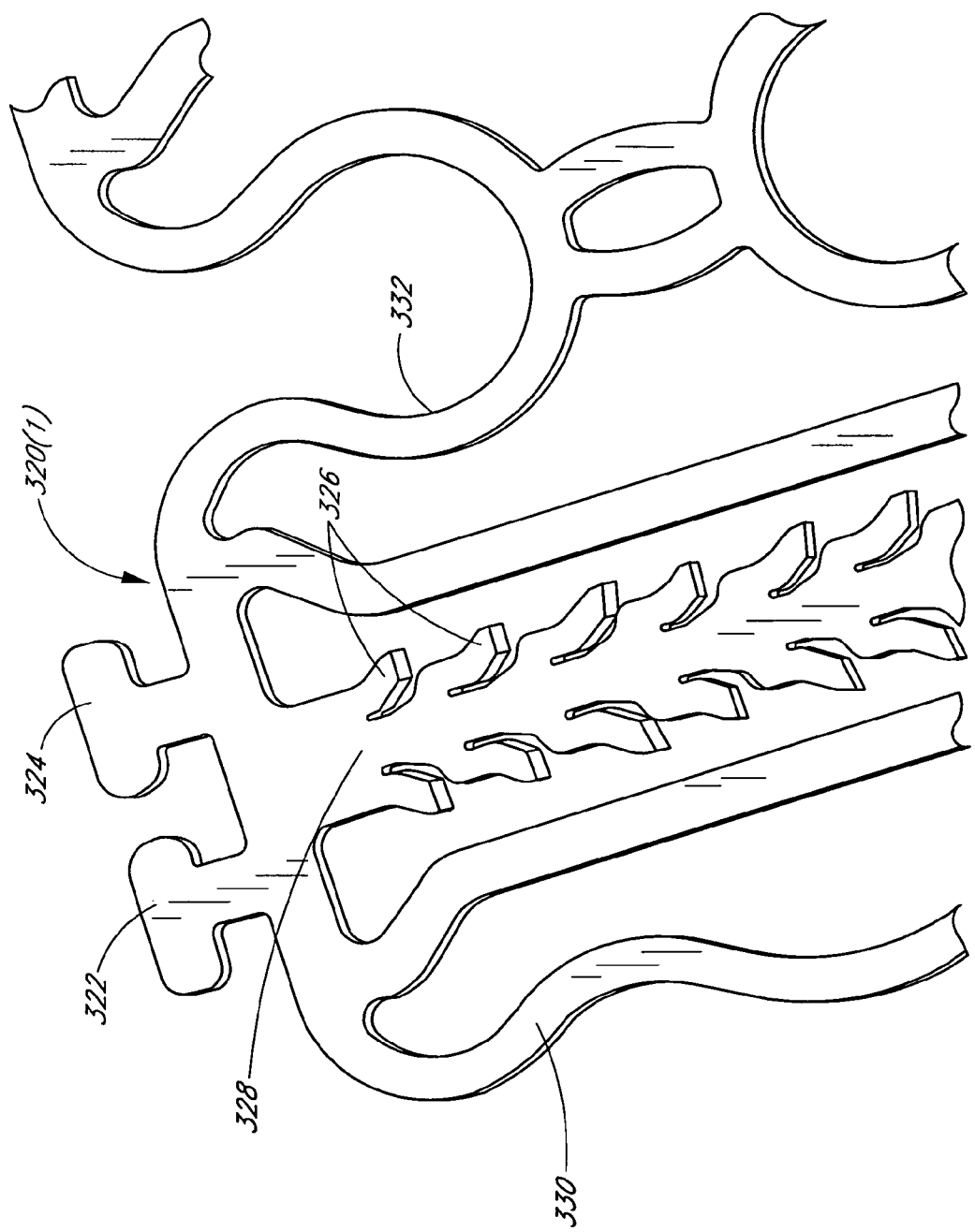
FIG. 14 illustrates a portion of a single element from the embodiment shown in FIG. 13.

With reference now to FIG. 13, a portion of another preferred stent embodiment 320 is illustrated wherein radial elements 320(1), 320(2) are slidably interconnected. Similar to the embodiment just described, each radial element is provided with a single longitudinal member 328 having a plurality of deflectable teeth 326. However, in this embodiment, each of the teeth is angled upward and is configured to deflect downward (i.e., in a radial direction), rather than inward toward the longitudinal member as discussed with respect to FIG. 12. As the locking tabs 322, 324 ride along the deflectable teeth 326, the teeth are caused to deflect downward for allowing the tabs 322, 324 to pass over the teeth 326 during deployment. However, due to the angle of the teeth, the locking tabs may only move in one direction. More particularly, if a compressive force pushes the radial elements 320(1), 320(2) back toward the collapsed condition, the locking tabs 322, 324 will abut against the teeth 326, thereby preventing further relative movement. For additional reference, FIG. 14 illustrates radial element 320(1) in isolation. Flexible linkage elements 330, 332 allow multiple radial elements to be joined to form a row.

Figure 15:
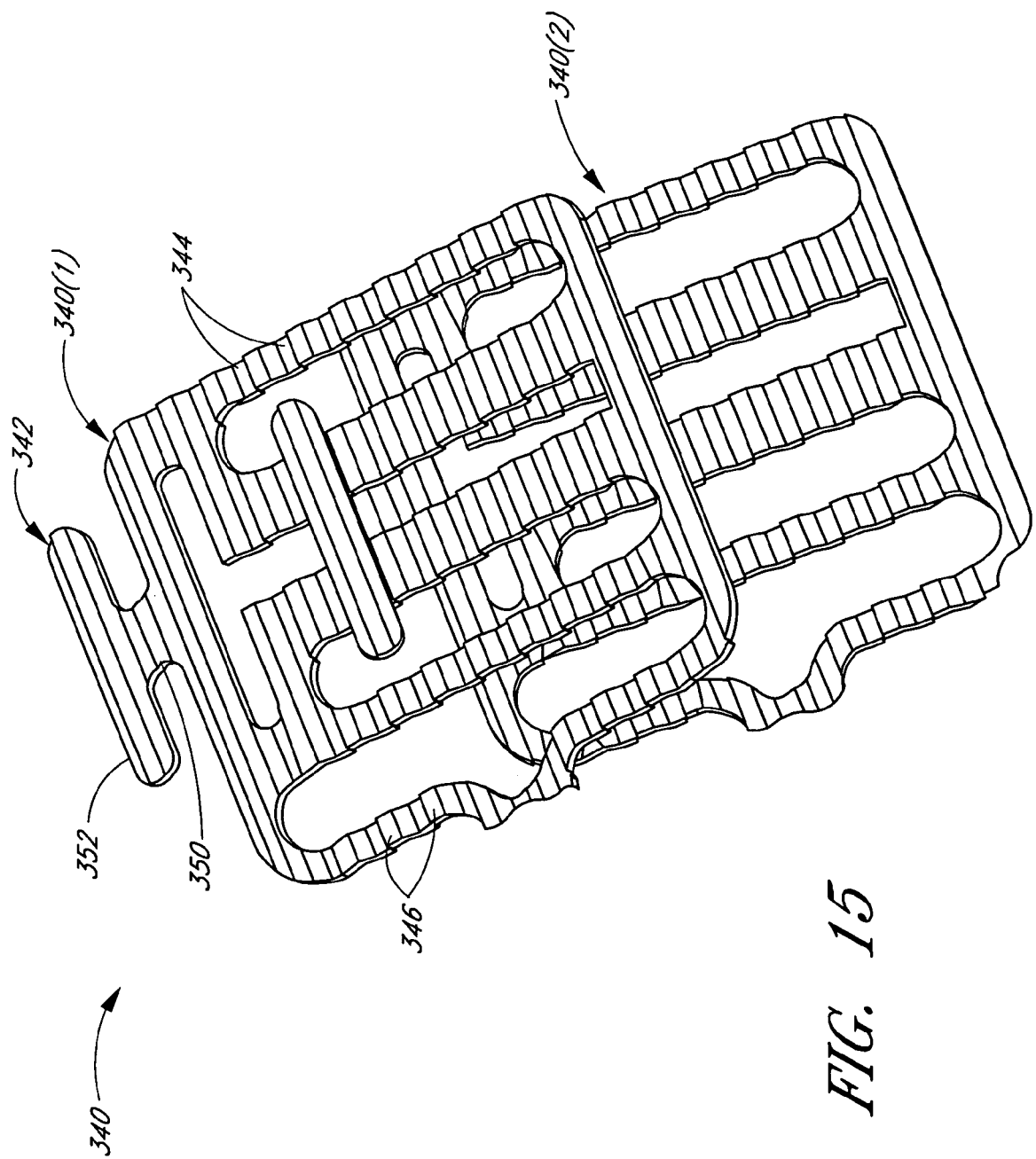
FIG. 15 illustrates another alternative locking mechanism comprising a single tab and series of shaped ridges that provide a stent exhibiting mono-directional expansion.

With reference now to FIG. 15, a portion of another stent embodiment 340 is illustrated wherein radial elements 340(1), 340(2) are slidably interconnected. Each radial element is provided with an outer surface formed, at least in part, with a series of serrations or ridges. More particularly, the surfaces comprise a series of valleys 344 and ridges 346. In the illustrated configuration, a locking tab 342 of radial element 340(2) slides along the surface of radial element 340(1). The locking tab 342 is formed with a thin neck portion 350 and a wider head portion 352. The neck portion 350 is configured for allowing the head 352 to deflect outward in a radial direction. The shape of the valleys 344 and ridges 346 allows the head 352 of the locking tab 342 to ratchet along the surface of the adjacent element in only one direction, thereby providing a locking means to maintain the stent in the expanded condition. Although the ridges and valleys are only necessary along the region wherein the locking tab slides, each of the radial elements may be formed with a continuous contoured surface for ease in manufacturing. In one variation, the shaped bottom surface of the first element 340(1) may slide along the top surface of the shaped second element 340(2) for providing the desired ratcheting effect. In this variation, the tab 342 may be used primarily for interconnecting the elements in a slidable configuration.

Figure 16:
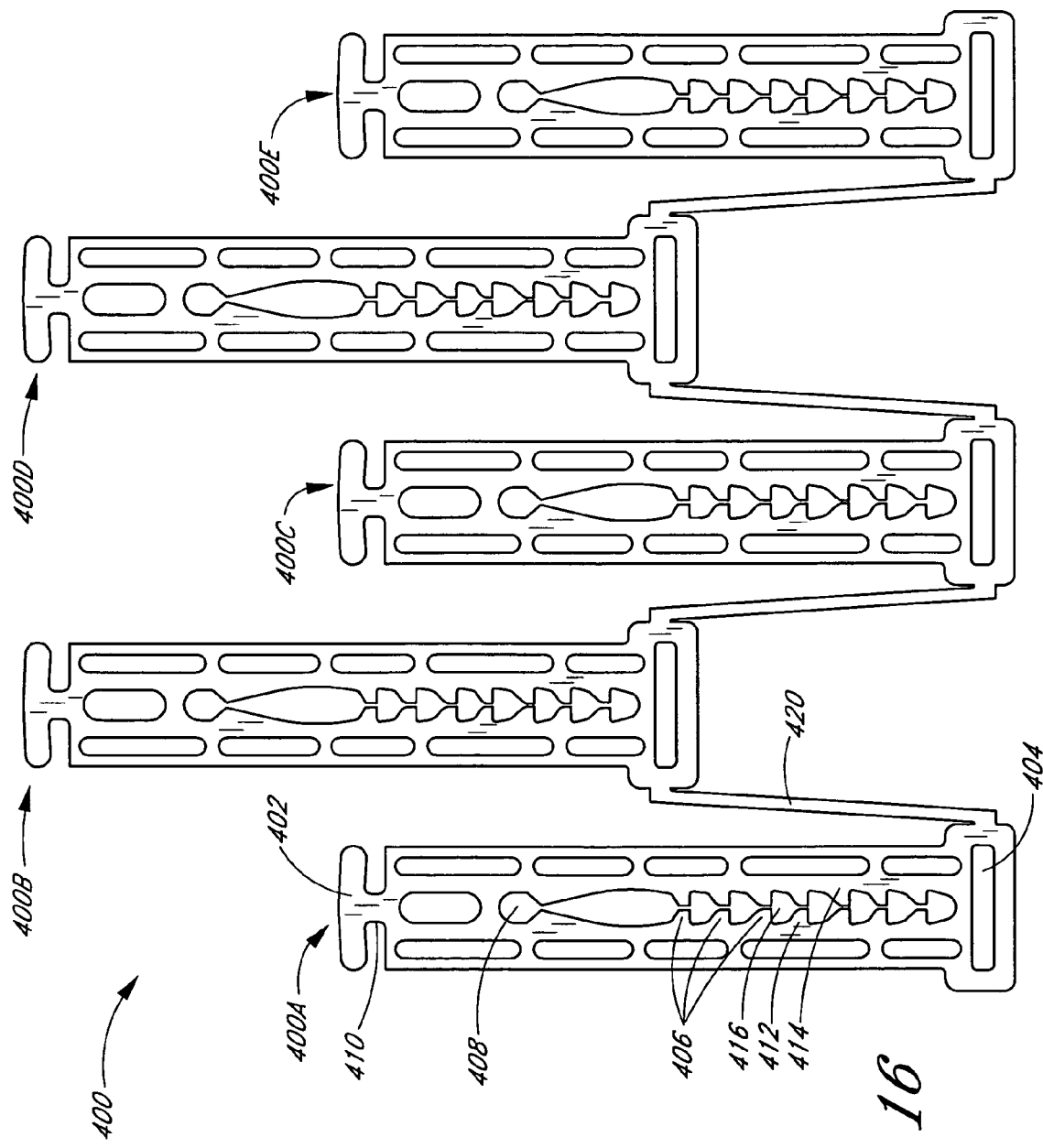
FIG. 16 illustrates another alternative structure comprising a row of staggered radial elements that may be interconnected with similar structures to form a balloon expandable crush-recoverable stent.

With reference now to FIG. 16, another alternative row 400 of radial elements 400A-400E is illustrated. In this embodiment, the individual radial elements are coupled in a staggered arrangement by a series of flexible rails 420. In preferred embodiments, the illustrated row 400 may be slidably interconnected with other similar rows to provide a balloon expandable crush-recoverable stent. Each of the radial elements is substantially identical and includes a locking tab 402 having a neck portion 410. Each of the radial elements further includes a containment gap 408 for holding an adjacent locking tab and a series of opposing teeth 406 for providing a stent exhibiting mono-directional expansion.

With reference now to FIGS. 17A and 17B, the slide and lock relationship between interconnected radial elements of the type shown in FIG. 16 is illustrated. FIG. 17A shows the radial elements 400A(1), 400A(2) in a collapsed configuration wherein the locking tab 402 of radial element 400A(2) is held within the containment gap 408 of radial element 400A(1). The body of radial element 400A(2) extends through a slot 404 formed in radial element 400A(1) for maintaining the elements in the desired slidable relationship. FIG. 17B shows the radial elements 400A(1), 400A(2) in an expanded condition. As shown in FIG. 17B, the locking tab 402 of 400A(2) is disposed in the gap 416 between deflectable members 412, 414 of 400A(1) and is locked in place by teeth 406.

Figure 17:
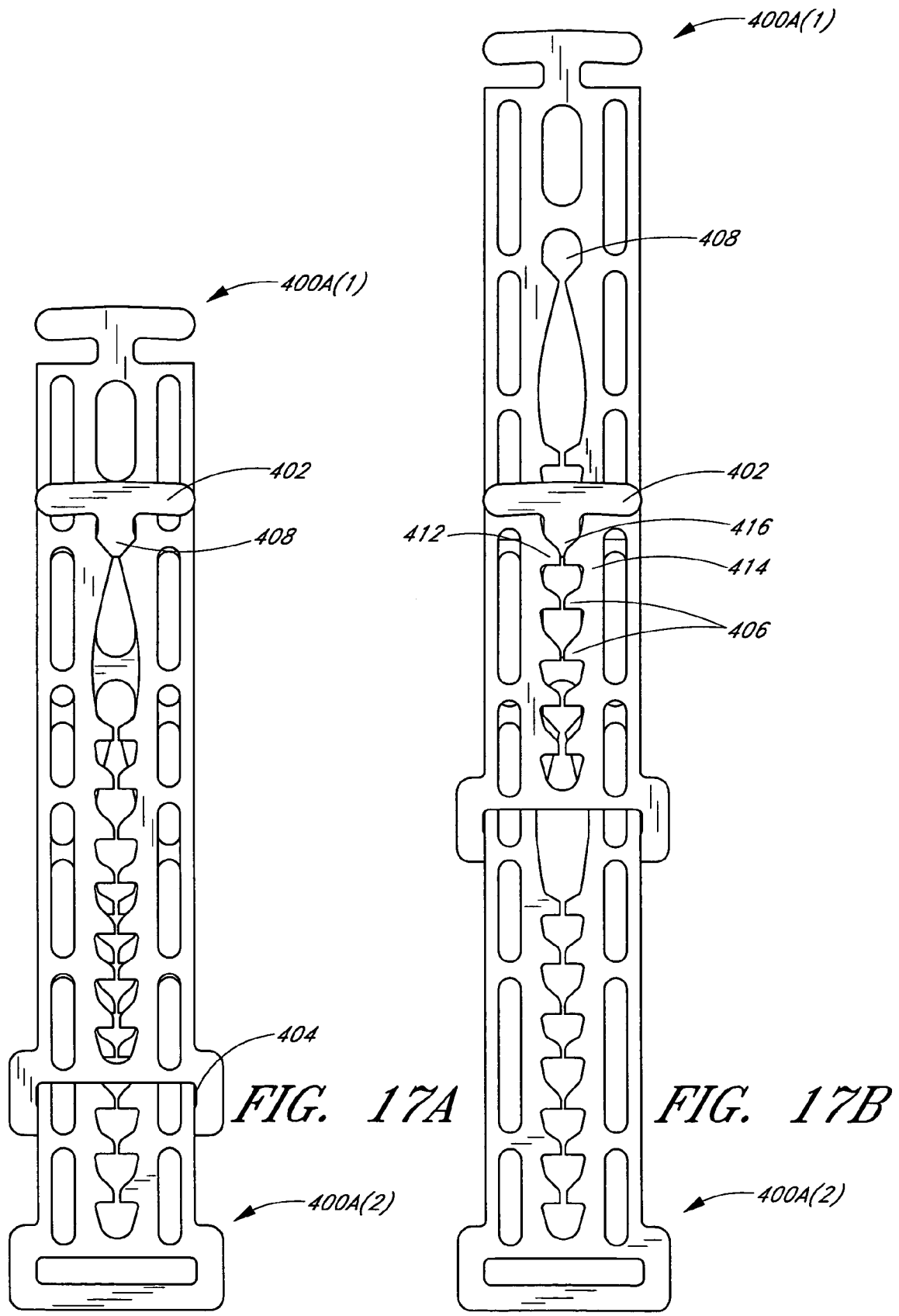
FIG. 17A is a plan view illustrating slidably interconnected radial elements of the type illustrated in FIG. 16 which are constrained in the collapsed condition.
FIG. 17B is a plan view illustrating slidably interconnected radial elements of the type illustrated in FIG. 16 which are locked-out in the expanded condition.

In one advantageous feature, a stent comprising the sliding and locking rows illustrated in FIGS. 16 through 17B provides improved uniformity in surface coverage due to the staggered relationship of the individual radial elements. Furthermore, the stent is capable of providing adequate support to the body lumen while minimizing the total area of surface coverage. This is a particularly advantageous feature since a large percentage of the natural inner surface of the body lumen remains exposed after stent deployment. In another advantageous feature, each radial element passes through the slot 404 of the adjacent radial element for securely maintaining the components in a slidably interlocked condition. Still further, this stent embodiment provides excellent flexibility after deployment.

As discussed above, it will be appreciated by those skilled in the art that stents constructed according to the present invention may comprise a wide variety of other slide and lock elements while still providing the features and advantages described herein. The slide and lock elements illustrated and described above are merely preferred embodiments and alternative slide and lock elements may be employed without departing from the scope of the invention. For example, a variety of alternative one-way locking mechanisms, which may be used to facilitate mono-directional stent expansion, can be found in Applicant's co-owned U.S. Pat. Nos. 6,033, 436, 6,224,626 and 6,623,521, each of which is incorporated by reference herein.

Figure 18:
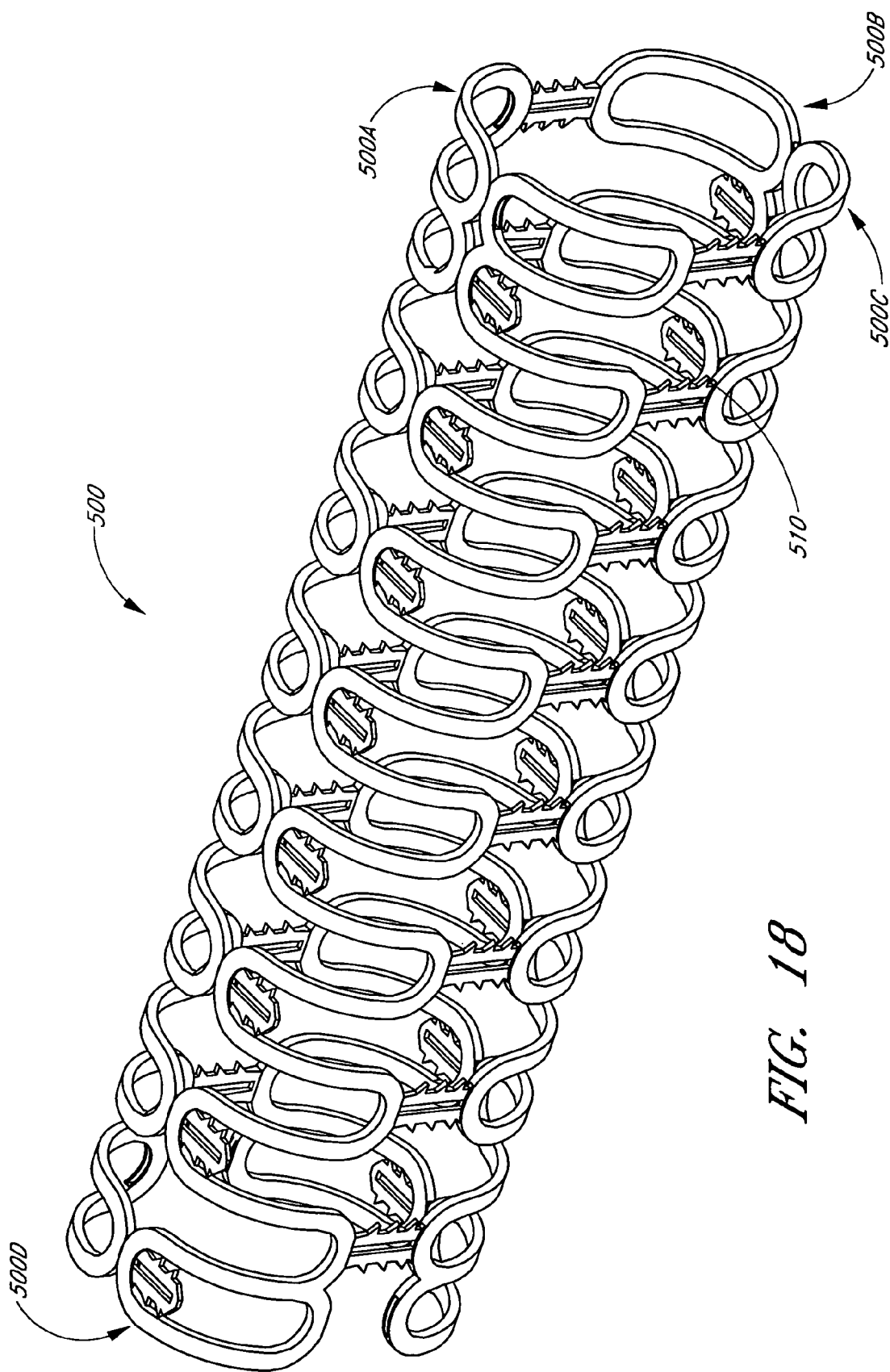
FIG. 18 is a perspective view illustrating another preferred embodiment of a balloon expandable crush-recoverable stent comprising a plurality of interconnected flexible rows.

With reference now to FIG. 18, yet another preferred embodiment of a balloon-expandable, crush-recoverable stent 500 comprises alternative slide and lock mechanisms which are interconnected to provide a tubular member sized for deployment in a body lumen. In the illustrated embodiment, a plurality of interconnected rows 500A-500D is provided wherein each row preferably extends along the entire axial length of the stent 500. This stent configuration advantageously combines excellent longitudinal flexibility (i.e., bending) with a very high radial strength. Although the stent 500 shown in FIG. 18 is illustrated with four interconnected rows 500A-500D, the number and length of the rows may vary to meet the particular requirements of the application.

Figure 18A:
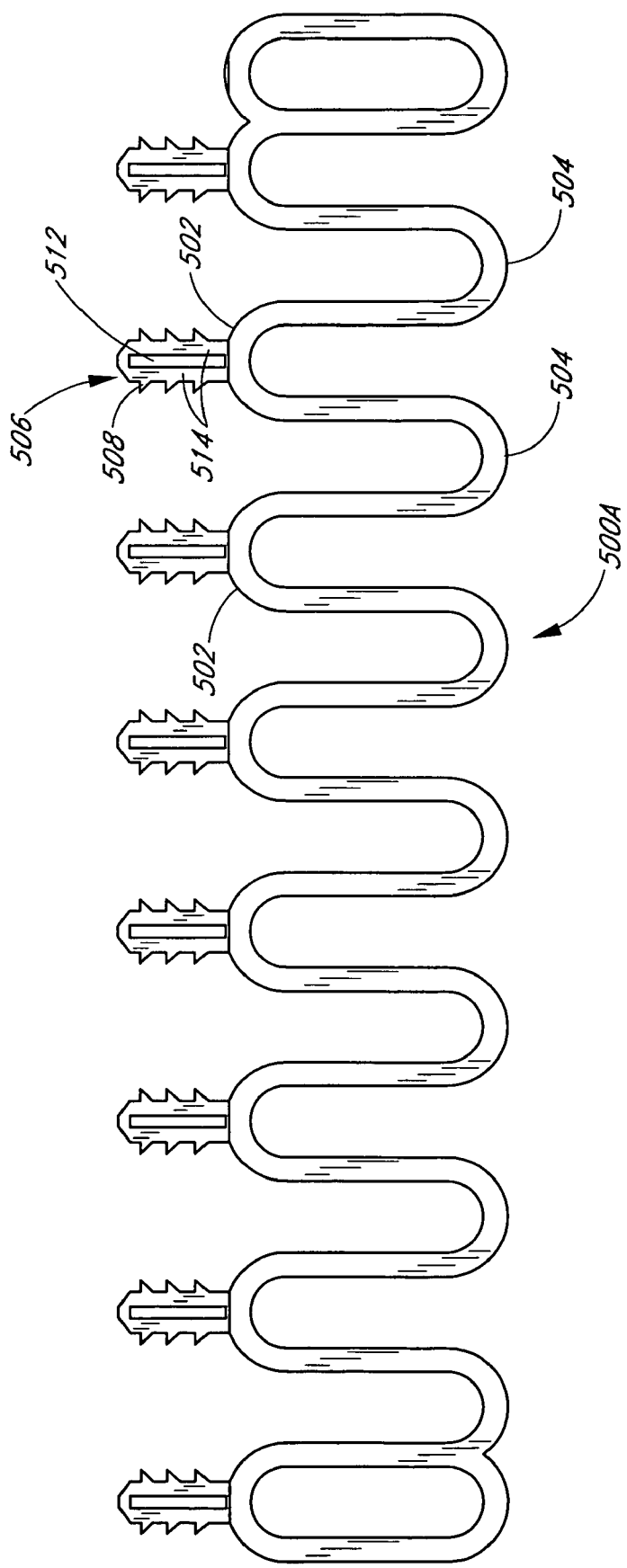
FIG. 18A is a plan view illustrating a single flexible row from the stent embodiment of FIG. 18.

With reference now to FIG. 18A, a single row 500A comprises a structure shaped for providing the stent with excellent flexibility along the longitudinal axis. This feature allows the stent to bend during delivery and to more easily conform to the shape of a body lumen after deployment. Furthermore, this embodiment eliminates the need for flexible linkage elements. The row 500A illustrated in FIG. 18A includes a series of peaks 502 and valleys 504 wherein each peak is provided with a protrusion 506 and each valley is provided with a slot (e.g., see 510 of FIG. 18) shaped for receiving an adjacent protrusion. As illustrated, each of the protrusions 506 is preferably provided with two parallel deflectable members 514 formed with a number of teeth 508. Each of the teeth 508 is formed with an angled side and a flat side. Furthermore, each of the protrusions 506 is formed with a gap 512 extending between the deflectable members 514.

When assembled, the protrusions 506 are slidably received within the slots 510 as illustrated in FIG. 18. The interaction between the angled teeth 508 and slots 510 is preferably configured to provide a stent 500 exhibiting mono-directional expansion. In particular, during expansion, the interaction between the teeth 508 and the slot 510 causes the deflectable members 514 to flex inward for allowing the teeth to pass through the slot 510. The deflectable members 514 are caused to flex inward because the edges of the slot act on the angled side of the teeth. However, when a force is applied in the other direction, the flat sides of the teeth abut against the edges of the slot and no inward force is produced. Accordingly, the teeth 508 are prevented from sliding back out of the slots 510, thereby maintaining the stent in the expanded condition after deployment at a treatment site.

In preferred embodiments, the force required to move the protrusions through the slots is large enough such that the stent will not inadvertently expand during delivery to the treatment site. Therefore, the stent is held down in the collapsed condition before the balloon is expanded. If necessary, the assembly may be constructed such that the initial resistance produced by the first set of teeth on each protrusion is greater to ensure that the stent remains in the collapsed condition during delivery.

In an advantageous feature, each of the mating protrusions and slots may move (i.e., ratchet) independently of the others. Accordingly, in addition to providing excellent flexibility, the diameter of the stent may vary along the longitudinal axis for precisely conforming to the inner diameter of the vessel. In still another advantage, the protrusions are received within slots formed in the adjacent row. Therefore, the slide and lock mechanism maintains a very low profile after deployment.

Figure 19:
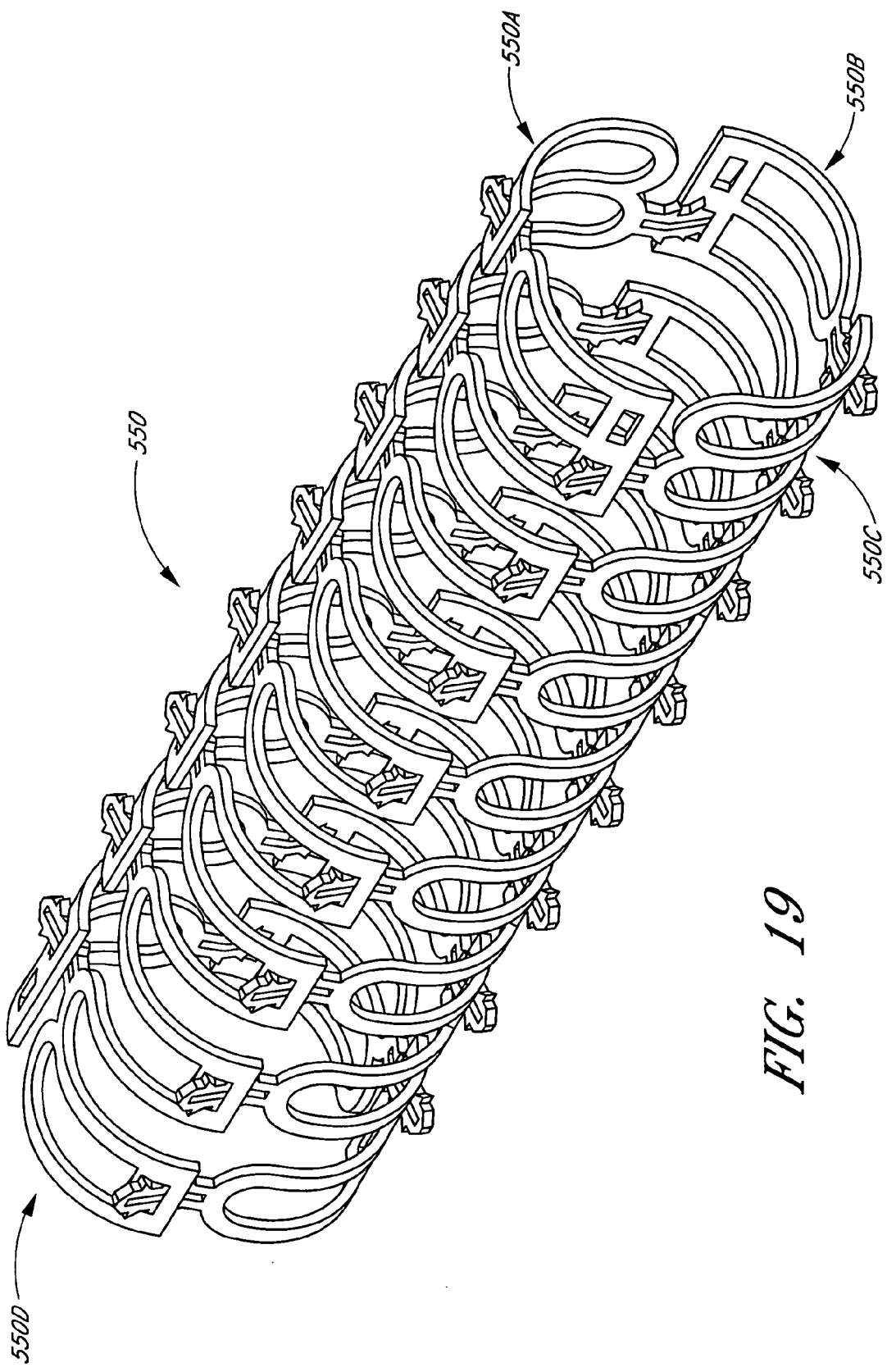
FIG. 19 is a perspective view illustrating yet another preferred embodiment of a balloon expandable crush-recoverable stent comprising a plurality of interconnected flexible rows.

With reference now to FIG. 19, a balloon-expandable, crush-recoverable stent 550 comprises yet another configuration of slide and lock elements which are interconnected to provide a tubular member sized for deployment in a body lumen. Similar to the stent described above with respect to FIG. 18, in this embodiment, a plurality of interconnected rows 550A-550D is provided wherein each row preferably extends along the entire axial length of the stent 550. Although the stent 550 shown in FIG. 19 is illustrated with four interconnected rows 550A-550D, the number and length of the rows may vary to meet the particular requirements of the application.

Figure 19A:
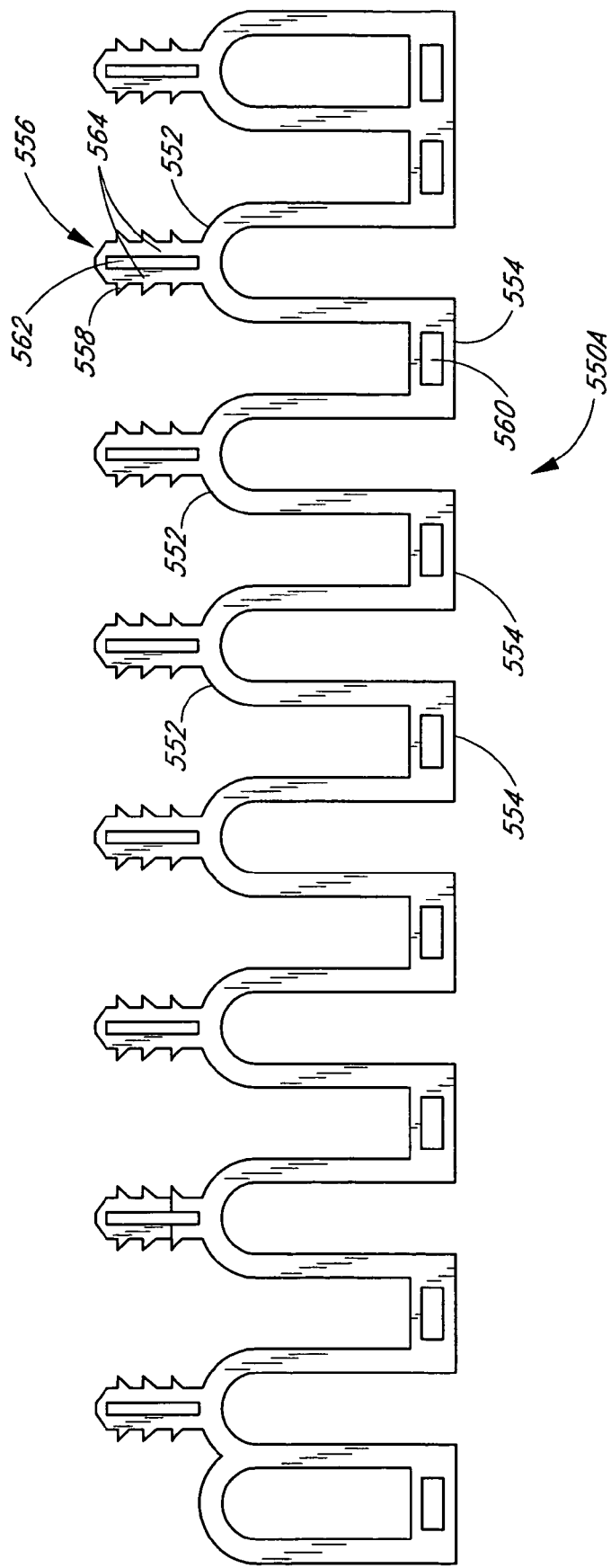
FIG. 19A is a plan view illustrating a single flexible row from the stent embodiment of FIG. 19.

With reference now to FIG. 19A, a single row 550A comprises a structure shaped for providing the stent with excellent flexibility. This feature allows the stent to bend during delivery and to more easily conform to the shape of a body lumen after deployment. The row illustrated in FIG. 19A includes a series of peaks 552 and valleys 554 wherein each peak is provided with a protrusion 556 and each valley is provided with a slot extending therethrough. Each of the protrusions 556 is preferably provided with two deflectable members 564 formed with a number of teeth 558. Each of the teeth 558 is formed with an angled side and a flat side. Furthermore, each of the protrusions 556 is formed with a gap 562 extending between the deflectable members 564. When assembled, the protrusions 556 are slidably received within the slots 560 as illustrated in FIG. 19. The interaction between the angled teeth 558 and slots 560 is preferably configured to provide a stent 550 exhibiting mono-directional expansion. In particular, during expansion, the interaction between the teeth 558 and the slot 560 causes the deflectable members 564 to flex inward for allowing the teeth to pass through the slot 560. The deflectable members 564 are caused to flex inward because the sides of the gap act on the angled side of the teeth. However, when a force is applied in the opposite direction, the flat sides of the teeth abut against the sides of the gap and no inward force is produced. Accordingly, the teeth 558 are prevented from sliding back out of the slots 560, thereby maintaining the stent in the expanded condition after deployment at a treatment site.

With reference again to the embodiment illustrated in FIG. 19, the protrusions preferably pass in a radial direction through the gaps in the adjacent rows. After deployment, an end portion of each protrusion may protrude radially outward from the tubular member, as shown in FIG. 19. The end portions may advantageously provide an anchoring mechanism for further securing the stent 550 at the treatment site after deployment. In another advantageous feature, the stent embodiment 550 illustrated in FIG. 19 may be constructed in an inexpensive manner and provides a modular design that may be combined in a variety of different ways to provide an expandable stent suited for a particular purpose.

Figure 20:
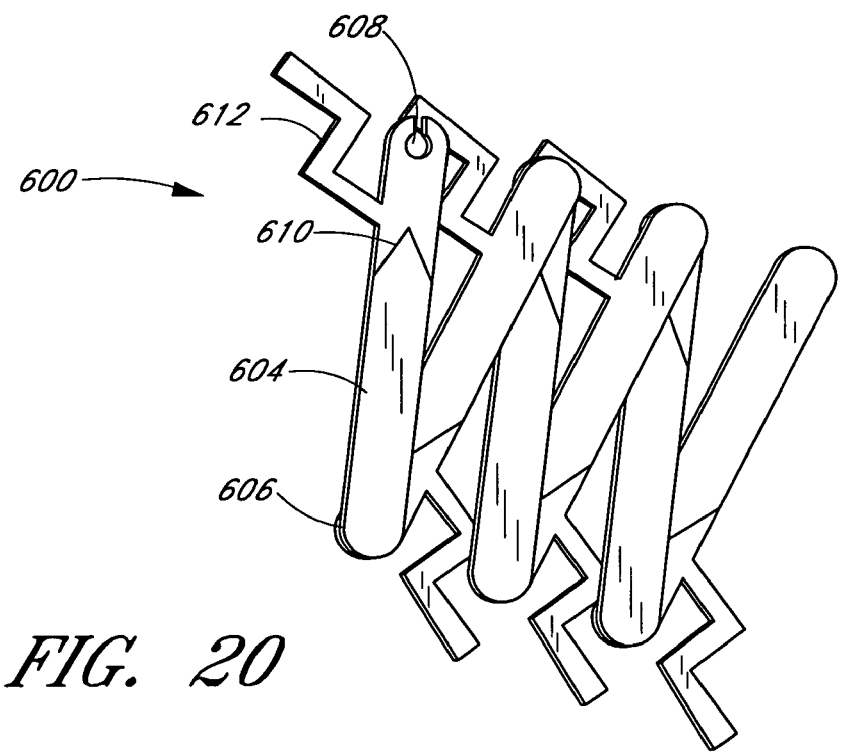
FIG. 20 is a plan view illustrating another alternative embodiment of an expandable structure that may be used to form a balloon expandable crush-recoverable stent.
Figure 21:
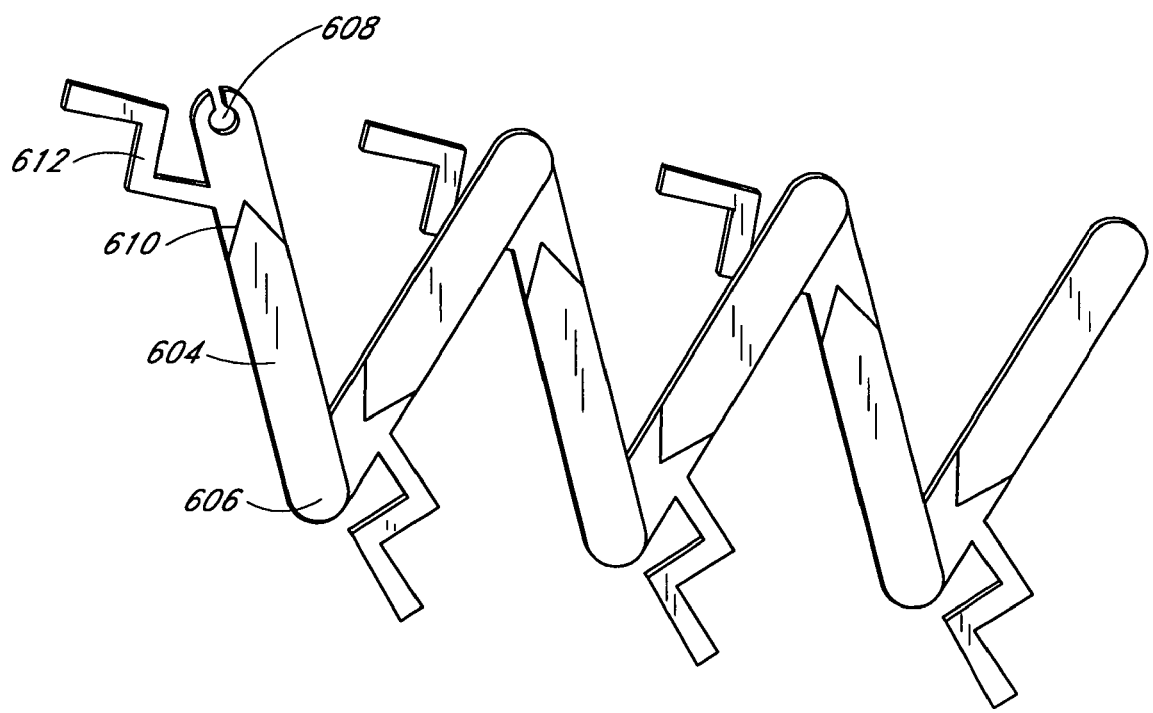
FIG. 21 is a plan view illustrating the expandable structure of FIG. 20 in the expanded condition.

With reference now to FIGS. 20 and 21, yet another embodiment of an expandable structure 600 for use with a balloon expandable stent is illustrated. In this embodiment, a series of links 604 may be pivotally connected to provide an expandable module shaped as a tubular member. Each of the links 604 has a first end 606 and a second end 608. The first end is provided with a pin or connector (not shown). The second end 608 is provided with a gap for receiving the connector in a pivotal relationship. The connector may be shaped such that the connector initially resists pivoting within the gap for constraining the stent in the collapsed condition during delivery. Each link 604 is also preferably provided with a flexible mechanism 612 for connecting multiple expandable modules together to form a stent having a desired axial length. Ridges 610 may be provided along the surface of each link to create a barrier, thereby limiting the pivoting of the links in the collapsed direction. FIG. 20 illustrates the expandable structure in the collapsed condition. FIG. 21 illustrates the expandable structure 600 of FIG. 20 in the expanded condition.

Figure 22A:
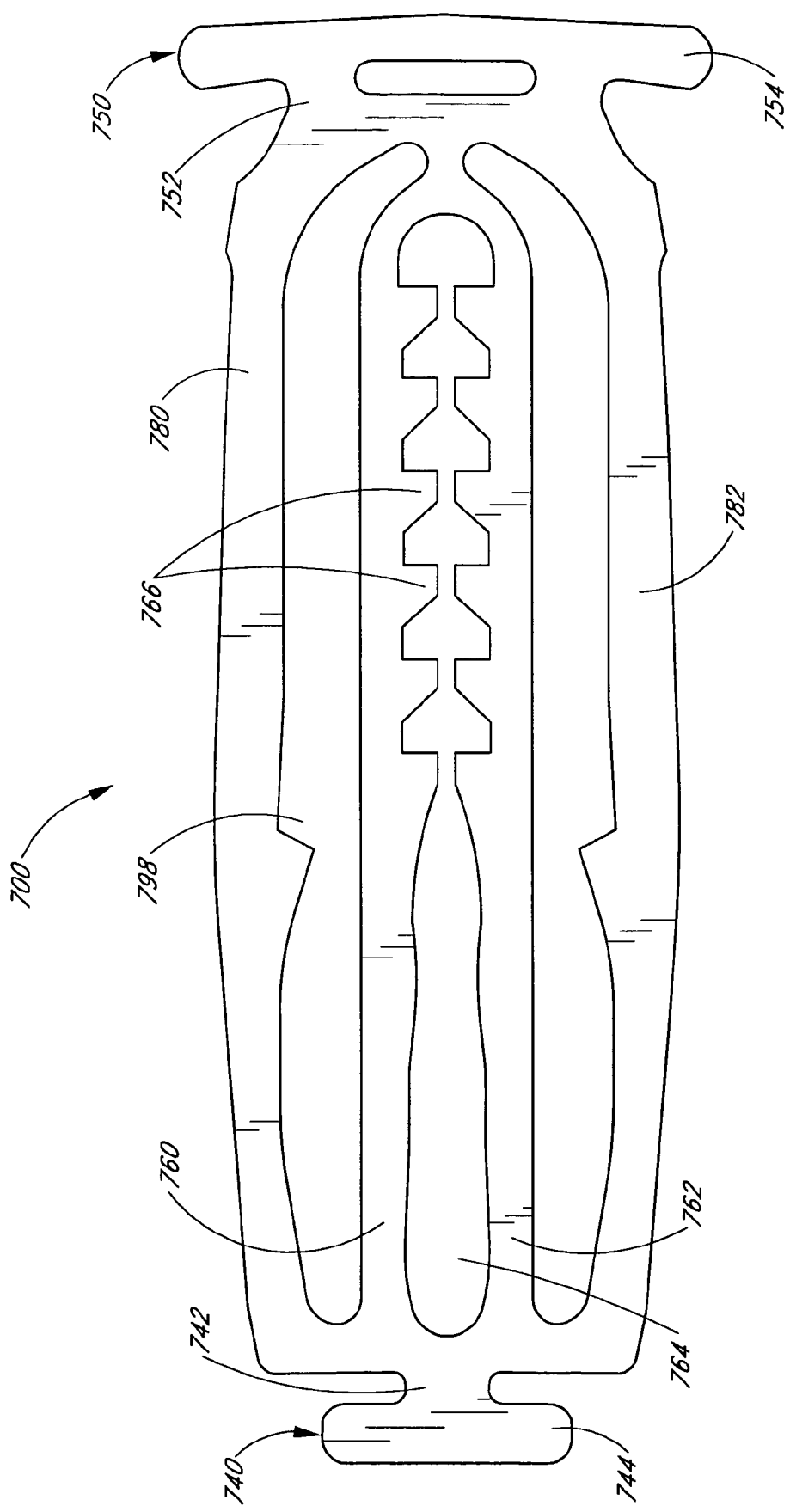
FIG. 22A is a plan view illustrating another preferred embodiment of a balloon expandable crush-recoverable stent comprising a single element that may be rolled onto itself to form a tubular member.
Figure 22B:
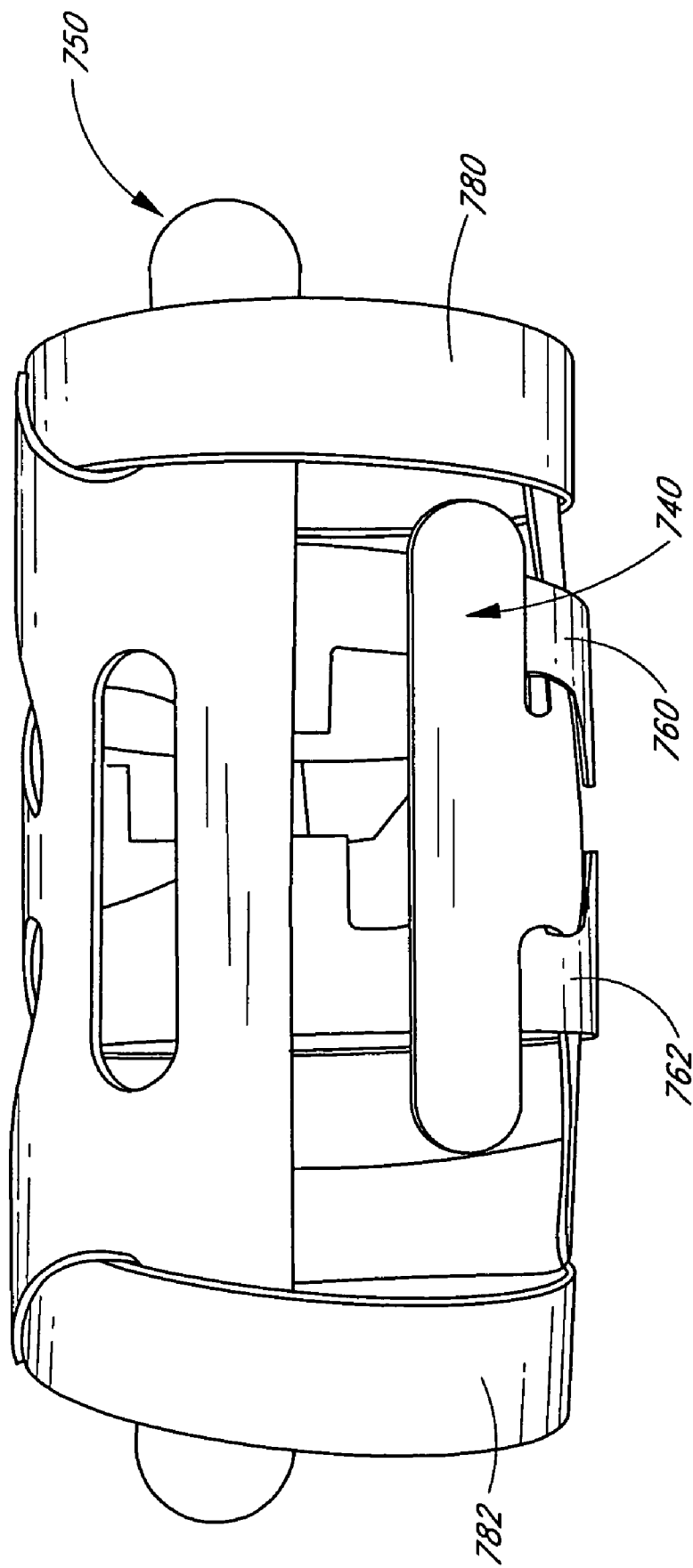
FIG. 22B illustrates the single element of FIG. 22A rolled into a tubular member and constrained in the collapsed condition.
Figure 22C:
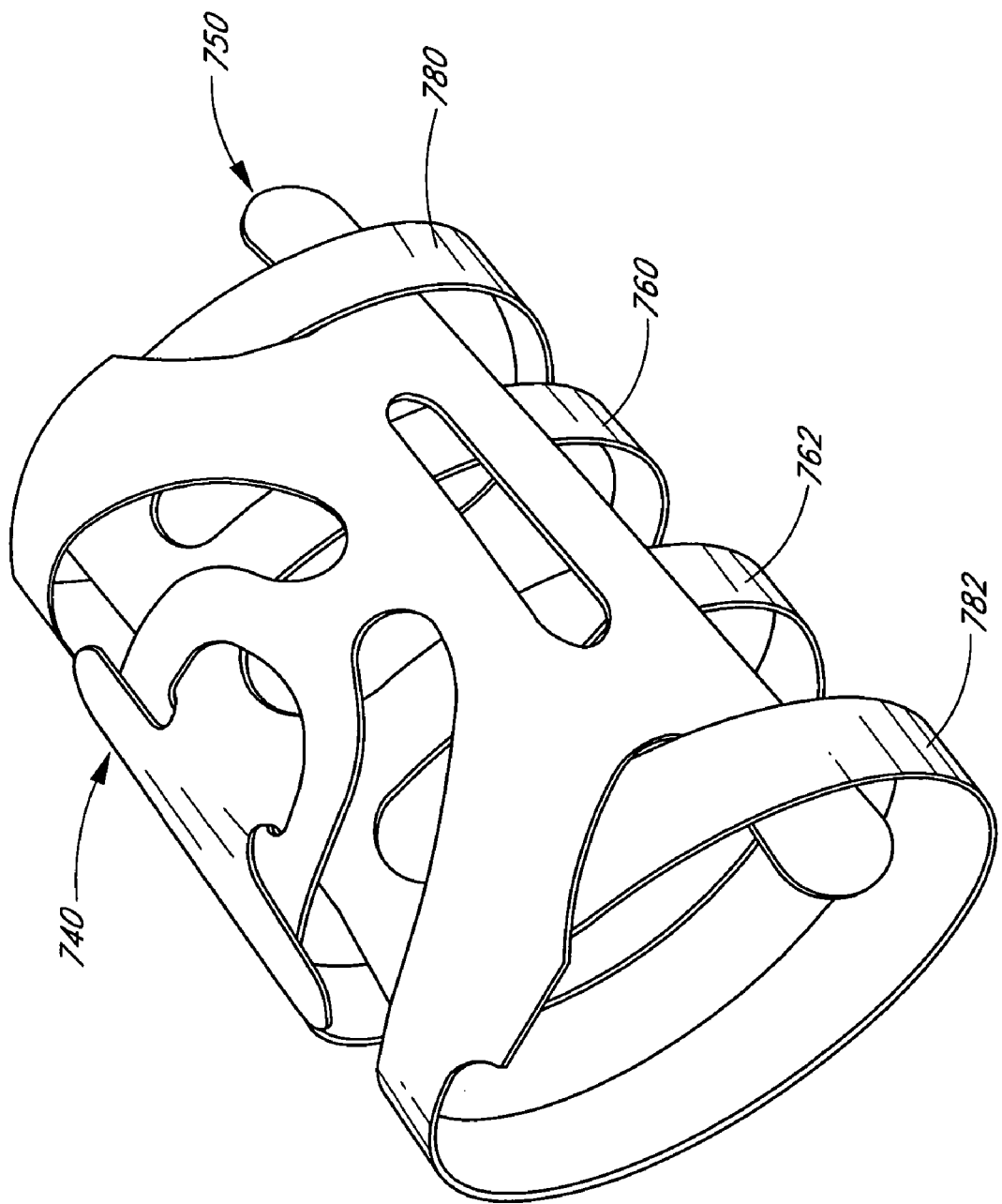
FIG. 22C illustrates the single element of FIG. 22A locked out in the expanded condition.

FIGS. 22A through 22C illustrate yet another alternative embodiment of the present invention wherein an expandable stent is formed from a single element 700. The single element 700 may function in a manner similar to certain embodiments described above. More particularly, the element 700 includes a locking tab 740 having a wide head portion 744 and a thin neck portion 742. The stent also includes a hold-down tab 750 having a wide head portion 754 and a thin neck portion 752. Still further, the stent includes first and second deflectable members 760, 762 formed with teeth 766 along an inner edge. The element 700 also includes first and second containment members 780, 782 disposed in parallel to the deflectable members. As illustrated in FIG. 22B, the single radial element is rolled onto itself to provide a tubular member with the head portion 742 of the locking tab 740 extending through a gap 764 between the deflectable members 760, 762. When in the collapsed condition, as shown in FIG. 22B, the hold-down tab 750 is held within recesses (see element 788 of FIG. 22A) that prevents the stent from expanding during delivery to a treatment site. However, during delivery, the hold-down tab 750 is released from the recesses 788 and the diameter of the radial element expands. During expansion, the locking tab 740 passes through the teeth 766 along the deflectable members 760, 762 until the stent is expanded to the desired diameter, as shown in FIG. 22C. The configuration of the teeth prevent the locking tab 740 from moving back, thereby ensuring that the stent is held in the expanded condition. In an advantageous feature, this embodiment, which has a "jelly-roll" configuration, does not involve any interconnected components and therefore benefits from simplicity in construction. Accordingly, during use, this embodiment provides excellent reliability and structural integrity.

Although a stent formed from a single integral element is described above as having particular mechanical characteristics for locking the stent in the expanded condition, a variety of other "slide and lock" mechanisms may be used without departing from the scope of the invention. For example, other suitable locking mechanism may be found in U.S. Pat. No. 5,344,426 to Lau, U.S. Pat. Nos. 5,735,872 and 5,876,419 to Carpenter, U.S. Pat. No. 5,741,293 to Wijay, U.S. Pat. No. 5,984,963 to Ryan, U.S. Pat. Nos. 5,441,515 and 5,618,299 by Khosravi, U.S. Pat. No. 5,306,286 to Stack, U.S. Pat. No. 5,443,500 to Sigwart, U.S. Pat. No. 5,449,382 to Dayton, U.S. Pat. No. 6,409,752 to Boatman, and the like. Each of these references is incorporated by reference herein. In addition, many of the slide and lock mechanisms disclosed in the above patents may be suitable for use with stents embodiments comprising slidable interconnected elements of the type described above.

Although certain preferred embodiments are described above as providing mono-directional expansion during stent deployment, it will be appreciated that, in another mode of the present invention, the teeth or other engaging elements may be shaped and positioned to allow bi-directional movement (i.e., both expansion and contraction). More particularly, the teeth may be constructed to allow for two-way movement between adjacent radial elements, such that the stent diameter may be collapsed after deployment. The teeth create a barrier that resists the stent from expanding or reducing in diameter. However, the resistance created by the teeth may be overcome during placement of the stent on a balloon and during deployment in the vessel. Preferably, the amount of resistance created by the teeth is selected such that the stent diameter will not reduce due to external pressures after deployment in the vessel. However, the teeth do not provide a locking mechanism that limits stent movement to mono-directional expansion. Accordingly, the diameter of the stent may be reduced for placement on an expandable member. This feature provides a constraining or "hold-down" mechanism that allows the stent to be placed on expandable member and also prevents the stent from expanding prematurely. This embodiment advantageously obviates the need for deformable tabs, pins, crimping mechanisms or other hold-down mechanisms.

Preferred stent embodiments described above provide a variety of improved expandable structures primarily configured to treat body lumens by maintaining the patency of the lumens. To further enhance the effectiveness of the treatment, the stent embodiments described above may comprise an amount of a therapeutic agent (e.g., a pharmaceutical agent and/or biologic agent) sufficient to produce a selected therapeutic effect. The term "pharmaceutical agent", as used herein, encompasses a substance intended for mitigation, treatment, or prevention of disease that stimulates a specific physiologic (e.g., metabolic) response. The term "biological agent", as used herein, encompasses any substance that possesses structural and/or functional activity in a biological system, including without limitation, organ, tissue or cell based derivatives, cells, viruses, vectors, nucleic acids (e.g., animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Furthermore, the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Still further, the term "biological agent" may include the following: 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules, 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

Therapeutic agents can be incorporated onto the stent on at least one region of the stent surface, or in some cases in the stent, thereby providing local release of such agents. In some preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. In other preferred embodiments of the stent, if comprised of polymer rather than a metal, the therapeutic agent is contained within the stent as the agent is blended with the polymer or admixed by other means known to those skilled in the art.

Various preferred therapeutic agents may be provided to control restenosis, including neointimal thickening, intimal hyperplasia and in-stent restenosis or limits vascular smooth muscle cell overgrowth, in the lumen of the treated vessel. Vascular stent applications and other body applications may require a different therapeutic or more than one therapeutic. A variety of compounds are considered to be useful in controlling vascular restenosis and in-stent restenosis. Some of these preferred agents that improve vascular patency include without limitation paclitaxel, Rapamycin, ABT-578, everolimus, dexamethasone, nitric oxide modulating molecules for endothelial function, tacrolimus, estradiol, mycophenolic acid, C6-ceramide, actinomycin-D and epothilones, and derivatives and analogs of each.

Preferred therapeutic agents may also be provided to limit or inhibit thrombosis or affect some other state of the stented tissue, for instance, heal a vulnerable plaque, inhibit plaque rupture, stimulate endothelialization or limit other cell types from proliferating and from producing and depositing extracellular matrix molecules. The agents may be selected from the group consisting of but not limited to: antiproliferative agents, anti-inflammatory, anti-matrix metalloproteinase, and lipid lowering, anti-thrombotic and antiplatelet agents, in accordance with preferred embodiments of the present invention.

In one preferred stent embodiment, the device delivers one or more therapeutic agents to treat the vulnerable plaque lesion such as an anti-inflammatory, a lipid lowering/matrix altering therapeutic and/or an antiproliferative. The anti-inflammatory may include aspirin, an effective neutralizer of inflammation, losartan, an angiotensin receptor blocker or pravastatin, a 3-Hydroxy-3-Methyl-Glutaryl Coenzyme A (HMG-CoA) reductase inhibitor. Further delivery of statins, such as pravastatin and fluvastatin, which are 3-HMG-CoA reductase inhibitors may interstitial collagen gene expression and lower matrix metalloproteinases (MMP-1, MMP-3, and MMP-9) expression to effectively stabilize the vulnerable plaque lesions. Local stent delivery of lipid-lowering agent, for example Pravastatin, may also improve plaque stability.

In another preferred stent embodiment, the device delivers an antiplatelet agent that acts by glycoprotein IIb/IIIa receptor inhibition or other means such as but not limited to aspirin, Plavix (clopidogrel bisulfate), ticlopidine, integrelin, and dipyridamole. In another preferred stent embodiment the device delivers an antithrombin agent that acts by thrombin inhibition or other means such as heparin, low molecular weight heparin (LMWH), polyamine to which dextran sulfate and heparin are covalently bonded, heparin-containing polymer coating for indwelling implants (MEDI-COAT by STS Biopolymers), polyurethane urea/heparin, R-Hirudin, Hirulog, hirudin/prostacyclin and analogues, argatroban, efegatran, and tick anticoagulant peptide. Additional anti-thrombogenic substances and formulations may include but are not limited to endothelium-derived relaxing factor, prostaglandin I2, plasminogen activator inhibitor, tissue-type plasminogen activator (tPA), ReoPro: anti-platelet glycoprotein IIb/IIIa integrin receptor, fibrin and fibrin peptide A, lipid-lowering drugs, e.g., Omega-3 fatty acids, and Chrysalin (aka TRAP-508) by Chrysalis Vascular Technologies.

Various compounds address other pathologic events and/or vascular diseases. Some of these therapeutic target compounds are agents to treat endothelial injury (e.g., VEGF; FGF), agents to modulate cell activation and phenotype (e.g., MEF-2 & Gax modulators; NFKB antagonists; cell cycle inhibitors), agents for dysregulated cell growth (e.g., E2F decoys; RB mutants; cell cycle inhibitors), agents for dysregulated apoptosis (e.g., Bax or CPP32 inducers; Bcl-2 inhibitors; integrin antagonists) and agents for abnormal cell migration (e.g., integrin antagonists; PDGF blockers; plasminogen activator inhibitors).

Various therapeutic agents to be coated or incorporated within the stent polymer may be classified in terms of their sites of action in the host. The following agents are believed to exert their actions extracellularly or at specific membrane receptor sites. These include corticoids and other ion channel blockers, growth factors, antibodies, receptor blockers, fusion toxins, extracellular matrix proteins, peptides, or other biomolecules (e.g., hormones, lipids, matrix metalloproteinases, and the like), radiation, anti-inflammatory agents including cytokines such as interleukin-1 (IL-1), and tumor necrosis factor alpha (TNF-α), gamma interferon (interferon-γ), and Tranilast, which modulate the inflammatory response.

Other groups of agents exert their effects at the plasma membrane. These include those involved in the signal transduction cascade, such as coupling proteins, membrane associated and cytoplasmic protein kinases and effectors, tyrosine kinases, growth factor receptors, and adhesion molecules (e.g., selectins and integrins).

Some compounds are active within the cytoplasm, including for example, heparin, ribozymes, cytoxins, antisense oligonucleotides, and expression vectors. Other therapeutic approaches are directed at the nucleus. These include gene integration, proto-oncogenes, particularly those important for cell division, nuclear proteins, cell cycle genes, and transcription factors.

Other therapeutic substances that may be useful as stent coatings and/or depot formulations incorporated within degradable stents include: antibodies e.g., ICAM-1 antibodies for inhibition of monocyte chemotactic recruitment and adhesion, macrophage adhesion and associated events (Yasukawa et al, 1996, Circulation); toxin based therapies such as chimeric toxins or single toxins to control vascular SMC proliferation (Epstein et al., 1991, Circulation); bFGF-saporin to selectively stop SMC proliferation among those cells with a large number of FGF-2 receptors (Chen et al, 1995, Circulation), suramin inhibits migration and proliferation by blocking PDGF-induced and/or mitogen activated protein kinase (MAPK-AP-1)-induced signaling (Hu et al, Circulation, 1999); Beraprost Sodium, a chemically stable prostacyclin analogue (PGI2), suppresses intimal thickening and luminal narrowing of coronary arteries. (Kurisu et al., Hiroshima J. Med Sci, 1997); Verapamil inhibits neointimal smooth muscle cell proliferation (Brauner et al., J Thorac Cardiovasc Surg 1997), agents that block the CD 154 or CD40 receptor may limit the progression of atherosclerosis (E Lutgens et al., Nature Medicine 1999), agents that control responses of shear stress response elements or mechanical stress or strain elements or heat shock genes; and anti-chemoattractants for SMC and inflammatory cells.

In addition or in the alternative, cells could be encapsulated in a degradable microsphere, or mixed directly with polymer, or hydrogel. Living cells could be used to continuously deliver molecules, for instance, cytokines and growth factors. Cells of any origin may be used in accordance with this aspect of the present invention. Further, nonliving cells may be used and preserved, or dehydrated cells that retain their purpose when rehydrated may also be used. Still further, native cells, chemically modified (processed) cells, and/or genetically engineered cells may be used.

In various embodiments, the therapeutic agents may be polar or possess a net negative or positive or neutral charge. They may be hydrophobic, hydrophilic or zwitterionic or have a great affinity for water. Release may occur by controlled release mechanisms, diffusion, interaction with another agent(s) delivered by intravenous injection, aerosolization, or orally. Release may also occur by application of a magnetic field, an electrical field, or use of ultrasound.

In another aspect of the invention, the stent may also incorporate or deliver a hydrogel or other material such as phosphorylcholine (PC) that acts to prevent adhesions of blood cells, blood proteins or blood molecules, extracellular matrix or other cell types. The hydrogel may deliver a therapeutic agent.

Use of synthetic, natural (e.g., plant, microbial, viral or animal-derived) and recombinant agents having selected functions or chemical properties can be mixed with complementary substances (e.g., anti-thrombotic and anti-restenosis substances; nucleic acids and lipid complexes). Pharmacologic agents may also incorporate use of vitamins or minerals. For instance, those that function directly or indirectly through interactions or mechanisms involving amino acids, nucleic acids (e.g., DNA, RNA), proteins or peptides (e.g., RGD peptides), carbohydrate moieties, polysaccharides, liposomes, or other cellular components or organelles for instance receptors and ligands.

Genetic approaches to control restenosis include without limitation: use of antisense oligonucleotides to PDGFR-ββ mRNA to control PDGF expression; use of antisense oligonucleotides for nuclear antigens c-myb or c-myc oncogenes (Bauters et al., 1997, Trends CV Med); use of antisense phosphorothioate oligodeoxynucleotides against cdk 2 kinase (cyclin dependent kinase) to control the cell cycle of vascular smooth muscle cells (Morishita et al, 1993, Hypertension); use of VEGF gene (or VEGF itself) to stimulate reconstructive wound healing such as endothelialization and decrease neointima growth (Asahara et al 1995); delivery of the nitric oxide synthetase gene (eNOS) to reduce vascular smooth muscle cell proliferation (Von Der Leyen et al., 1995, Proc Natl Acad Sci); use of adenovirus expressing plasminogen activator inhibitor-1 (PAI-1) to reduce vascular SMOOTH MUSCLE CELL migration and thereby diminish restenosis (Carmeliet et al., 1997, Circulation); stimulation of apolipoprotein A-1 (ApoA1) over-expression to rebalance serum levels of LDL and HDL; use of apoptosis gene products to promote cell death (e.g., of smooth muscle cells) and cytotactic gene products to that regulate cell division (tumor suppressor protein p53 and Gax homeobox gene product to suppress ras; p21 over expression); and inhibition of NF-κB activation (e.g., p65) to control smooth muscle cell proliferation (Autieri et al., 1994, Biochem Biophys Res Commun).

In another advantageous feature, it will be appreciated that preferred embodiments of the present invention provide very efficient surface coverage, which is particularly advantageous when the stent is used with a therapeutic agent. More particularly, the slide and lock mechanism is configured such that virtually all the surface area of the locking elements is in contact with the inner wall of the body lumen. Accordingly, the preferred embodiments allow for greater surface coverage as compared with existing stent configurations. When compared with other stent configurations, such as those utilizing deformable struts, the surface coverage may be increased to as much as 25% to 70% without compromising stent performance or flexibility. Because the stent shape of various preferred embodiments provides excellent surface coverage, a larger amount of the therapeutic agent may be delivered to the surrounding tissue. As a result, the agent may be used more effectively, thereby increasing the therapeutic effect. Alternatively, the therapeutic agent may be used in a lower concentration, thereby reducing local toxicity.

Figure 23:
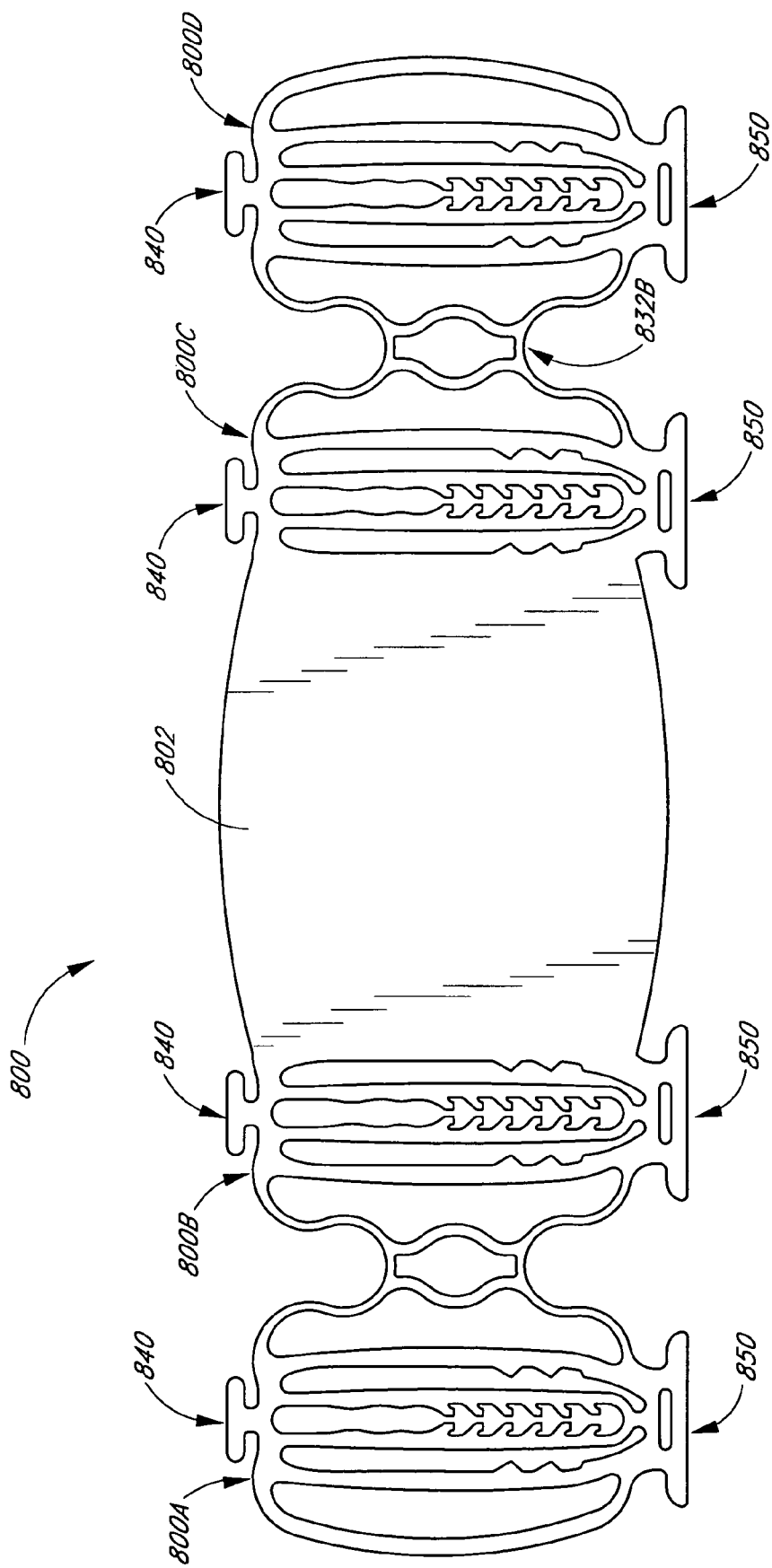
FIG. 23 is a plan view illustrating yet another preferred embodiment of a row of radial elements wherein a solid wall is provided along a center portion.

With reference now to FIG. 23, another row 800 of radial elements 800A-800D is illustrated that may be used alone or in combination with similar elements to provide an expandable stent structure. In many respects, the row 800 of radial elements 800A-800D is similar to the row described above with reference to FIG. 2. However, in this embodiment, the thin flexible body is formed with a solid wall 802 along a central portion of the row for providing enhanced surface coverage in a desired region of a body lumen. More particularly, the solid wall 802 is preferably fabricated from an impermeable material and is configured to provide substantially complete coverage along a portion of a body lumen. In preferred embodiments, the solid wall 802 extends along the longitudinal axis at least 2 millimeters. Accordingly, this embodiment is particularly well suited for placement along a vascular anomaly, such as a vascular aneurysm, for supporting or sealing off a particular region along a vessel.

In the illustrated embodiment, each radial element 800A-800D comprises a locking tab 812 that interacts with teeth along deflectable rails for providing a locking mechanism. Each radial element 800A-800D also includes a hold-down tab 850 sized to be releasably held within a recess for providing a hold down mechanism. Details regarding the operation of preferred locking and hold-down mechanisms are described above with respect to FIGS. 1 through 4B. However, it should be appreciated that a wide variety of locking mechanisms and hold-down mechanisms may be used and that the illustrated embodiment is merely for the purpose of description. Flexible coupling members 832A, 832B may be provided between individual elements to provide enhanced flexibility. In preferred embodiments, the row 800 of elements is fabricated from a shape memory material to provide crush-recoverability. During use, the row 800 is preferably slidably interconnected with other similar rows to provide a balloon expandable stent. However, in an alternative configuration, the element 800 of FIG. 23 may be wrapped onto itself to provide an expandable stent.

Figure 24:
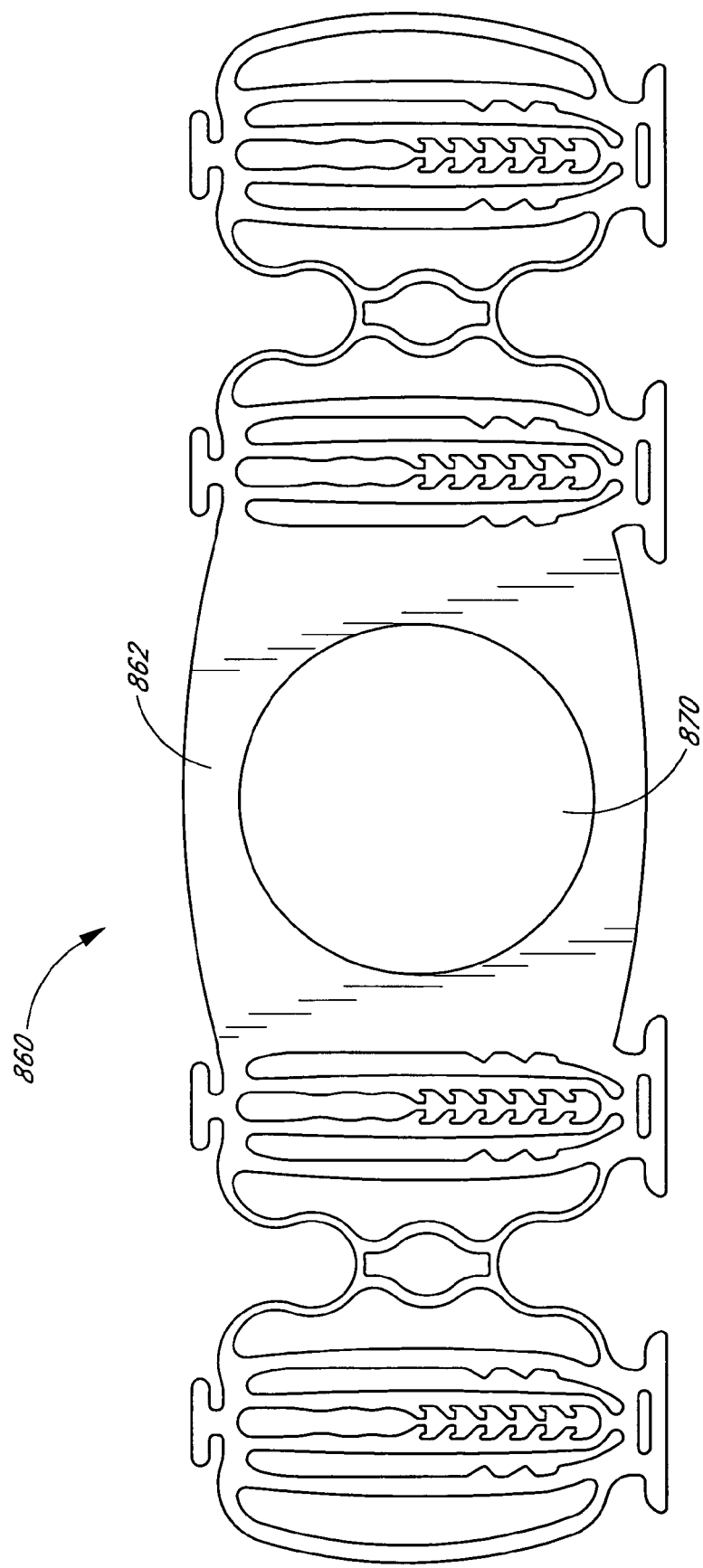
FIG. 24 illustrates a variation of the element of FIG. 23 wherein an opening is provided along the center portion of the solid wall for providing fluid communication with a branch vessel.

With reference now to FIG. 24, an alternative row 860 is illustrated which further comprises an opening 870 (e.g., a circular hole) formed in the wall portion 862. The opening is preferably provided for allowing fluid communication through the wall 862. Accordingly, this variation 860 is particularly well suited for treating a lesion along a vessel bifurcation. The row 860 may be interconnected with one or more rows 800 of the type described above with respect to FIG. 23 to provide an expandable stent having a solid central portion formed with an opening. When deployed, the stent may be advantageously used to ensure the patency of a main vessel while allowing blood to flow into or out of a branch vessel. In yet other variations, the wall may be permeable or a filter may be provided along the opening 870 for preventing emboli or other debris from passing through the opening.

In yet another variation, stent embodiments configured in accordance with the present invention may also be useful in vessel grafts, wherein the stent is covered with a sheath formed at least in part from either a polymeric material, such as expanded PTFE, or a natural material, such as fibrin. One variation of a graft in accordance with the present invention is illustrated in FIG. 25. The tubular graft comprises an expandable stent 10 of the type described above with reference to FIG. 1 and a polymeric sheath 900. Because of the low profile, small collapsed diameter and great flexibility, stents made in accordance with this embodiment may be able to navigate small or torturous paths. Thus, this variation may be useful in coronary arteries, carotid arteries, vascular aneurysms (when covered with a sheath), renal arteries, peripheral (iliac, femoral, popliteal, subclavian) arteries. Other nonvascular applications include gastrointestinal, duodenum, biliary ducts, esophagus, urethra, tracheal and bronchial ducts.

It will be appreciated that certain variations of the new and improved stents of the present invention and its methods of use and manufacture may suggest themselves to those skilled in the art. Accordingly, the foregoing detailed description is to be clearly understood as given by way of illustration, the spirit and scope of this invention being limited solely by the appended claims.

What is claimed is:

1. A balloon expandable crush-recoverable stent, comprising:
   at least two radial elements arranged to form a tubular member, the radial elements being slidably interconnected for allowing the tubular member to expand from a collapsed diameter to an expanded diameter, at least one radial element comprising;
      a locking mechanism for maintaining the tubular member in the expanded diameter after deployment, the locking mechanism comprising a plurality of teeth disposed on a first deflectable member that extends from a first end of the at least one radial element to a second end thereof, the locking mechanism further comprising a locking tab disposed at the first end of the at least one radial element; and
      a constraining mechanism integrated into the at least one radial element for maintaining the tubular member in the collapsed diameter until released by radial expansion, the constraining mechanism comprising at least one recess disposed on a first containment member that extends from the first end of the at least one radial element to the second end thereof, the constraining mechanism further comprising a hold-down tab disposed at the second end of the at least one radial element;
   wherein the radial elements are fabricated from a shape-memory material for providing crush-recoverability.

2. The balloon expandable crush-recoverable stent of claim 1, wherein the locking mechanism comprises a plurality of teeth disposed on a second deflectable member that extends from the first end of the at least one radial element to the second end thereof, the second deflectable member being disposed adjacent to the first deflectable member to form a gap therebetween, the gap being configured to receive the locking tab therein for allowing slidable movement in only one direction.

3. The balloon expandable crush-recoverable stent of claim 2, wherein the locking tab comprises a neck portion and a head portion that is wider than the neck portion, the neck portion of the at least one radial element extending through a gap formed between first and second deflectable members of a radial element.

4. The balloon expandable crush-recoverable stent of claim 1, wherein the teeth are deflectable for allowing the locking tab to pass over the teeth during expansion of the tubular member.

5. The balloon expandable crush-recoverable stent of claim 1, wherein the plurality of teeth allows the tubular member to be maintained at a selectable expanded diameter.

6. The balloon expandable crush-recoverable stent of claim 1, wherein the constraining mechanism further comprises at least one recess disposed on a second containment member that extends from the first end of the at least one radial element to the second end thereof, a hold-down tab of a first radial element configured to be releasably held within the recesses of the first and second containment members of the at least one radial element.

7. The balloon expandable crush-recoverable stent of claim 6, wherein the first containment member of the constraining mechanism is disposed adjacent to the first deflectable member of the locking mechanism to form a first gap therebetween, and wherein the second containment member of the constraining mechanism is disposed adjacent to the second deflectable member of the locking mechanism to form a second gap therebetween, the hold-down tab of the first radial element being positioned over the first and second deflectable members of the second radial element and disposed through the first and second gaps to be releasably held within the recesses of the first and second containment members of the second radial element.

8. The balloon expandable crush-recoverable stent of claim 1, wherein the tubular member is configured for delivering a therapeutic agent to a vessel wall at a treatment site.

9. The balloon expandable crush-recoverable stent of claim 8, wherein the therapeutic agent is an antiproliferative agent.

10. The balloon expandable crush-recoverable stent of claim 1, further comprising a retractable sheath sized for enclosing the tubular member during delivery to a treatment site.

11. The balloon expandable crush-recoverable stent of claim 1, wherein each radial element of the stent comprises a locking mechanism and a constraining mechanism.

12. The balloon expandable crush-recoverable stent of claim 1, wherein all of the radial elements of the stent have a substantially identical structure.

13. A balloon expandable stent, comprising:
   a substantially flat sheet fabricated from a shape-memory material, the flat sheet comprising at least one radial element being configured to be rolled into a cylindrical configuration for providing a tubular member, the tubular member being configured for expansion from a collapsed diameter to an expanded diameter, the at least one radial element comprising:
      a locking mechanism provided along the at least one radial element for maintaining the tubular member in the expanded diameter, the locking mechanism comprising first and second deflectable members extending from a first end of the at least one radial element to a second end thereof, the locking mechanism further comprising a locking tab disposed at the first end of the at least one radial element, the first and second deflectable members forming a gap therebetween, the gap being configured to receive the locking tab therein; and
      a constraining mechanism integrated into the at least one radial element for maintaining the tubular member in the collapsed diameter until released by radial expansion, the constraining mechanism comprising first and second containment members extending from the first end of the at least one radial element to the second end thereof, the first containment member being disposed adjacent to the first deflectable member of the locking mechanism to form a first gap therebetween, the second containment member being disposed adjacent to the second deflectable member of the locking mechanism to form a second gap therebetween, the constraining mechanism further comprising a hold-down tab disposed at the second end of the at least one radial element, the hold-down tab being positionable over first and second deflectable members and positionable through first and second gaps to maintain the at least one radial element in a slidable relationship.

14. A stent delivery system, comprising:
the balloon expandable stent of claim 13; and
a catheter with an inflatable balloon disposed along a distal end portion, wherein the stent is provided along an outer surface of the inflatable balloon.

15. A method for treating a vessel at a treatment site, comprising:
positioning the stent delivery system of claim 14 at the treatment site; and
inflating the inflatable balloon for causing the stent to expand from the collapsed diameter to the expanded diameter.

16. The balloon expandable stent of claim 13, wherein the locking mechanism comprises a plurality of teeth along the first and second deflectable members that are configured for slidable engagement with the locking tab.

17. The balloon expandable stent of claim 13, wherein the constraining mechanism comprises at least one recess formed along the first and second containment members, wherein the recesses of the first and second containment members are configured for capturing the hold-down tab.

18. The balloon expandable stent of claim 13, wherein the stent comprises first and second radial elements, the hold-down tab of a first radial element being disposed over the first and second deflectable members of a second radial element and disposed through the first and second gaps thereof to maintain the first and second radial elements in a slidable relationship.

19. The balloon expandable stent of claim 13, wherein the constraining mechanism comprises at least one hook disposed at the second end of the at least one radial element and at least one loop formed along a containment member at the second end of the at least one radial element.

20. The balloon expandable stent of claim 19, wherein a hook of a first radial element engages a loop of a second radial element, the hook being released from the loop upon radial expansion of an inflatable balloon for permitting expansion of the tubular member.

21. The balloon expandable stent of claim 20, wherein the loop is unbroken upon release of the hook therefrom.

22. The balloon expandable stent of claim 19, wherein the hook extends from the hold-down tab at the second end of the at least one radial element.

23. The balloon expandable stent of claim 13, wherein the constraining mechanism comprises at least one deflectable wing.

24. The balloon expandable stent of claim 23, wherein a deflectable wing of a first radial element is received within a gap formed between first and second deflectable members of a second radial element, the deflectable wing defining a passing profile that is larger than the gap, the deflectable wing being configured such that the wing can be disposed through the gap in an unexpanded state and provide initial resistance to radial expansion until flexing upon radial expansion of an inflatable balloon such that the deflectable wing is released from the gap for permitting expansion of the tubular member.

25. The balloon expandable stent of claim 13, wherein the locking tab of the locking mechanism comprises a neck portion and a head portion that is wider than the neck portion, a neck portion of a first element extending through a gap formed between first and second deflectable members of a second element.

26. The balloon expandable stent of claim 13, wherein the constraining mechanism comprises at least one deflectable arm disposed at the second end of the at least one radial element and at least one lock formed along a containment member of the at least one radial element, the arm extending from the at least one radial element such that the arm of the at least one radial element contacts a flexible lock of another radial element to provide initial resistance to radial expansion, the arm being deflectable relative to the lock to disengage with the lock upon forcible radial expansion.

27. The balloon expandable stent of claim 26, wherein the lock comprises a raised protrusion.

28. The balloon expandable stent of claim 13, wherein the constraining mechanism comprises an adhesive.

29. The balloon expandable stent of claim 13, wherein the first and second deflectable members are disposed between the first and second containment members.

30. A balloon expandable crush-recoverable stent, comprising:
a tubular member comprising a series of pivotally connected links fabricated from a shape-memory material, each link comprising a first end and a second end, each link comprising one or more ridges along the surface thereof, the ridges of a given link being configured to contact ridges of an adjacent pivotally connected link to limit the pivoting of the given link and the adjacent link relative to each other in a collapsed direction, the pivotally connected links being configured for allowing the tubular member to be adjusted from a collapsed diameter to an expanded diameter, at least one link comprising:
a locking mechanism formed between the first and second ends of the at least one link, the locking mechanism configured for maintaining the tubular member in the expanded diameter; and
a constraining mechanism integrated into the tubular member and formed between the first and second ends of the at least one link, the constraining mechanism configured for maintaining the tubular member in the collapsed diameter until released by radial expansion of the balloon; and
a flexible mechanism for connecting multiple links together to form a stent having a desired axial length.

31. The balloon expandable crush-recoverable stent of claim 30, wherein the tubular member is configured for delivering a therapeutic agent to a vessel wall at a treatment site.

32. The balloon expandable crush-recoverable stent of claim 30, wherein each link of the tubular member comprises a locking mechanism and a constraining mechanism.

33. The balloon expandable crush-recoverable stent of claim 30, wherein all of the links of the tubular member have a substantially identical structure.

34. An expandable stent, comprising:
a tubular member comprising a series of slidably interconnected elements fabricated from a biocompatible material, the tubular member being configured for expansion from a collapsed diameter to an expanded diameter, at least one element comprising:
a locking mechanism for maintaining the tubular member in the expanded diameter, the locking mechanism comprising a plurality of teeth disposed on a deflectable member that extends from a first end of the at least one element to a second end thereof, the locking mechanism further comprising a locking tab disposed at the first end of the at least one element; and
a constraining mechanism for maintaining the tubular member in the collapsed diameter until released by radial expansion, the constraining mechanism comprising at least one lock formed along a containment member that extends from the first end of the at least one element to the second end thereof, the constraining mechanism further comprising at least one arm disposed at the second end of the at least one element, the arm extending from the at least one element such that the arm of the at least one element contacts a lock of an element to provide initial resistance to radial expansion, the arm being deflectable relative to the lock to disengage with the lock upon forcible radial expansion.

35. The expandable stent of claim 34, wherein the biocompatible material includes a therapeutic agent for delivery to a vessel wall.

36. The expandable stent of claim 34, wherein each element of the tubular member comprises a locking mechanism and a constraining mechanism.

37. The expandable stent of claim 34, wherein all of the elements of the tubular member have a substantially identical structure.

38. An expandable stent, comprising:
first and second expandable modules, each expandable module comprising at least one radial element, each expandable module forming a substantially tubular member and being adjustable from a collapsed condition to an expanded condition, at least one radial element comprising:
a locking mechanism for maintaining the tubular member in the expanded diameter after deployment, the locking mechanism comprising a plurality of teeth disposed on a first deflectable member that extends from a first end of the at least one radial element to a second end thereof, the locking mechanism further comprising a locking tab disposed at the first end of the at least one radial element; and
a constraining mechanism for maintaining the stent in the collapsed condition during delivery to a treatment site, the constraining mechanism comprising at least one recess disposed on a first containment member that extends from the first end of the at least one radial element to the second end thereof, the constraining mechanism further comprising a hold-down tab disposed at the second end of the at least one radial element; and
a flexible coupling portion for coupling the first and second expandable modules together;
wherein each of the expandable modules is substantially independently expandable.

39. The expandable stent of claim 38, wherein at least one of the expandable modules is fabricated from a shape memory material.

40. The expandable stent of claim 38, wherein at least one of the expandable modules comprises a plurality of radial elements slidably interconnected for allowing the stent to expand from the collapsed condition to the expanded condition.

41. The expandable stent of claim 40, wherein the locking mechanism of the at least one radial element further comprises a second deflectable member, the first and second deflectable members defining a gap therebetween for slidably interconnecting with a locking tab of the at least one radial element.

42. The expandable stent of claim 41, wherein each of the first and second deflectable members comprises a plurality of angled teeth, and wherein the locking tab of the at least one radial element is held within the teeth of the at least one radial element for providing the locking mechanism.

43. The expandable stent of claim 40, wherein the constraining mechanism further comprises a second containment member, the first containment member of the constraining mechanism being disposed adjacent to the first deflectable member of the locking mechanism to form a first gap therebetween, the second containment member of the constraining mechanism being disposed adjacent to the second deflectable member of the locking mechanism to form a second gap therebetween, a hold-down tab of a radial element being positioned over the first and second deflectable members of the at least one radial element and disposed through the first and second gaps of the at least one radial element for providing the constraining mechanism.

44. The expandable stent of claim 43, wherein the first and second containment members comprise at least one recess configured to releasably receive the hold-down tab, the hold-down tab being deformable such that the hold-down tab is releasable from within the recesses of the first and second containment members of the at least one radial element under a sufficient radial force during deployment.

45. The expandable stent of claim 43, wherein the first and second containment members are deformable such that the hold-down tab is releasable under a sufficient radial force during deployment.

46. The expandable stent of claim 38, wherein each radial element of the first and second expandable modules comprises a locking mechanism and a constraining mechanism.

47. The expandable stent of claim 38, wherein all of the radial elements of the first and second expandable modules have a substantially identical structure.

48. An expandable stent for supporting a blood vessel, comprising:
a tubular member fabricated from a biocompatible material, the tubular member comprising at least one radial element and having a first end portion and a second end portion, the tubular member being configured for expansion from a collapsed diameter to an expanded diameter, the tubular member having a central region disposed between the first end portion and the second end portion, the at least one radial element comprising:
a locking mechanism for maintaining the tubular member in the expanded diameter after deployment, the locking mechanism comprising a plurality of teeth disposed on a first deflectable member that extends from a first end of the at least one radial element to a second end thereof, the locking mechanism further comprising a locking tab disposed at the first end of the at least one radial element; and
a constraining mechanism for maintaining the tubular member in the collapsed diameter until released by radial expansion, the constraining mechanism comprising at least one recess disposed on a first containment member that extends from the first end of the at least one radial element to the second end thereof, the constraining mechanism further comprising a hold-down tab disposed at the second end of the at least one radial element; and
wherein at least a portion of the central region of the tubular member is formed with a substantially impermeable wall.

49. The expandable stent of claim 48, wherein the impermeable wall extends at least 2 mm along the length of the stent.

50. The expandable stent of claim 48, further comprising an opening formed through the impermeable wall for allowing blood to pass into a branch vessel.

51. A balloon expandable crush-recoverable stent, comprising:
a first row of radial elements extending along the longitudinal axis of the stent;

a second row of radial elements extending along the longitudinal axis of the stent;

wherein a radial element of the first row and a corresponding radial element of second row each comprises:

a locking mechanism comprising a plurality of teeth disposed on a first deflectable member that extends from a first end of the radial element to a second end thereof, the locking mechanism further comprising a locking tab disposed at the first end of the radial element; and a constraining mechanism comprising at least one loop formed along a first containment member that extends from the first end of the radial element to a second end thereof, the constraining mechanism further comprising at least one hook disposed at the second end of the radial element;

wherein the locking tab of the radial element of the second row is operative to engage the teeth of the radial element of the first row; and wherein the radial elements in the first row slidably interconnect with the radial elements in the second row for providing a series of expandable modules, the constraining mechanism maintaining at least one expandable module in a collapsed diameter until released by radial expansion of an inflatable balloon, wherein each of the modules is expandable to a different diameter.

52. The balloon expandable crush-recoverable stent of claim 51, wherein the constraining mechanism comprises a hook and a loop, wherein a hook of the radial element of the first row can be releasably held within a loop of the radial element of the second row for maintaining the collapsed diameter.

53. The balloon expandable crush-recoverable stent of claim 51, wherein at least some of the radial elements in each of the first and second rows are coupled by flexible coupling members.

54. The balloon expandable crush-recoverable stent of claim 51, wherein the radial elements in each of the first and second rows are coupled together in a staggered arrangement.

55. The balloon expandable crush-recoverable stent of claim 51, wherein each radial element of the stent comprises a locking mechanism and a constraining mechanism.

56. The balloon expandable crush-recoverable stent of claim 51, wherein all of the radial elements of the stent have a substantially identical structure.

57. A balloon expandable crush-recoverable stent, comprising:

a first row of radial elements extending along the longitudinal axis of the stent;

a second row of radial elements extending along the longitudinal axis of the stent;

wherein at least one radial element comprises:

a locking mechanism comprising a plurality of teeth disposed on a first deflectable member that extends from a first end of the at least one radial element a second end thereof, the locking mechanism further comprising a locking tab disposed at the first end of the at least one radial element, the locking tab of the at least one radial element being operative to engage the teeth of another radial element; and a constraining element comprising a gap formed by at least one deflectable member at a second end of the at least one radial element, the constraining mechanism further comprising a flexible wing disposed at the second end of the at least one radial element, the flexible wing defining a passing profile that is larger than the gap, the wing being configured such that the wing can be disposed through a gap of another radial element with the stent being in an unexpanded state and provide initial resistance to radial expansion of the stent until deflecting and exiting the gap;

wherein the first and second rows of radial elements form at least a portion of a tubular member, the first and second rows of radial elements being slidably interconnected along a plurality of points for allowing the tubular member to expand from a collapsed condition to an expanded condition, the constraining mechanism maintaining the tubular member in the collapsed condition until released by radial expansion of an inflatable balloon.

58. The balloon expandable crush-recoverable stent of claim 57, wherein each radial element of the stent comprises a locking mechanism and a constraining element.

59. The balloon expandable crush-recoverable stent of claim 57, wherein all of the radial elements of the stent have a substantially identical structure.

60. A balloon expandable crush-recoverable stent, comprising:

first and second expandable modules, each module comprising a series of slidably interconnected elements fabricated from a shape-memory material, each element comprising a pair of containment members extending generally parallel to at least one deflectable member that is spaced between the containment members, the containment members and the deflectable member extending from a first end of the element to a second end thereof, the containment members being spaced from the at least one deflectable member to define first and second gaps therebetween, the interconnected elements being configured for allowing the module to be adjusted from a collapsed diameter to an expanded diameter, each element further comprising:

a locking mechanism being configured such that the interconnected elements are slidable in only one direction for maintaining the expandable module in the expanded diameter; and a constraining mechanism comprising a hold-down tab extending from the second end of each radial element, a hold-down tab of a first radial element being disposed over at least one deflectable member and disposed through first and second gaps of a second radial element to maintain the first and second radial elements in a slidable relationship, the constraining mechanism being configured to maintain the expandable module in the collapsed diameter until released by radial expansion of an inflatable balloon during deployment at a treatment site.

61. The balloon expandable crush-recoverable stent of claim 60, wherein each element comprises a pair deflectable members extending between the pair of containment members.

62. The balloon expandable stent of claim 60, wherein all of the elements of the modules have a substantially identical structure.

63. A balloon expandable stent, comprising:

at least two substantially flat elements configured to be rolled into a cylindrical configuration to provide a tubular member, each of the flat elements forming a portion of a circumference of the tubular member, the elements being slidably interconnected for allowing the tubular member to expand from a collapsed diameter to an expanded diameter without any substantial plastic deformation of the elements, at least one element comprising:

a locking mechanism comprising a plurality of teeth disposed on a first deflectable member that extends from a first end of the at least one element to a second end thereof, the locking mechanism further comprising a locking tab disposed at the first end of the at least one element; and a constraining mechanism for maintaining the tubular member in the collapsed diameter until released by radial expansion, the constraining mechanism comprising at least one loop formed along a first containment member that extends from the first end of the at least one element to the second end thereof, the constraining mechanism further comprising at least one hook disposed at the second end of the at least one element; and an expandable sheath disposed over the tubular member, the expandable sheath being configured to expand during deployment of the stent at the treatment site.

64. The balloon expandable stent of claim 63, wherein the elements are fabricated from a shape-memory material for providing the tubular member with crush-recoverability.

65. The balloon expandable stent of claim 64, wherein the expandable sheath is configured for use as a vessel graft at a treatment site.

66. The balloon expandable stent of claim 63, wherein each element of the tubular member comprises a locking mechanism and a constraining mechanism.

67. The balloon expandable stent of claim 63, wherein all of the elements of the tubular member have a substantially identical structure.

* * * * *

UNITED STATES PATENT AND TRADEMARK OFFICE
CERTIFICATE OF CORRECTION

| | | |
|---|---|---|
| PATENT NO. | : 7,763,065 B2 | Page 1 of 1 |
| APPLICATION NO. | : 10/897235 | |
| DATED | : July 27, 2010 | |
| INVENTOR(S) | : Eric V. Schmid et al. | |

It is certified that error appears in the above-identified patent and that said Letters Patent is hereby corrected as shown below:

Title Page; item (56);
On page 3 at column 1, below "6,409,750 B1" insert --6,409,751   06/2002   Boatman et al.--.

In column 31 at line 17, change "comprising;" to --comprising:--.

In column 31 at line 64, before "radial" delete "first".

Signed and Sealed this
Twenty-fourth Day of May, 2011

David J. Kappos
*Director of the United States Patent and Trademark Office*